(12) United States Patent
Lee-Sepsick et al.

(10) Patent No.: US 12,171,463 B2
(45) Date of Patent: *Dec. 24, 2024

(54) CONTRAST AGENT GENERATION AND INJECTION SYSTEM FOR SONOGRAPHIC IMAGING

(71) Applicant: FEMASYS INC, Suwannee, GA (US)

(72) Inventors: Kathy Lee-Sepsick, Suwanee, GA (US); Max S. Azevedo, Alpharetta, GA (US)

(73) Assignee: Femasys Inc., Suwanee, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/133,721

(22) Filed: Apr. 12, 2023

(65) Prior Publication Data
US 2023/0240716 A1 Aug. 3, 2023

Related U.S. Application Data

(63) Continuation of application No. 16/186,553, filed on Nov. 11, 2018, now abandoned, which is a (Continued)

(51) Int. Cl.
*A61B 8/14* (2006.01)
*A61B 17/42* (2006.01)
(Continued)

(52) U.S. Cl.
CPC .............. *A61B 17/42* (2013.01); *A61M 5/007* (2013.01); *A61M 5/1407* (2013.01);
(Continued)

(58) Field of Classification Search
CPC ........ A61B 17/42; A61B 8/481; A61M 5/007; A61M 5/1407; A61M 31/005; A61M 5/1452; A61M 25/04; A61M 25/10
See application file for complete search history.

(56) References Cited

U.S. PATENT DOCUMENTS 1,892,803 A 1/1933 Lawshe
3,042,030 A 7/1962 Read
(Continued)

FOREIGN PATENT DOCUMENTS

BR 1120130114347 11/2011
CA 2770504 10/2009
(Continued)

OTHER PUBLICATIONS

Office Action, issued Oct. 24, 2019, for BR Application No. 1120130114347, filed Nov. 9, 2011, (Lee-Sepsick et al.—Inventors) (4 pages).
(Continued)

*Primary Examiner* — Christopher L Cook
(74) *Attorney, Agent, or Firm* — Mary Anthony Merchant

(57) ABSTRACT

The present invention comprises methods and devices for generating and providing contrast medium for sonography of structures such as ducts or cavities. The invention provides for creation of a contrast medium comprising detectable acoustic variations between two phases, for example, a gas and a liquid. Sonography is the primary means of imaging but other conventional detection means may also be employed with the present invention.

22 Claims, 11 Drawing Sheets

Related U.S. Application Data continuation of application No. 15/404,887, filed on Jan. 12, 2017, now Pat. No. 10,172,643, which is a continuation of application No. 13/219,667, filed on Aug. 27, 2011, now Pat. No. 9,554,826, said application No. 16/186,553 is a continuation-in-part of application No. 12/245,265, filed on Oct. 3, 2008, now Pat. No. 10,070,888.

(60) Provisional application No. 61/411,856, filed on Nov. 9, 2010.

(51) Int. Cl.

| | | |
|---|---|---|
| *A61M 5/00* | (2006.01) | |
| *A61M 5/14* | (2006.01) | |
| *A61M 5/145* | (2006.01) | |
| *A61B 8/08* | (2006.01) | |
| *A61M 31/00* | (2006.01) | |

(52) U.S. Cl.
CPC ........... *A61M 5/1452* (2013.01); *A61B 8/481* (2013.01); *A61M 31/005* (2013.01)

(56) References Cited

U.S. PATENT DOCUMENTS

| | | |
|---|---|---|
| 3,182,662 A | 5/1965 | Shirodkar |
| 3,404,682 A | 10/1968 | Waldron |
| 3,405,711 A | 10/1968 | Bakunin |
| 3,422,813 A | 1/1969 | Braley et al. |
| 3,463,141 A | 8/1969 | Mozolf |
| 3,467,090 A | 9/1969 | Zollett |
| 3,598,115 A | 8/1971 | Home |
| 3,645,258 A | 2/1972 | Massouras |
| 3,675,642 A | 7/1972 | Lord |
| 3,680,542 A | 8/1972 | Cimber |
| 3,687,129 A | 8/1972 | Nuwayser |
| 3,768,102 A | 10/1973 | Kwan-Gett et al. |
| 3,774,600 A | 11/1973 | Cognat |
| 3,803,308 A | 4/1974 | Zipper |
| 3,805,767 A | 4/1974 | Erb |
| 3,822,702 A | 7/1974 | Bolduc et al. |
| 3,855,996 A | 12/1974 | Bolduc |
| 3,856,016 A | 12/1974 | Davis |
| 3,858,571 A | 1/1975 | Rudolph |
| 3,858,586 A | 1/1975 | Lessen |
| 3,871,374 A | 3/1975 | Bolduc et al. |
| 3,875,939 A | 4/1975 | Bolduc et al. |
| 3,882,854 A | 5/1975 | Hulka et al. |
| 3,918,431 A | 11/1975 | Sinnreich |
| 3,948,259 A | 4/1976 | Bolduc et al. |
| 3,954,108 A | 5/1976 | Davis |
| 3,967,625 A | 7/1976 | Yoon |
| 3,972,331 A | 8/1976 | Bolduc et al. |
| 3,973,560 A | 8/1976 | Emmett |
| RE29,207 E | 5/1977 | Bolduc et al. |
| RE29,345 E | 8/1977 | Erb |
| 4,109,654 A | 8/1978 | Bolduc et al. |
| 4,119,098 A | 10/1978 | Bolduc et al. |
| 4,126,134 A | 11/1978 | Bolduc et al. |
| 4,135,495 A | 1/1979 | Borgen |
| 4,136,695 A | 1/1979 | Dafoe |
| 4,158,050 A | 6/1979 | Zipper |
| 4,160,446 A | 7/1979 | Barrington |
| 4,181,725 A | 1/1980 | Voorhees et al. |
| 4,182,328 A | 1/1980 | Bolduc et al. |
| 4,185,618 A | 1/1980 | Corey |
| 4,207,891 A | 6/1980 | Bolduc |
| 4,226,239 A | 10/1980 | Polk et al. |
| 4,230,116 A | 10/1980 | Watson |
| 4,245,623 A | 1/1981 | Erb |
| 4,267,839 A | 5/1981 | Laufe et al. |
| 4,359,454 A | 11/1982 | Hoffman |
| 4,365,621 A | 12/1982 | Brundin |
| 4,374,523 A | 2/1983 | Yoon |
| 4,380,238 A | 4/1983 | Colucci et al. |
| 4,416,660 A | 11/1983 | Dafoe |
| 4,466,442 A | 8/1984 | Hilmann et al. |
| 4,485,814 A | 12/1984 | Yoon |
| 4,489,725 A | 12/1984 | Casey et al. |
| 4,509,504 A | 4/1985 | Brundin |
| 4,523,590 A | 6/1985 | Roth et al. |
| 4,537,186 A | 8/1985 | Verschoof et al. |
| 4,547,188 A | 10/1985 | Bolduc |
| 4,548,201 A | 10/1985 | Yoon |
| 4,579,110 A | 4/1986 | Hamou |
| 4,595,000 A | 6/1986 | Hamou |
| 4,601,698 A | 7/1986 | Moulding, Jr. |
| 4,606,336 A | 8/1986 | Zeluff |
| 4,611,602 A | 9/1986 | Bolduc |
| 4,631,188 A | 12/1986 | Stoy et al. |
| 4,637,818 A | 1/1987 | Johnson et al. |
| 4,664,112 A | 5/1987 | Kensey et al. |
| 4,679,558 A | 7/1987 | Kensey et al. |
| 4,681,106 A | 7/1987 | Kensey et al. |
| 4,700,701 A | 10/1987 | Montaldi |
| 4,700,705 A | 10/1987 | Kensey et al. |
| 4,713,235 A | 12/1987 | Krall |
| 4,731,052 A | 3/1988 | Seitz, Jr. |
| 4,788,966 A | 12/1988 | Yoon |
| 4,794,927 A | 1/1989 | Yoon |
| 4,795,438 A | 1/1989 | Kensey et al. |
| 4,804,691 A | 2/1989 | English et al. |
| 4,808,399 A | 2/1989 | Rypacek et al. |
| 4,824,434 A | 4/1989 | Seitz, Jr. |
| 4,832,941 A | 5/1989 | Berwing et al. |
| 4,834,091 A | 5/1989 | Ott |
| 4,847,065 A | 7/1989 | Akimova et al. |
| 4,869,268 A | 9/1989 | Yoon |
| 4,932,422 A | 6/1990 | Ragheb |
| 4,937,254 A | 6/1990 | Sheffield et al. |
| 4,938,763 A | 7/1990 | Dunn et al. |
| 4,983,177 A | 1/1991 | Wolf |
| 5,026,379 A | 6/1991 | Yoon |
| 5,065,751 A | 11/1991 | Wolf |
| 5,095,917 A | 3/1992 | Vancaillie |
| 5,147,353 A | 9/1992 | Everett |
| 5,193,554 A | 3/1993 | McQuilkin |
| 5,211,627 A | 5/1993 | William |
| 5,217,030 A | 6/1993 | Yoon |
| 5,217,473 A | 6/1993 | Yoon |
| 5,226,908 A | 7/1993 | Yoon |
| 5,273,527 A | 12/1993 | Schatz et al. |
| 5,278,201 A | 1/1994 | Dunn et al. |
| 5,278,202 A | 1/1994 | Dunn et al. |
| 5,324,519 A | 6/1994 | Dunn et al. |
| 5,328,687 A | 7/1994 | Leung et al. |
| 5,334,209 A | 8/1994 | Yoon |
| 5,340,849 A | 8/1994 | Dunn et al. |
| 5,350,798 A | 9/1994 | Linden et al. |
| 5,352,436 A | 10/1994 | Wheatley et al. |
| 5,364,345 A | 11/1994 | Lowery et al. |
| 5,372,584 A | 12/1994 | Zink et al. |
| 5,374,247 A | 12/1994 | Lowery et al. |
| 5,389,089 A | 2/1995 | Bauer et al. |
| 5,391,146 A | 2/1995 | That et al. |
| 5,439,022 A | 8/1995 | Summers |
| 5,464,395 A | 11/1995 | Faxon et al. |
| 5,469,867 A | 11/1995 | Schmitt |
| 5,474,089 A | 12/1995 | Waynant |
| 5,478,837 A | 12/1995 | Rodgers et al. |
| 5,487,390 A | 1/1996 | Cohen et al. |
| 5,487,897 A | 1/1996 | Poison et al. |
| 5,551,443 A | 9/1996 | Sepetka et al. |
| 5,562,099 A | 10/1996 | Cohen et al. |
| 5,575,802 A | 11/1996 | McQuilkin et al. |
| 5,599,552 A | 2/1997 | Dunn et al. |
| 5,601,600 A | 2/1997 | Ton |
| 5,612,052 A | 3/1997 | Shalaby |
| 5,632,727 A | 5/1997 | Tipton et al. |
| 5,632,753 A | 5/1997 | Loeser |
| 5,634,877 A | 6/1997 | Salama |
| 5,681,873 A | 10/1997 | Norton et al. |

(56) References Cited

U.S. PATENT DOCUMENTS

| | | |
|---|---|---|
| 5,701,899 A | 12/1997 | Porter |
| 5,702,716 A | 12/1997 | Dunn et al. |
| 5,702,717 A | 12/1997 | Cha et al. |
| 5,704,899 A | 1/1998 | Milo |
| 5,714,159 A | 2/1998 | Shalaby |
| 5,716,321 A | 2/1998 | Kerin et al. |
| 5,725,777 A | 3/1998 | Taylor |
| 5,733,950 A | 3/1998 | Dunn et al. |
| 5,736,152 A | 4/1998 | Dunn |
| 5,739,176 A | 4/1998 | Dunn et al. |
| 5,744,153 A | 4/1998 | Yewey et al. |
| 5,780,044 A | 4/1998 | Yewey et al. |
| 5,746,769 A | 5/1998 | Ton et al. |
| 5,747,058 A | 5/1998 | Tipton et al. |
| 5,752,974 A | 5/1998 | Rhee et al. |
| 5,759,563 A | 6/1998 | Yewey et al. |
| 5,788,716 A | 8/1998 | Kobren et al. |
| 5,792,469 A | 8/1998 | Tipton et al. |
| 5,795,288 A | 8/1998 | Cohen et al. |
| 5,795,331 A | 8/1998 | Cragg et al. |
| 5,807,239 A | 9/1998 | DiBernardo |
| 5,826,584 A | 10/1998 | Schmitt |
| 5,830,228 A | 11/1998 | Knapp et al. |
| 5,843,121 A | 12/1998 | Yoon |
| 5,846,255 A | 12/1998 | Casey |
| 5,866,554 A | 2/1999 | Shalaby et al. |
| 5,873,815 A | 2/1999 | Kerin et al. |
| 5,885,601 A | 3/1999 | Sokal |
| 5,888,533 A | 3/1999 | Dunn |
| 5,891,192 A | 4/1999 | Murayama et al. |
| 5,891,457 A | 4/1999 | Neuwirth |
| 5,894,022 A | 4/1999 | Ji et al. |
| 5,919,434 A | 7/1999 | Dugstad et al. |
| 5,935,056 A | 8/1999 | Kerin et al. |
| 5,935,098 A | 8/1999 | Blaisdell et al. |
| 5,935,137 A | 8/1999 | Saadat et al. |
| 5,947,958 A | 9/1999 | Woodard et al. |
| 5,947,977 A | 9/1999 | Slepian et al. |
| 5,954,715 A | 9/1999 | Harrington et al. |
| 5,955,143 A | 9/1999 | Wheatley et al. |
| 5,962,006 A | 10/1999 | Southard et al. |
| 5,968,542 A | 10/1999 | Tipton |
| 5,972,002 A | 10/1999 | Bark et al. |
| 5,979,446 A | 11/1999 | Loy |
| 5,989,580 A | 11/1999 | Wallace et al. |
| 5,990,194 A | 11/1999 | Dunn et al. |
| 6,010,714 A | 1/2000 | Leung et al. |
| 6,019,757 A | 2/2000 | Scheldrup |
| 6,026,331 A | 2/2000 | Feldberg et al. |
| 6,037,331 A | 3/2000 | Shalaby et al. |
| 6,042,590 A | 3/2000 | Sporri et al. |
| 6,059,747 A | 5/2000 | Bruggeman |
| 6,066,139 A | 5/2000 | Ryan et al. |
| 6,068,626 A | 5/2000 | Harrington et al. |
| 6,071,283 A | 6/2000 | Nardella et al. |
| 6,080,129 A | 6/2000 | Blaisdell |
| 6,080,152 A | 6/2000 | Nardella et al. |
| 6,096,052 A | 8/2000 | Callister et al. |
| 6,103,254 A | 8/2000 | Wallace et al. |
| 6,112,747 A | 9/2000 | Jones et al. |
| 6,113,614 A | 9/2000 | Mears |
| 6,120,789 A | 9/2000 | Dunn |
| 6,130,200 A | 10/2000 | Brodbeck et al. |
| 6,143,352 A | 11/2000 | Clark et al. |
| 6,145,505 A | 11/2000 | Nikolchev et al. |
| 6,152,943 A | 11/2000 | Sawhney |
| 6,165,492 A | 12/2000 | Neuwirth |
| 6,174,919 B1 | 1/2001 | Hickey |
| 6,176,240 B1 | 1/2001 | Nikolchev et al. |
| 6,179,832 B1 | 1/2001 | Jones et al. |
| 6,187,346 B1 | 2/2001 | Neuwirth |
| 6,196,966 B1 | 3/2001 | Kerin et al. |
| 6,197,351 B1 | 3/2001 | Neuwirth |
| 6,245,090 B1 | 6/2001 | Gilson et al. |
| 6,258,084 B1 | 7/2001 | Goldman et al. |
| 6,290,672 B1 | 9/2001 | Abae |
| 6,297,337 B1 | 10/2001 | Marchant et al. |
| 6,299,631 B1 | 10/2001 | Shalaby |
| 6,306,243 B1 | 10/2001 | Clark et al. |
| 6,309,384 B1 | 10/2001 | Harrington et al. |
| 6,315,762 B1 | 11/2001 | Recinella |
| 6,327,505 B1 | 12/2001 | Medhkour et al. |
| 6,346,102 B1 | 2/2002 | Harrington et al. |
| 6,357,443 B1 | 3/2002 | Loy |
| 6,371,975 B2 | 4/2002 | Cruise et al. |
| 6,378,524 B1 | 4/2002 | Jones |
| 6,379,373 B1 | 4/2002 | Sawhney et al. |
| 6,395,293 B2 | 5/2002 | Poison et al. |
| 6,401,719 B1 | 6/2002 | Farley et al. |
| 6,413,536 B1 | 7/2002 | Gibson et al. |
| 6,413,539 B1 | 7/2002 | Shalaby |
| 6,432,116 B1 | 8/2002 | Callister et al. |
| 6,433,096 B1 | 8/2002 | Hickey et al. |
| 6,450,963 B1 | 9/2002 | Ackerman |
| 6,455,064 B1 | 9/2002 | Narang et al. |
| 6,458,147 B1 | 10/2002 | Cruise et al. |
| 6,461,631 B1 | 10/2002 | Dunn et al. |
| 6,465,001 B1 | 10/2002 | Hubbell et al. |
| 6,476,069 B2 | 11/2002 | Krall et al. |
| 6,476,070 B2 | 11/2002 | Krall et al. |
| 6,485,486 B1 | 11/2002 | Trembly et al. |
| RE37,950 E | 12/2002 | Dunn et al. |
| 6,493,589 B1 | 12/2002 | Medhkour et al. |
| 6,514,534 B1 | 2/2003 | Sawhney |
| 6,514,535 B2 | 2/2003 | Marchant |
| 6,526,979 B1 | 3/2003 | Nikolchev et al. |
| 6,528,080 B2 | 3/2003 | Dunn et al. |
| 6,538,026 B1 | 3/2003 | Krall et al. |
| 6,539,265 B2 | 3/2003 | Medhkour et al. |
| 6,550,480 B2 | 4/2003 | Feldman et al. |
| 6,565,557 B1 | 5/2003 | Sporri et al. |
| 6,577,903 B1 | 6/2003 | Cronin et al. |
| 6,579,469 B1 | 6/2003 | Nicholson et al. |
| 6,599,299 B2 | 7/2003 | Schultz |
| 6,605,294 B2 | 8/2003 | Sawhney |
| 6,605,667 B1 | 8/2003 | Badejo et al. |
| 6,607,631 B1 | 8/2003 | Badejo et al. |
| 6,610,033 B1 | 8/2003 | Melanson et al. |
| 6,620,846 B1 | 9/2003 | Jonn et al. |
| 6,634,361 B1 | 10/2003 | Nikolchev et al. |
| 6,635,055 B1 | 10/2003 | Cronin |
| 6,663,607 B2 | 12/2003 | Slaikeu et al. |
| 6,676,971 B2 | 1/2004 | Goupil et al. |
| 6,679,266 B2 | 1/2004 | Nikolchev et al. |
| 6,682,526 B1 | 1/2004 | Jones et al. |
| 6,684,884 B2 | 2/2004 | Nikolchev et al. |
| 6,689,148 B2 | 2/2004 | Sawhney et al. |
| 6,699,940 B2 | 3/2004 | Shalaby |
| 6,703,047 B2 | 3/2004 | Sawhney et al. |
| 6,705,323 B1 | 3/2004 | Nikolchev et al. |
| 6,709,667 B1 | 3/2004 | Lowe et al. |
| 6,712,810 B2 | 3/2004 | Harrington et al. |
| 6,723,144 B2 | 4/2004 | Katagiri et al. |
| 6,723,781 B1 | 4/2004 | Frate et al. |
| 6,726,682 B2 | 4/2004 | Harrington et al. |
| 6,736,822 B2 | 5/2004 | McClellan et al. |
| 6,743,248 B2 | 6/2004 | Edwards et al. |
| 6,752,803 B2 | 6/2004 | Goldman et al. |
| 6,758,831 B2 | 7/2004 | Ryan |
| 6,763,833 B1 | 7/2004 | Khera et al. |
| 6,780,182 B2 | 8/2004 | Bowman et al. |
| 8,048,086 B2 | 11/2011 | Lee-Sepsick |
| 8,048,101 B2 | 11/2011 | Lee-Sepsick |
| 8,052,669 B2 | 11/2011 | Lee-Sepsick |
| 8,316,854 B2 | 2/2012 | Lee-Sepsick |
| 8,316,853 B2 | 11/2012 | Lee-Sepsick |
| 8,324,193 B2 | 12/2012 | Lee-Sepsick |
| 8,336,552 B2 | 12/2012 | Lee-Sepsick |
| 8,695,606 B2 | 4/2014 | Lee-Sepsick |
| 8,726,906 B2 | 5/2014 | Lee-Sepsick |
| 9,220,880 B2 | 12/2015 | Lee-Sepsick |
| 9,238,127 B2 | 1/2016 | Lee-Sepsick |
| 9,308,023 B2 | 4/2016 | Lee-Sepsick |
| 9,402,762 B2 | 8/2016 | Lee-Sepsick |

(56) References Cited

U.S. PATENT DOCUMENTS

| | | |
|---|---|---|
| 9,839,444 B2 | 12/2017 | Lee-Sepsick |
| 10,111,687 B2 | 10/2018 | Lee-Sepsick |
| 10,172,643 B2 | 1/2019 | Lee-Sepsick et al. |
| 2001/0016738 A1 | 8/2001 | Harrington et al. |
| 2001/0016739 A1 | 8/2001 | Goldman et al. |
| 2001/0023365 A1 | 9/2001 | Medhkour et al. |
| 2001/0041900 A1 | 11/2001 | Callister et al. |
| 2002/0013589 A1 | 1/2002 | Callister et al. |
| 2002/0020417 A1 | 2/2002 | Nikolchev et al. |
| 2002/0029051 A1 | 3/2002 | Callister et al. |
| 2002/0035101 A1 | 3/2002 | Dey et al. |
| 2002/0072744 A1 | 6/2002 | Harrington et al. |
| 2002/0082636 A1 | 6/2002 | Sawhney et al. |
| 2002/0095082 A1 | 7/2002 | Evans et al. |
| 2002/0106411 A1 | 8/2002 | Wironen et al. |
| 2002/0133140 A1 | 9/2002 | Moulis |
| 2002/0148476 A1 | 10/2002 | Farley et al. |
| 2002/0176893 A1 | 11/2002 | Wironen et al. |
| 2002/0177846 A1 | 11/2002 | Mulier et al. |
| 2002/0177855 A1 | 11/2002 | Greene, Jr. et al. |
| 2003/0015203 A1 | 1/2003 | Makower et al. |
| 2003/0029457 A1 | 2/2003 | Callister et al. |
| 2003/0051735 A1 | 3/2003 | Pavcnik et al. |
| 2003/0060800 A1 | 3/2003 | Ryan |
| 2003/0066533 A1 | 4/2003 | Loy |
| 2003/0082636 A1 | 5/2003 | Wong |
| 2003/0108586 A1 | 6/2003 | Ramey |
| 2003/0134032 A1 | 7/2003 | Chaouk et al. |
| 2003/0158563 A1 | 8/2003 | McClellan et al. |
| 2003/0170173 A1 | 9/2003 | Klaveness et al. |
| 2003/0171759 A1 | 9/2003 | Sadler et al. |
| 2003/0185896 A1 | 10/2003 | Buiser et al. |
| 2003/0194389 A1 | 10/2003 | Porter |
| 2003/0194390 A1 | 10/2003 | Krall et al. |
| 2003/0223956 A1 | 12/2003 | Goupil et al. |
| 2004/0002680 A1 | 1/2004 | Ackerman et al. |
| 2004/0079377 A1 | 4/2004 | Nikolchev et al. |
| 2004/0127918 A1 | 7/2004 | Nikolchev et al. |
| 2004/0159324 A1 | 8/2004 | Nikolchev et al. |
| 2004/0161384 A1 | 8/2004 | Wheatley et al. |
| 2004/0163650 A1 | 8/2004 | Lowe et al. |
| 2004/0204720 A1 | 10/2004 | Harrington et al. |
| 2004/0206358 A1 | 10/2004 | Nikolchev et al. |
| 2004/0211429 A1 | 10/2004 | Nikolchev et al. |
| 2004/0215215 A1 | 10/2004 | McClellan et al. |
| 2004/0241874 A1 | 12/2004 | Abdel-Rehim |
| 2004/0258761 A1 | 12/2004 | Wheatley et al. |
| 2004/0258769 A1 | 12/2004 | Barker et al. |
| 2005/0045183 A1 | 3/2005 | Callister et al. |
| 2005/0149100 A1 | 7/2005 | Foltz |
| 2005/0240211 A1 | 10/2005 | Sporri et al. |
| 2006/0178620 A1 | 8/2006 | Wollmann et al. |
| 2008/0063603 A1 | 3/2008 | Schneider et al. |
| 2008/0264865 A1 | 10/2008 | Herman |
| 2009/0076573 A1 | 3/2009 | Burnett |
| 2009/0306623 A1 | 12/2009 | McIntosh et al. |
| 2011/0137150 A1 | 6/2011 | Connor et al. |
| 2011/0190572 A1 | 8/2011 | Brophy |

FOREIGN PATENT DOCUMENTS

| | | |
|---|---|---|
| CA | 2817296 | 11/2011 |
| CA | 2817330 | 11/2011 |
| CA | 2556747 | 7/2013 |
| CN | 200580006068.X | 4/2011 |
| CN | 2011035992.2 | 11/2011 |
| CN | 201810335624.7 | 11/2011 |
| DE | 2537620 | 2/1977 |
| DE | 3324754 | 7/1983 |
| DE | 1722732 | 3/2013 |
| EP | 05723981.6 | 2/2005 |
| EP | 09793278.4 | 10/2009 |
| EP | 11839530 | 11/2011 |
| EP | 11839693.6 | 11/2011 |
| EP | 17154076.8 | 11/2011 |
| EP | 13155297.8 | 2/2013 |
| EP | 1722732 | 3/2013 |
| FR | 2414925 | 8/1979 |
| GB | 1470571 | 4/1977 |
| GB | 1722732 | 3/2013 |
| HK | 07105332.9 | 2/2005 |
| HK | 1098042 A | 7/2007 |
| HK | 12103016.0 | 10/2009 |
| HK | 13100111.9 | 11/2011 |
| HK | 18114378.6 | 11/2011 |
| HK | 17113346.5 | 12/2017 |
| IE | 1722732 | 3/2013 |
| IN | 2536/KOLNP/06 | 2/2005 |
| IN | 5058DELNP/2013 | 11/2011 |
| JP | 59-046500 | 3/1984 |
| JP | 2002-200176 | 1/2002 |
| JP | 2007-500782 | 2/2005 |
| JP | 4750782 | 5/2011 |
| JP | 2011-245163 | 11/2011 |
| JP | 2013-538863 | 11/2011 |
| KR | 2013-7014341 | 11/2011 |
| WO | WO 1981/000701 | 3/1981 |
| WO | WO 1988/009648 | 12/1988 |
| WO | WO 1993/014786 | 8/1993 |
| WO | WO 1994/024944 | 11/1994 |
| WO | WO 1994/028803 | 12/1994 |
| WO | WO 1995/019184 | 7/1995 |
| WO | WO 1995/025490 | 9/1995 |
| WO | WO 1997/012569 | 4/1997 |
| WO | WO 1997/042987 | 11/1997 |
| WO | WO 1997/049345 | 12/1997 |
| WO | WO 1998/026737 | 6/1998 |
| WO | WO 1998/031308 | 7/1998 |
| WO | WO 1999/007297 | 2/1999 |
| WO | WO 1999/047073 | 9/1999 |
| WO | WO 2000/018469 | 4/2000 |
| WO | WO 2000/024374 | 5/2000 |
| WO | WO 2000/044323 | 8/2000 |
| WO | WO 2000/054746 | 9/2000 |
| WO | WO 2001/037760 | 5/2001 |
| WO | WO 2002/039880 | 5/2002 |
| WO | WO 2002/047744 | 6/2002 |
| WO | WO 2003/070085 | 3/2003 |
| WO | WO 2004/024237 | 3/2004 |
| WO | WO 2004/035022 | 4/2004 |
| WO | WO 2005/082299 | 9/2005 |
| WO | PCT/US2009/05937 | 10/2009 |
| WO | PCT/US2011/060013 | 11/2011 |
| WO | PCT/US2011/060049 | 11/2011 |

OTHER PUBLICATIONS

Office Action, issued Jun. 25, 2019, for IN Application No. 5058DELNP/2013, filed Nov. 9, 2019, (Lee-Sepsick et al.—Inventors) (6 pages).

Office Action, issued Jun. 20, 2019, for CA Application No. 2817296, filed Nov. 9, 2019,(Lee-Sepsick et al.—inventors) (3 pages).

Issue Notification, issued Oct. 10, 2020, for BR Application No. 1120130114347, filed Nov. 9, 2011, (Lee-Sepsick et al.—inventors) (1 page).

Office Action, issued Jul. 7, 2020, for CA Application No. 2817296, filed Nov. 9, 2019, (Lee-Sepsick et al.—inventors) (4 pages).

Final Fee, issued Jun. 3, 2021, for CA Application No. 2817296, filed Nov. 9, 2019,(Lee-Sepsick et al.—inventors) (3 pages).

First Office Action, issued May 28, 2020, for CN Application No. 201810335624.7, filed Nov. 9, 2019 (Lee-Sepsick et al.—Inventors) (8 pages).

Second Office Action, issued Mar. 1, 2021, for CN Application No. 201810335624.7, filed Nov. 9, 2019 (Lee-Sepsick et al.—inventors) (5 pages).

Notice of Allowance, issued Aug. 2, 2021, for CN Application No. 201810335624.7, filed Nov. 9, 2019 (Lee-Sepsick et al.—inventors) (2 pages).

Preliminary Amendment, issued Feb. 22, 2019, for U.S. Appl. No. 16/283,091, filed Feb. 22, 2019 (Lee-Sepsick et al.—inventors) (6 pages).

(56) References Cited

OTHER PUBLICATIONS

Corrected Preliminary Amendment, issued Feb. 22, 2019, for U.S. Appl. No. 16/283,091, filed Feb. 22, 2019 (Lee-Sepsick et al.—inventors) (6 pages).
NonFinal Office Action, issued Mar. 26, 2021, for U.S. Appl. No. 16/283,091, filed Feb. 22, 2019 (Lee-Sepsick et al.—inventors) (7 pages).
Response to NonFinal Office Action, issued Jun. 24, 2021, for U.S. Appl. No. 16/283,091, filed Feb. 22, 2019 (Lee-Sepsick et al.—inventors) (11 pages).
Notice of Allowance, issued Jul. 16, 2021, for U.S. Appl. No. 16/283,091, filed Feb. 22, 2019 (Lee-Sepsick et al.—inventors) (5 pages).
Corrected Notice of Allowance, issued Jul. 22, 2021, for U.S. Appl. No. 16/283,091, filed Feb. 22, 2019 (Lee-Sepsick et al.—inventors) (2 pages).
Corrected Notice of Allowance, issued Aug. 4, 2021, for U.S. Appl. No. 16/283,091, filed Feb. 22, 2019 (Lee-Sepsick et al.—inventors) (2 pages).
First Notice of Allowance, issued May 15, 2018, for Canadian patent application No. 2817330, filed Nov. 9, 2011, Applicant: Femasys Inc.; (4 pages).
Second Notice of Allowance, issued Jan. 3, 2019, for Canadian patent application No. 2817330, filed Nov. 9, 2011, Applicant: Femasys Inc.; (1 pages).
Final Office Action, issued Nov. 14, 2019, in U.S. Appl. No. 13/292,990, filed Sep. 11, 2011, Applicant Femasys Inc., 18 p.
Response to Final Office Action, issued Feb. 14, 2020, in U.S. Appl. No. 13/292,990, filed Sep. 11, 2011, Applicant Femasys Inc., 7 p.
NonFinal Office Action, issued Mar. 17, 2020, in U.S. Appl. No. 13/292,990, filed Sep. 11, 2011, Applicant Femasys Inc., 11 p.
Response to NonFinal Office Action, issued Apr. 10, 2020, in U.S. Appl. No. 13/292,990, filed Sep. 11, 2011, Applicant Femasys Inc., 11 p.
Notice of Allowance, issued Apr. 21, 2020, in U.S. Appl. No. 13/292,990, filed Sep. 11, 2011, Applicant Femasys Inc., 9 p.
Decision to Grant, issued Sep. 17, 2020, in EP Application No. 11839530.0, filed Nov. 9, 2011, Applicant Femasys Inc., 2 p.
Summons to Oral Proceedings, issued Feb. 1, 2020, in EP Application No. 11839530.0, filed Nov. 9, 2011, Applicant Femasys Inc., 8 p.
Communication, issued Nov. 21, 2017, in EP Application No. 11839530.0, filed Nov. 9, 2011, Applicant Femasys Inc., 6 p.
Notice of Allowance, issued Feb. 14, 2019, in KR Application No. 10-2013-7014341, filed Nov. 9, 2011, Applicant Femasys Inc., 3 p.
Preliminary Amendment, issued Aug. 21, 2021, in U.S. Appl. No. 17/408,392, filed Aug. 21, 2021, Applicant Femasys Inc., 9 p.
NonFinal Office Action, issued Sep. 14, 2022, in U.S. Appl. No. 17/408,392, filed Aug. 21, 2021, Applicant Femasys Inc., 8 p.
Response to NonFinal Office Action, issued Jan. 4, 2023, in U.S. Appl. No. 17/408,392, filed Aug. 21, 2021, Applicant Femasys Inc., 12 p.
Preliminary Amendment, issued Jun. 16, 2020, in U.S. Appl. No. 16/902,837, filed Jun. 16, 2020, Applicant Femasys Inc., 7 p.
NonFinal Office Action, issued Mar. 29, 2022, in U.S. Appl. No. 16/902,837, filed Jun. 16, 2020, Applicant Femasys Inc., 10 p.
Response to NonFinal Office Action, issued Jun. 29, 2022, in U.S. Appl. No. 16/902,837, filed Jun. 16, 2020, Applicant Femasys Inc., 10 p.
Notice of Allowance, issued Sep. 23, 2022, in U.S. Appl. No. 16/902,837, filed Jun. 16, 2020, Applicant Femasys Inc., 7 p.
U.S. Appl. No. 12/245,265, filed Oct. 3, 2008, Kathy Lee-Sepsick.
U.S. Appl. No. 16/043,996, filed Jul. 24, 2018, Kathy Lee-Sepsick.
U.S. Appl. No. 16/283,091, filed Feb. 22, 2019, Kathy Lee-Sepsick.
U.S. Appl. No. 17/408,392, filed Aug. 21, 2021, Kathy Lee-Sepsick.
U.S. Appl. No. 18/131,174, filed Apr. 5, 2023, Kathy Lee-Sepsick.
U.S. Appl. No. 13/219,667, filed Aug. 27, 2011, Kathy Lee-Sepsick.
U.S. Appl. No. 15/404,887, filed Jan. 12, 2017, Kathy Lee-Sepsick.
U.S. Appl. No. 16/186,553, filed Nov. 11, 2018, Kathy Lee-Sepsick.
U.S. Appl. No. 18/133,721, filed Apr. 12, 2023, Kathy Lee-Sepsick.
U.S. Appl. No. 61/411,856, filed Nov. 9, 2010, Kathy Lee-Sepsick.
U.S. Appl. No. 13/292,990 filed Nov. 9, 2011, Kathy Lee-Sepsick.
U.S. Appl. No. 16/902,837, filed Jun. 16, 2020, Lee-Sepsick, Kathy.
U.S. Appl. No. 18/086,277, filed Dec. 21, 2022, Lee-Sepsick, Kathy.
El-Mowafi DM, et al. (2008) Fallopian Tube. Geneva Foundation for Medical Education and Research. (8 pages) Download available at: http://www.gfmer.ch/International_activities_En/El_Mowafi/Fallopian_tube.htm.
Keller MW, et al. (1986) Automated production and analysis of echo contrast agents. J Ultrasound Med. 5(9): 493-498.
Abdala N, et al. (2001). Use of ethylene vinyl alcohol copolymer for tubal sterilization by selective catheterization in rabbits. J Vasc Interv Radiol. 12(8): 979-984.
Abma JC, et al. (1997) Fertility, family planning, and women's health: new data from the 1995 National Survey of Family Growth. Vital Health Stat 23. (19): 1-114.
American Foundation for Urologic Disease. (2005) Facts about vasectomy safety. Published by the National Institute of Child Health & Human Development. Retrieved on Jun. 29, 2005 from the world wide web at http://www.nichd.nih.gov/publications/pubs/vasect.htm.
ApSimon HT, et al. (1984) Embolization of small vessels with a double-lumen microballoon catheter. Part I: Design and construction. Radiology. 151(1): 55-57.
Assaf A, et al. (1993) Histopathological effects of silicone rubber 'Ovabloc' on the human fallopian tube. Int J Gynaecol Obstet. 43(2): 181-189.
Basu S, et al. (1995) Comparative study of biological glues: cryoprecipitate glue, two-component fibrin sealant, and "French" glue. Ann Thorac Surg. 60(5): 1255-1262.
Berkey GS, et al. (1995) Sterilization with methyl cyanoacrylate-induced fallopian tube occlusion from a nonsurgical transvaginal approach in rabbits. J Vasc Interv Radiol. 6(5): 669-674.
Brundin J, et al. (1985) Long-term toxicity of a hydrogelic occlusive device in the isthmus of the human oviduct. A light microscopic study. Acta Pathol Microbiol Immunol Scand A. 93(3): 121-126.
Brundin J. (1991) Transcervical sterilization in the human female by hysteroscopic application of hydrogelic occlusive devices into the intramural parts of the fallopian tubes: 10 years experience of the P-block. Eur J Obstet Gynecol Reprod Biol. 39(1): 41-49.
Canavan TP. (1998) Appropriate use of the intrauterine device. Am Fam Physician. 58(9): 2077-2084, 2087-2088.
Chen FQ. (1989) Study on the transperitoneal sterilization of the fallopian tube with silicon rubber plug and its reversibility. Shengzhi Yu Biyun. 9(3): 51-54.
Clenney TL, et al. (1999) Vasectomy techniques. Am Fam Physician. 60(1): 137-146, 151-152.
Cooper JM. (1992) Hysteroscopic sterilization. Clin Obstet Gynecol. 35(2): 282-298.
Dan SJ, et al. (1984) Fallopian tube occlusion with silicone: radiographic appearance. Radiology. 151(3): 603-605.
Davis RH, et al. (1975) Fallopian tube occlusion in rabbits with silicone rubber. J Reprod Med. 14(2): 56-61.
Davis RH, et al. (1979) Chronic occlusion of the monkey fallopian tube with silicone polymer. Obstet Gynecol. 53(4): 527-529.
Davis RH, et al. (1979) Chronic occlusion of the rabbit Fallopian tube with silicone polymer. Gynecol Obstet Invest. 10(6): 281-288.
Erb RA, et al. (1979) Hysteroscopic oviductal blocking with formed-in-place silicone rubber plugs. I. Method and apparatus. J Reprod Med. 23(2): 65-68.
Farcon E, et al. (1975) An absorbable intravasal stent and a silicone intravasal reversible plug. Report of experiments on animals. Invest Urol. 13(2): 108-112.
Fischer ME, et al. (1984) Silicone devices for tubal occlusion: radiographic description and evaluation. Radiology. 151(3): 601-602.
Frydman R. (2000) A double-blind, randomized study to compare recombinant humna follicle stimulating hormone (FSH: Gonal-F) with highly purified urinary FSH (Metrodin HP) in women undergoing assisted reproductive techniques including intracytoiplasmic sperm injection. Human Reproduction. 15(3): 520-525.

(56) References Cited

OTHER PUBLICATIONS

Grode GA, et al. (1971) Feasibility study on the use of a tissue adhesive for the nonsurgical blocking of fallopian tubes. Phase I: evaluation of a tissue adhesive. Fertil Steril. 22(9): 552-555.
Harrell WB, et al. (1969) Simulated tuboplasty using tissue adhesive on uterine horn in canines. J Ark Med Soc. 65(11): 433-435.
Hefnawi F, et al. (1967) Control of fertility by temporary occlusion of the oviduct. Am J Obstet Gynecol. 99(3): 421-427.
Hendrix NW, et al. (1999). Sterilization and its consequences. Obstet Gynecol Surv. 54(12): 766-777.
Holt VL, et al. (2003) Oral contraceptives, tubal sterilization, and functional ovarian cyst risk. Obstet Gynecol. 102(2): 252-258.
Huvar I, et al. (1994) Hysteroscopic sterilization using Ovabloc. Ceska Gynekol. 59(4): 193-195.
Jamieson DJ, et al. (2002) A comparison of women's regret after vasectomy versus tubal sterilization. Obstet Gynecol. 99(6): 1073-1079.
Libenzon LL, et al. (1973) Contraception through the sealing off of Fallopian tubes (experimental studies). Eksp Khir Anesteziol. 18(5): 18-20.
Loffer FD, et al. (1986) Learning hysteroscopy sterilization and the Ovabloc System with Hyskon. Acta Eur Fertil. 17(6): 477-480.
Loffer FD. (1982) What's new in female sterilization? The silicone tubal plug is. Ariz Med. 39(7): 442-445.
Loffer FD. (1984) Hysteroscopic sterilization with the use of formed-in-place silicone plugs. Am J Obstet Gynecol. 149(3): 261-270.
Maubon AJ, et al. (1996) Tubal sterilization by means of selective catheterization: comparison of a hydrogel and a collagen glue. J Vasc Interv Radiol. 7(5): 733-736.
Neuwirth RS, et al. (1971) Chemical induction of tubal blockade in the monkey. Obstet Gynecol. 38(1): 51-54.
Neuwirth RS, et al. (1980) An outpatient approach to female sterilization with methylcyanoacrylate. Am J Obstet Gynecol. 136(7): 951-956.
Neuwirth RS, et al. (1983) Trials with the FEMCEPT method of female sterilization and experience with radiopaque methylcyanoacrylate. Am J Obstet Gynecol. 145(8): 948-954.
No authors listed. (1973) Animal studies show silicone plugs prevent conception. JAMA. 225(2): 105-106.
No authors listed. (1973) Implants seen as reversible contraceptives. Biomed News. 4: 12.
No authors listed. (Apr. 1994) Hysteroscopy. ACOG Technical Bulletin No. Int J Gynaecol Obstet. 45(2): 175-180.
Omran KF, et al. (1970) Tubal occlusion: a comparative study. Int J Fertil. 15(4): 226-241.
Pelage JP, et al. (1998) Selective salpingography and fallopian tubal occlusion with n-butyl-2-cyanoacrylate: report of two cases. Radiology. 207(3): 809-812.
Pollack A. (2003) ACOG practice bulletin. Clinical management guidelines for obstetrician-gynecologists. Obstet Gynecol. 102(3): 647-658.
Rakshit B. (1970) Attempts at chemical blocking of the Fallopian tube for female sterilization. J Obstet Gynaecol India. 20: 618-624.
Reed TP et al. (1980) Tubal occlusion with silicone rubber: an update. J Reprod Med. 25(1): 25-28.
Reed TP, et al. (1983) Hysteroscopic tubal occlusion with silicone rubber. Obstet Gynecol. 61(3): 388-392.
Reed TP, et al. (Nov. 1978) Hysteroscopic Oviductal Blocking with Formed-In-Place Silicone Rubber Plugs Clinical Studies. Paper presented at the Clinical Symposium on Gynecologic Endoscopy. $7^{th}$ Annual Meeting (Hollywood, FL) (pp. 1-4).
Richart RM. (1981) Female sterilization using chemical agents. Res Front Fertil Regul. 1(5): 1-12.
Richman TS, et al. (1984) Fallopian tubal patency assessed by ultrasound following fluid injection. Radiology. 152(2): 507-510.
Risquez F. (1990) Diagnosis and treatment of ectopic pregnancy by retrogrande selective salpingography and intraluminal methotrexate injection: work in progress. Human Reproduction. 5(6): 759-762.

Saito H, et al. (2007) pH-responsive swelling behavior of collagen gels prepared by novel crosslinkers based on naturally derived di- or tricarboxylic acids. Acta Biomater. 3(1): 89-94.
Snider S. (1990). The Pill: 30 years of Safety Concerns. Published by the U.S. Food and Drug Administration. (6 pages).
Steptoe PC. (1975) Advances in laparoscopic sterilisation techniques. S Afr Med J. 49(48): 2019-2021.
Stevenson TC, et al. (1972) The effect of methyl cyanoacrylate tissue adhesive on the human Fallopian tube and endometrium. J Obstet Gynaecol Br Commonw. 79(11): 1028-1039.
Su YK. (1991) Embolus formation using bismuth polyurethane for tubosterilization observation of 259 cases. Zhonghua Fu Chan Ke Za Zhi. 26(6): 352-354, 388.
United Nations Secretariat. (2003) Fertility, Contraception and population policies. United Nations Population Division, Department of Economic and Social Affairs. ESA/P/WP.182 (42 pages).
Van der Leij G, et al. (1995) Impact of Ovabloc intratubal polymer on the morphology of the fallopian tube. Int J Gynecol Pathol. 14(2): 167-173.
Van der Leij G, et al. (1997) Radiographic aspects of office hysteroscopic tubal occlusion with siloxane intratubal devices (the Ovabloc method). Int J Gynaecol Obstet. 59(2): 123-131.
Viddya Medical News Service. (2000) Bibliography Excerpts: Side effects of tubal ligation sterilizations. 1: 249. (5 pages).
Volpi E, et al. (1996). Transvaginal sonographic tubal patency testing using air and saline solution as contrast media in a routine infertility clinic setting. Ultrasound Obstet Gynecol. 7(1): 43-48.
Wilson EW. (1995) The evolution of methods for female sterilization. Int J Gynaecol Obstet. 51 Suppl 1: S3-13.
Request Examination issued Nov. 7, 2014 for Japanese Patent Application No. 2011-245163 which claims priority to PCT/US2011/060013 filed Nov. 9, 2011 (Lee-Sepsick et al.—inventors; Femasys, Inc.—Applicant) (1 Page).
Office Action issued Oct. 13, 2015 for Japanese Patent Application No. 2011-245163 which claims priority to PCT/US2011/060013 filed Nov. 9, 2011 (Lee-Sepsick et al.—inventors; Femasys, Inc.—Applicant) (2 Pages).
Office Action issued Feb. 2, 2016 for Japanese Patent Application No. 2011-245163 which claims priority to PCT/US2011/060013 filed Nov. 9, 2011 (Lee-Sepsick et al.—inventors; Femasys, Inc.—Applicant) (2 Pages).
Response to NonFinal Office Action, issued Dec. 21, 2016, for U.S. Appl. No. 12/245,265, filed Oct. 3, 2008 (Lee—Sepsick et al.—inventors) (11 pages).
Final Office Action, issued Mar. 17, 2017 for U.S. Appl. No. 12/245,265, filed Oct. 3, 2008 (Lee-Sepsick et al.—Inventors) (20 pages).
Response to Final Office Action, issued Jun. 19, 2017, for U.S. Appl. No. 12/245,265, filed Oct. 3, 2008 (Lee-Sepsick et al.—inventors) (17 pages).
Final Office Action, issued Sep. 21, 2017, for U.S. Appl. No. 12/245,265, filed Oct. 3, 2008 (Lee-Sepsick et al.—Inventors) (17 pages).
Response to Final Office Action, issued Jan. 22, 2018, for U.S. Appl. No. 12/245,265, filed Oct. 3, 2008 (Lee-Sepsick et al.—inventors) (17 pages).
Nonfinal Office Action, issued Oct. 22, 2018, for U.S. Appl. No. 12/245,265, filed Oct. 3, 2008 (Lee-Sepsick et al.—Inventors) (7 pages).
Response to NonFinal Office Action, issued Mar. 23, 2018, for U.S. Appl. No. 12/245,265, filed Oct. 3, 2008 (Lee-Sepsick et al.—inventors) (10 pages).
Notice of Allowance, issued May 10, 2018, for U.S. Appl. No. 12/245,265, filed Oct. 3, 2008 (Lee-Sepsick et al.—Inventors) (11 pages).
Issue Fee Payment, issued Aug. 3, 2018, for U.S. Appl. No. 12/245,265, filed Oct. 3, 2008 (Lee-Sepsick et al.—Inventors) (2 pages).
Filing Receipt, issued Aug. 9, 2018, for U.S. Appl. No. 16/043,996, filed Jul. 24, 2018 (Lee-Sepsick et al.—inventors) (3 pages).
Issue Notification issued Jan. 11, 2017 for U.S. Appl. No. 13/219,867, filed Aug. 27, 2011 (Lee-Sepsick et al.—inventors 1 page).

(56) References Cited

OTHER PUBLICATIONS

Response to 312 Amendment issued Nov. 2, 2016 for U.S. Appl. No. 13/219,867, filed Aug. 27, 2011 (Lee-Sepsick et al.—inventors) (2 pages).
312 Amendment issued Oct. 27, 2016 for U.S. Appl. No. 13/219,867, filed Aug. 27, 2011 (Lee-Sepsick et al.—inventors) 4 pages).
Notice of Allowance issued Sep. 19, 2016 for U.S. Appl. No. 13/219,867, filed Aug. 27, 2011 (Lee-Sepsick et al.—Inventors) (10 pages).
Response to Final Office Action issued Sep. 2, 2016 for U.S. Appl. No. 13/219,867, filed Aug. 27, 2011 (Lee-Sepsick et al.—inventors) (17 pages).
Final Office Action issued Jun. 9, 2016 for U.S. Appl. No. 13/219,867, filed Aug. 27, 2011 (Lee-Sepsick et al.—inventors) (20 pages).
Response to Non-Final Office Action issued Mar. 10, 2016 for U.S. Appl. No. 13/219,867, filed Nov. 9, 2011 (Lee-Sepsick et al.—inventors) (10 pages).
NonFInal Office Action, issued Mar. 27, 2013 for U.S. Appl. No. 13/292,990, filed Aug. 27, 2011 (Lee-Sepsick et al.—inventors) (10 pages).
Response to NonFinal Office Action, issued Aug. 27, 2013 for U.S. Appl. No. 13/292,990, filed Aug. 27, 2011 (Lee-Sepsick et al.—inventors) (11 pages).
Final Office Action, issued Sep. 12, 2013 for U.S. Appl. No. 13/292,990, filed Aug. 27, 2011 (Lee-Sepsick et al.—inventors) (10 pages).
Response to Final Office Action, issued Dec. 12, 2013 for U.S. Appl. No. 13/292,990, filed Aug. 27, 2011 (Lee-Sepsick et al.—inventors) (15 pages).
NonFInal Office Action, issued Sep. 18, 2014 for U.S. Appl. No. 13/292,990, filed Aug. 27, 2011 (Lee-Sepsick et al.—inventors) (11 pages).
Response to NonFinal Office Action, issued Mar. 18, 2015 for U.S. Appl. No. 13/292,990, filed Aug. 27, 2011 (Lee-Sepsick et al.—inventors) (12 pages).
Final Office Action, issued Jul. 16, 2015 for U.S. Appl. No. 13/292,990, filed Aug. 27, 2011 (Lee-Sepsick et al.—inventors) (14 pages).
Response to Final Office Action, issued Oct. 16, 2015 for U.S. Appl. No. 13/292,990, filed Aug. 27, 2011 (Lee-Sepsick et al.—inventors) (14 pages).
Response to Final Office Action and RCE, issued Nov. 16, 2015 for U.S. Appl. No. 13/292,990, filed Aug. 27, 2011 (Lee-Sepsick et al.—inventors) (16 pages).
NonFinal Office Action, issued Apr. 21, 2016 for U.S. Appl. No. 13/292,990, filed Aug. 27, 2011 (Lee-Sepsick et al.—inventors) (15 pages).
Response to NonFinal Office Action, issued Aug. 22, 2016 for U.S. Appl. No. 13/292,990, filed Aug. 27, 2011 (Lee-Sepsick et al.—inventors) (14 pages).
Final Office Action, issued Dec. 9, 2016 for U.S. Appl. No. 13/292,990, filed Aug. 27, 2011 (Lee-Sepsick et al.—inventors) (17pages).
Response to Final Office Action, issued Feb. 9, 2017 for U.S. Appl. No. 13/292,990, filed Aug. 27, 2011 (Lee-Sepsick et al.—inventors) (15 pages).
Advisory Action, issued Mar. 20, 2017 for U.S. Appl. No. 13/292,990, filed Aug. 27, 2011 (Lee-Sepsick et al.—inventors) (5 pages).
Response to Final Office Action and RCE, issued May 9, 2017 for U.S. Appl. No. 13/292,990, filed Aug. 27, 2011 (Lee-Sepsick et al.—inventors) (16 pages).
NonFinal Office Action, issued Oct. 5, 2017 for U.S. Appl. No. 13/292,990, filed Aug. 27, 2011 (Lee-Sepsick et al.—inventors) (14 pages).
Response to NonFinal Office Action, issued Feb. 5, 2018 for U.S. Appl. No. 13/292,990, filed Aug. 27, 2011 (Lee-Sepsick et al.—inventors) (16 pages).

Examination Report issued Oct. 28, 2016 for Canadian Patent Application No. 2770504 which claims priority to PCT/US2009/05937 filed Oct. 2, 2009 (Lee-Sepsick et al.—inventors; Femasys, Inc.—Applicant) (3 Pages).
Patent Grant Notice issued Mar. 6, 2018 for Canadian Patent Application No. 2770504 which claims priority to PCT/US2009/05937 filed Oct. 2, 2009 (Lee-Sepsick et al.—inventors; Femasys, Inc.—Applicant) (1 Page).
Request for Examination issued Oct. 24, 2016 for Canadian Patent Application No. 2817296 which claims priority to PCT/US2011/060013 filed Nov. 9, 2011 (Lee-Sepsick et al.—inventors; Femasys, Inc.—Applicant) (1 Page).
Examination Report issued Aug. 9, 2017 for Canadian Patent Application No. 2817296 which claims priority to PCT/US2011/060013 filed Nov. 9, 2011 (Lee-Sepsick et al.—inventors; Femasys, Inc.—Applicant) (4 Pages).
Examination Report issued Jul. 26, 2018 for Canadian Patent Application No. 2817296 which claims priority to PCT/US2011/060013 filed Nov. 9, 2011 (Lee-Sepsick et al.—inventors; Femasys, Inc.—Applicant) (3 Pages).
Examination Report issued May 24, 2017 for European Patent Application No. 09793278.4 which claims priority to PCT/US2009/05937 filed Oct. 2, 2009 (Lee-Sepsick et al.—inventors; Femasys, Inc.—Applicant) (4 Pages).
Intention to Grant issued Jan. 11, 2018 for European Patent Application No. 09793278.4 which claims priority to PCT/US2009/05937 filed Oct. 2, 2009 (Lee-Sepsick et al.—inventors; Femasys, Inc.—Applicant) (5 Pages).
Communication issued Nov. 21, 2017 for European Patent Application No. 11839530.0 which claims priority to PCT/US2011/060013 filed Nov. 9, 2011 (Lee-Sepsick et al.—inventors; Femasys, Inc.—Applicant) (6 Pages).
Supplemental Search and Opinion issued Oct. 17, 2014 for European Patent Application No. 11839530.0 which claims priority to PCT/US2011/060013 filed Nov. 9, 2011 (Lee-Sepsick et al.—inventors; Femasys, Inc.—Applicant) (11 Pages).
Request for Examination issued Oct. 11, 2014 for Brazilian Patent Application No. BR1120130114347 which claims priority to PCT/US2011/060013 filed Nov. 9, 2011 (Lee-Sepsick et al.—inventors; Femasys, Inc.—Applicant) (1 Page).
Office Action issued Jul. 31, 2014 for Chinese Patent Application No. 2011035992.2 which claims priority to PCT/US2011/060013 filed Nov. 9, 2011 (Lee-Sepsick et al.—inventors; Femasys, Inc.—Applicant) (11 Pages).
Office Action issued Jun. 3, 2015 for Chinese Patent Application No. 2011035992.2 which claims priority to PCT/US2011/060013 filed Nov. 9, 2011 (Lee-Sepsick et al.—inventors; Femasys, Inc.—Applicant) (8 Pages).
Reexamination Decision, issued Jun. 3, 2015 for Chinese Patent Application No. 2011035992.2 which claims priority to PCT/US2011/060013 filed Nov. 9, 2011 (Lee-Sepsick et al.—inventors; Femasys, Inc.—Applicant) (8 Pages).
Decision to Grant issued Oct. 26, 2016 for Japanese Patent Application No. 2011-245163 which claims priority to PCT/US2011/060013 filed Nov. 9, 2011 (Lee-Sepsick et al.—inventors; Femasys, Inc.—Applicant) ( 4 Pages).
Request for Examination issued Nov. 5, 2014 for Indian Patent Application No. 5058DELNP/2013 which claims priority to PCT/US2011/060013 filed Nov. 9, 2011 (Lee-Sepsick et al.—inventors; Femasys, Inc.—Applicant) (1 Page).
Request for Examination, issued Oct. 26, 2016, for Korean Patent Application No. 2013-7014341, which claims priority to PCT/US2011/060013 filed Nov. 9, 2011 (Lee-Sepsick et al.—inventors; Femasys, Inc.—Applicant) (2 Pages).
First Office Action, Issued Jan. 22, 2018, for Korean Patent Application No. 2013-7014341, which claims priority to PCT/US2011/060013 filed Nov. 9, 2011 (Lee-Sepsick et al.—inventors; Femasys, Inc.—Applicant) (7 Pages).
Second Office Action, issued Jul. 31, 2018, for Korean Patent Application No. 2013-7014341, which claims priority to PCT/US2011/060013 filed Nov. 9, 2011 (Lee-Sepsick et al.—inventors; Femasys, Inc.—Applicant) (2 Pages).

(56) References Cited

OTHER PUBLICATIONS

Request for Examination issued Oct. 24, 2016 for Canadian Patent Application No. 2817330 which claims priority to PCT/US2011060049 filed Nov. 9, 2011 (Lee-Sepsick et al.—inventors; Femasys, Inc.—Applicant) (1 Page).
Office Action, issued Sep. 6, 2017 for Canadian Patent Application No. 2817330 which claims priority to PCT/US2011060049 filed Nov. 9, 2011 (Lee-Sepsick et al.—inventors; Femasys, Inc.—Applicant) (4 Page).
Decision to Grant issued Jan. 5, 2017 for European Patent Application No. 11839693.6 which claims priority to PCT/US2011/060049 filed Nov. 9, 2011 (Lee-Sepsick et al.—inventors; Femasys, Inc.—Applicant) (2 Pages).
Intention to Grant Communication, issued Aug. 8, 2016 for European Patent Application No. 11839693.6 which claims priority to PCT/US2011/060049 filed Nov. 9, 2011 (Lee-Sepsick et al.—inventors; Femasys, Inc.—Applicant) (5 Pages).
Communication pursuant to Article 94(3) EPC, issued Jun. 18, 2015 for European Patent Application No. 11839693.6 which claims priority to PCT/US2011/060049 filed Nov. 9, 2011 (Lee-Sepsick et al.—inventors; Femasys, Inc.—Applicant) (4 Pages).
Supplemental European Search Report, issued May 8, 2014 for European Patent Application No. 11839693.6 which claims priority to PCT/US2011/060049 filed Nov. 9, 2011 (Lee-Sepsick et al.—inventors; Femasys, Inc.—Applicant) (4 Pages).
Communication pursuant to Article 94(3) EPC, issued Jan. 3, 2018 for European Patent Application No. 17154076.8, divisional application of European Patent Application No. 11839693.6, which claims priority to PCT/US2011/060049 filed Nov. 9, 2011 (Lee-Sepsick et al.—inventors; Femasys, Inc.—Applicant) (4 Pages).
European Search and Opinion, issued May 2, 2017 for European Patent Application No. 17154076.8, divisional application of European Patent Application No. 11839693.6, which claims priority to PCT/US2011/060049 filed Nov. 9, 2011 (Lee-Sepsick et al.—inventors; Femasys, Inc.—Applicant) (5 Pages).
Office Action, issued Aug. 1, 2017 for Japanese Patent Application No. 2013-538863, which claims priority to PCT/US2011/060049 filed Nov. 9, 2011 (Lee-Sepsick et al.—inventors; Femasys, Inc.—Applicant) (1 Page).
Decision to Grant, issued Nov. 21, 2017 for Japanese Patent Application No. 2013-538863, which claims priority to PCT/US2011/060049 filed Nov. 9, 2011 (Lee-Sepsick et al.—inventors; Femasys, Inc.—Applicant) (4 Pages).
Official Action dated Aug. 9, 2017 for Canadian Application No. CA 2,817,296, which claims priority to PCT/US2011/060013 (Applicant—Femasys Inc.; Inventors—Lee-Sepsick et al.; 4 pgs.
Advisory Action issued May 24, 2012 for U.S. Appl. No. 12/245,265, filed Oct. 3, 2008 (Lee-Sepsick et al.—inventors) 3 pgs.
Final Office Action issued Feb. 3, 12 for U.S. Appl. No. 12/245,265, filed Oct. 3, 2008 (Lee-Sepsick et al.—inventors) 12 pgs.
Final Office Action issued Feb. 4, 2016 for U.S. Appl. No. 12/245,265, filed Oct. 3, 2008 (Lee-Sepsick et al.—inventors) 12 pgs.
Final Office Action, issued Feb. 14, 14 for U.S. Appl. No. 12/245,265, filed Oct. 3, 2008 (Lee-Sepsick et al.—inventors) 12 pgs.
NonFinal Office Action issued Jun. 24, 2011 for U.S. Appl. No. 12/245,265, filed Oct. 3, 2008 (Lee-Sepsick et al.—inventors) 11 pgs.
NonFinal Office Action issued Mar. 29, 13 for U.S. Appl. No. 12/245,265, filed Oct. 3, 2008 (Lee-Sepsick et al.—inventors) 11 pgs.
NonFinal Office Action, issued Jul. 23, 2015 for U.S. Appl. No. 12/245,265, filed Oct. 3, 2008 (Lee-Sepsick et al.—inventors) 10 pgs.
NonFinal Office Action, issued Sep. 21, 2016 for U.S. Appl. No. 12/245,265, filed Oct. 3, 2008 (Lee-Sepsick et al.—inventors) 14 pgs.
Response to Final Office Action, filed Jan. 12, 2015 for U.S. Appl. No. 12/245,265, filed Oct. 3, 2008 (Lee-Sepsick et al.—inventors).
Response to Final Office Action, filed May 3, 2012 for U.S. Appl. No. 12/245,265, filed Oct. 3, 2008 (Lee-Sepsick et al.—inventors).
Response to Final Office Action, filed Jul. 5, 2016, for U.S. Appl. No. 12/245,265, filed Oct. 3, 2008 (Lee-Sepsick et al.—inventors).
Response to NonFinal Office Action, filed Aug. 29, 2013, for U.S. Appl. No. 12/245,265, filed Oct. 3, 2008 (Lee-Sepsick et al.—inventors).
Response to NonFinal Office Action, Filed Sep. 26, 2011, for U.S. Appl. No. 12/245,265, filed Oct. 3, 2008 (Lee-Sepsick et al.—inventors).
Response to NonFinal Office Action, filed Nov. 23, 2015, for U.S. Appl. No. 12/245,265, filed Oct. 3, 2008 (Lee-Sepsick et al.—inventors).
Response, filed Oct. 3, 13, for U.S. Appl. No. 12/245,265, filed Oct. 3, 2008 (Lee-Sepsick et al.—inventors).
Response to NonFinal Office Action, filed Dec. 21, 2016, for U.S. Appl. No. 12/245,265, filed Oct. 3, 2008 (Lee-Sepsick et al.—inventors).
Response to Final Office Action, filed Jul. 3, 2012, for U.S. Appl. No. 12/245,265, filed Oct. 3, 2008 (Lee-Sepsick et al.—inventors).
Official Action issued Nov. 20, 2015 for Canadian Patent Application No. 2770504, (Lee-Sepsick et al.—inventors) 3 pgs.
Rejection Decision from SIPO issued Aug. 22, 2016 for Chinese Application No. 201110353992.2, (Lee-Sepsick et al.—inventors) 8 pgs.
Third Office Action from SIPO, issued Feb. 15, 2016, for Chinese Application No. 201110353992.2, (Lee-Sepsick et al.—inventors) 12 pgs.
NonFinal Office Action, issued Sep. 10, 15 for U.S. Appl. No. 113/219,667, filed Aug. 27, 2011 (Lee-Sepsick et al.—inventors) 11 pgs.
Final Office Action issued Sep. 3, 14 for U.S. Appl. No. 113/219,667, filed Aug. 27, 2011 (Lee-Sepsick et al.—inventors) 10 pgs.
NonFinal Office Action, issued May 8, 2014, for U.S. Appl. No. 113/219,667, filed Aug. 27, 2011 (Lee-Sepsick et al.—inventors) 13 pgs.
Communication under Rules 161(1) and 162 EPC, issued Aug. 4, 2011, for EP 09793278.4, claims priority to PCT/US2009/059370, filed Oct. 2, 2009, (Lee-Sepsick et al.—inventors) 2 pgs.
International Preliminary Report, issued Apr. 5, 2011 for PCT/US2009/059370, filed Oct. 2, 2009, (Lee-Sepsick et al.—inventors) 7 pgs.
International Search Report issued Jn. 22, 201 for PCT/US2009/059370, filed Oct. 2, 2009, (Lee-Sepsick et al.—inventors) 6 pgs.
Written Opinion, issued Jan. 22, 2010 for PCT/US2009/059370, filed Oct. 2, 2009, (Lee-Sepsick et al.—inventors) 6 pgs.
International Search Report and Written Opinion, issued Mar. 23, 2012, for PCT/US2011/060013, filed Nov. 9, 2011, (Lee- Sepsick et al.—inventors) 12 pgs.
IPRP, issued Mar. 13, 2012, for PCT/US2011/060013, filed Nov. 9, 2011, PCT/US2011/060049, filed Nov. 9, 2011, (Lee-Sepsick et al.—inventors) 7 pgs.
International Search Report and Written Opinion issued Feb. 29, 12 for PCT/US2011/060049, filed Nov. 9, 2011, (Lee-Sepsick et al.—inventors) 12 pgs.
IPRP, issued May 14, 2013 for PCT/US2011/060049, filed Nov. 9, 2011, (Lee-Sepsick et al.—inventors) 12 pgs.
Final Notice of Reasons for Rejection, issued Feb. 24, 2016, for Japanese Application No. JP2011-245163, filed Aug. 27, 2011, (Lee-Sepsick et al.—inventors) 12 pgs.
Amended Claims filed May 20, 2016 for Canadian Application No. 2770504 (Lee-Sepsick et al.—inventors) 12 pgs.
Communication from Examining Division, issued Mar. 1, 2018, for European Patent Application No. 17154076.8, divisional application, claiming priority to PCT/US2011/060049, filed Nov. 9, 2011, (Lee-Sepsick, et al.—inventors) 4 pgs.
Intention to Grant, issued Dec. 18, 2018, for European Patent Application No. 17154076.8, divisional application, claiming priority to PCT/US2011/060049, filed Nov. 9, 2011, (Lee-Sepsick, et al.—inventors) 5 pgs.
Notice of Allowance, issued Dec. 31, 2018, for U.S. Appl. No. 16/043,996, filed Jul. 24, 2018, (Lee-Sepsick, et al.) 6 pgs.
Terminal Disclaimers, filed Dec. 20, 2018, for U.S. Appl. No. 16/043,996, filed Jul. 24, 2018, (Lee-Sepsick, et al.) 3 pgs.

(56) References Cited

OTHER PUBLICATIONS

Response to NonFinal Office Action, filed Dec. 6, 2018, for U.S. Appl. No. 16/043,996, filed Jul. 24, 2018, (Lee-Sepsick, et al.) 6 pgs.
NonFinal Office Action, issued Sep. 6, 2018, for U.S. Appl. No. 16/043,996, filed Jul. 24, 2018, (Lee-Sepsick, et al.) 11 pgs.
Notice of NonCompliant Amendment, issued Sep. 20, 2018, for U.S. Appl. No. 13/292,990, filed Nov. 9, 2011, (Lee-Sepsick, et al.) 3 pgs.
Response to NonFinal Office Action, issued Oct. 15, 2018, for U.S. Appl. No. 13/292,990, filed Nov. 9, 2011, (Lee-Sepsick, et al.) 7 pgs.
Issue Notification, issued Dec. 19, 2018, for U.S. Appl. No. 15/404,887, filed Nov. 12, 2017, (Lee-Sepsick, et al.) 1 pg.
Notice of Allowance, issued Sep. 28, 2018, for U.S. Appl. No. 15/404,887, filed Nov. 12, 2017, (Lee-Sepsick, et al.) 11 pgs.
Response to NonFinal Office Action, issued Sep. 23, 2018, for U.S. Appl. No. 15/404,887, filed Nov. 12, 2017, (Lee-Sepsick, et al.) 3 pgs.
Terminal Disclaimer, issued Sep. 23, 2018, Response to Final Office Action, issued Feb. 19, 2018, for U.S. Appl. No. 15/404,887, filed Nov. 12, 2017, (Lee-Sepsick, et al.) 3 pgs.
Response to Final Office Action, issued Feb. 19, 2018, for U.S. Appl. No. 15/404,887, filed Nov. 12, 2017, (Lee-Sepsick, et al.) 11 pgs.
Final Office Action, issued Nov. 17, 2017, Response to Final Office Action, issued Feb. 19, 2018, for U.S. Appl. No. 15/404,887, filed Nov. 12, 2017, (Lee-Sepsick, et al.) 13 pgs.
Response to Notice to File Missing Parts, issued May 25, 2017, Response to Final Office Action, issued Feb. 19, 2018, for U.S. Appl. No. 15/404,887, filed Nov. 12, 2017, (Lee-Sepsick, et al.) 6 pgs.
NonFinal Office Action, issued Oct. 27, 2021, for USP U.S. Appl. No. 16/186,553, filed Nov. 11, 2018, (Lee-Sepsick) 9 p.
Response to NonFinal Office Action, issued Feb. 28, 22, for U.S. Appl. No. 16/186,553, filed Nov. 11, 2018, (Lee-Sepsick) 10 p.
Final Office Action, issued May 18, 2022, for U.S. Appl. No. 16/186,553, filed Nov. 11, 2018, (Lee-Sepsick) 9 p.
Response to Final Office Action, issued Aug. 14, 2022, for U.S. Appl. No. 16/186,553, filed Nov. 11, 2018, (Lee-Sepsick) 15 p.
Advisory Action, issued Aug. 25, 2022, for U.S. Appl. No. 16/186,553, filed Nov. 11, 2018, (Lee-Sepsick) 5 p.
Response to Final Office Action and RCE, issued Sep. 3, 2022, for U.S. Appl. No. 16/186,553, filed Nov. 11, 2018, (Lee-Sepsick) 15 p.
NonFinal Office Action, issued Oct. 20, 2022, for U.S. Appl. No. 16/186,553, filed Nov. 11, 2018, (Lee-Sepsick) 7 p.
Response to NonFinal Office Action, issued Jan. 6, 2023, for U.S. Appl. No. 16/186,553, filed Nov. 11, 2018, (Lee-Sepsick) 12 p.
Notice of Allowance, issued Feb. 1, 2023, for U.S. Appl. No. 16/186,553, filed Nov. 11, 2018, (Lee-Sepsick) 5 p.
Miscellaneous Communication, issued Feb. 15, 2003, for U.S. Appl. No. 16/186,553, filed Nov. 11, 2018, (Lee-Sepsick) 3 p.
Issue Fee Payment, issued Apr. 12, 2023, for U.S. Appl. No. 16/186,553, filed Nov. 11, 2018, (Lee-Sepsick) 2 p.
Petition and Amendment, issued Jun. 28, 2023, for U.S. Appl. No. 16/186,553, filed Nov. 11, 2018, (Lee-Sepsick) 10 p.
Notice of Abandonment, issued Jun. 28, 2023, for U.S. Appl. No. 16/186,553, filed Nov. 11, 2018, (Lee-Sepsick) 1 p.
First Examination Report, issued Jun. 25, 2009, for Indian Patent Application No. 5058/DELNP/2013, filed Nov. 9, 2011, (Lee-Sepsick) 7 p.
Patent Grant, issued Mar. 28, 2023, or Indian Patent Application No. 5058/DELNP/2013, filed Nov. 9, 2011, (Lee-Sepsick) 1 p.
Preliminary Amendment, issued Aug. 21, 2021, for U.S. Appl. No. 17/408,392, filed Aug. 21, 2021, (Lee-Sepsick) 9 p.
NonFinal Office Action, issued Sep. 14, 2022, for U.S. Appl. No. 17/408,392, filed Aug. 21, 2021, (Lee-Sepsick) 8 p.
Response to NonFinal Office Action, issued Jan. 4, 2023, for U.S. Appl. No. 17/408,392, filed Aug. 21, 2021, (Lee-Sepsick) 12 p.
Notice of Allowance, issued Feb. 10, 2023, for U.S. Appl. No. 17/408,392, filed Aug. 21, 2021, (Lee-Sepsick) 2 p.
Preliminary Amendment, issued Jun. 19, 2023, for for U.S. Appl. No. 18/131,174, filed Apr. 5, 2023, (Lee-Sepsick) 8 p.
Preliminary Amendment, issued Mar. 31, 2023, for U.S. Appl. No. 18/086,277, filed Dec. 21, 2022, (Lee-Sepsick) 6 p.
NonFinal Office Action, issued May 25, 2023, for U.S. Appl. No. 18/086,277, filed Dec. 21, 2022, (Lee-Sepsick) 8 p.
Response to NonFinal Office Action, issued Jul. 22, 2023, for U.S. Appl. No. 18/086,277, filed Dec. 21, 2022, (Lee-Sepsick) 7 p.
Notice of Allowance, issued Aug. 4, 2023, for U.S. Appl. No. 18/086,277, filed Dec. 21, 2022, (Lee-Sepsick) 7 p.

CONTRAST AGENT GENERATION AND INJECTION SYSTEM FOR SONOGRAPHIC IMAGING

RELATED APPLICATIONS

This application is a continuation of U.S. patent application Ser. No. 16/186,553, filed Nov. 11, 2018; which is a continuation of U.S. patent application Ser. No. 15/404,887, filed Jan. 12, 2017, now U.S. Pat. No. 10,172,643; which is a continuation of U.S. patent application Ser. No. 13/219,667, filed Aug. 27, 2011, now U.S. Pat. No. 9,554,826, which claims the priority of U.S. Provisional Patent Application No. 61/411,856, filed Nov. 9, 2010, and is a continuation-in-part of U.S. patent application Ser. No. 12/245,265, filed Oct. 3, 2008, now U.S. patent Ser. No. 10/070,888, each of which is herein incorporated by reference in its entirety.

TECHNICAL FIELD

The present invention relates to methods and devices for sonographic imaging of cavities and conduits, such as organs, ducts and other cavities. In particular, methods and devices of the present invention use detectable acoustic variations of alternating patterns of a gas phase and a liquid phase traversing a passage.

BACKGROUND OF THE INVENTION

Non-surgical diagnostic procedures for examining body ducts and cavities, in particular the uterus and fallopian tubes, are well known. One procedure, known as hysterosalpingography, employs contrast agents and diagnostic fluoroscopic imaging techniques for viewing the uterus and fallopian tubes. A safer, cheaper and easier method is hysterosonosalpingography or Sono HSG, where ultrasound is utilized as the imaging modality. Ultrasound imaging also allows for evaluation of the uterine cavity using saline as a method of choice without assessment of fallopian tube patency. Tubal patency and tubal occlusion can be assessed only under ideal sonographic conditions, limiting its usefulness clinically.

Currently, no contrast agent indicated for contrast enhancement during ultrasound evaluation of the uterine cavity and fallopian tubes is available in the U.S. Other ultrasound contrast agents are available for widespread use but are limited to use in cardiac and vascular applications. Most of the currently available vascular contrast agents are stabilized against dissolution and coalescence by the presence of additional materials, such as an elastic solid shell that enhances stability, or a surfactant or a combination of two or more surfactants.

Contrast agents can improve the image quality of sonography either by decreasing the reflectivity of the undesired interfaces or by increasing the backscattered echoes from the desired regions. In the former approach, the contrast agents are taken orally, and for the latter effect, the agent is introduced vascularly. To pass through the lung capillaries and enter into the systemic circulation, microbubbles within a vascular contrast agent should be less than 10 microns in diameter (2 to 5 microns on average for most of the newer agents). Stability and persistence become major issues for such small microbubbles and air bubbles in this size range persist in solution for only a short time. Hence the gas bubbles have to be stabilized for the agent to persist long enough and survive pressure changes in the heart for systemic vascular use. Therefore, availability of contrast agents, procedural challenges, particularly during preparation of the patient and the contrast materials, and cost are disadvantages associated with known contrast media used sonographically.

Although conventional contrast agents function adequately, the disadvantages inherent in the conventional agents create a need for better contrast agents. One disadvantage with currently used contrast agents is that they are very expensive and difficult for some physicians to obtain. Another disadvantage is that conventional contrast agents must be shaken prior to injection to either mix the components or to generate bubbles, thus making the entire diagnostic procedure cumbersome and possibly somewhat subjective. A third disadvantage is that the contrast agent composition has a very short shelf life due to its unstable nature once it is prepared for use in a patient.

Microbubbles in liquids have been used as contrast media previously. Microbubbles may be generated by such methods as syringe motions in a back and forth manner in combinations of air and dispersants, or ultrasonic cavitation means. It is known that such microbubbles are only stable for a short amount of time. Pre-formed microparticles using temporary or permanent polymeric films have been used to address the short stability lifespan. Pressurized systems have been used to create microbubbles in solutions. The technique involves a means of generating a focused jet of gas in order to aerate the fluids with microbubbles. Such microbubbles may coalesce if there is a lag time between generation and application into the structure to be visualized, thus these methods have used a high velocity flow of liquid. Thus, limitations to this method are that the microbubbles introduced into a fluid may coalesce into a few large bubbles or one large air pocket, the microbubbles formed must be stable long enough for visualization to occur, and due to the instability of the microbubbles, it is difficult to create reproducible conditions for comparative visualizations.

Accordingly, devices and methods are needed for creating contrast agents that resolve the issues currently encountered. Particularly, methods and devices are needed for visualization of organ structure and function, such as visualization of the uterus and fallopian tubes.

SUMMARY

The present invention comprises methods and devices for making and using contrast agents. Methods of the present invention comprise use of a device for generating a contrast agent that is used for sonographically observing organs or bodily structures, for example, the uterus and fallopian tubes. The contrast agent device may comprise a container assembly and optionally, a catheter assembly fluidly coupled to the container assembly. A container assembly may comprise a first container for providing a solution of a liquid, such as saline, and a second container for providing a gas, such as air, and elements for creating an alternating pattern of gas and fluid, which is delivered directly to the organ or structure by the catheter assembly. A container assembly may comprise one or more containers. A container assembly may comprise elements for providing the contained substance from a container to the catheter.

Methods of the present invention comprise sonographically observing a location of a body, such as a uterus and its associated fallopian tubes, using the devices disclosed herein. A method comprises placement of a catheter delivery end in close approximation to the structure to be observed, and providing the fluid/gas mixture to the structure. For example, in a method of viewing a fallopian tube, a delivery device comprising at least one catheter is placed within the uterus, and the at least one catheter is provided through the delivery device and is extended to the cornua of the uterus and the delivery end of the catheter is held in place, for example, by an end structure such as a balloon. Once the catheter(s) is in place, the liquid/gas mixture, the contrast medium, is provided from the contrast agent device to the catheter, and to the fallopian tube(s). Sonographic visualization is begun, and one or both of the fallopian tubes is examined. Depending on the delivery device used to provide the contrast agent, the fallopian tubes may be examined simultaneously or sequentially. If visualization of the entire uterus is desired, for example, after visualization of the fallopian tubes, the catheter(s) is withdrawn from the cornua, and retracted until the end structure of a single catheter is in place at the entrance to the uterus. The end structure, such as a balloon, is enlarged to provide a liquid seal of the uterus and the liquid/gas contrast agent is introduced into the uterus. Sonographic visualization is begun and may be continued until a sufficient amount of the liquid/gas contrast agent is within the uterus.

A method comprises providing a contrast medium to the uterus and fallopian tubes by providing a catheter delivery end within the uterus and delivering a contrast medium to the uterus. For example, in a method for assessing the uterus and at least a fallopian tube, a contrast agent device comprises a catheter, wherein the catheter delivery end is placed within the uterus. The catheter may optionally comprise an element for preventing retrograde flow, or flow out of the uterus through the cervix, of fluid provided to the uterus through the catheter. For example, an expandable balloon is an element for preventing retrograde flow from the uterus to the vagina. Once the catheter(s) is in place, the contrast agent, such as a liquid/gas mixture, is provided from the contrast agent device through the catheter, and into the uterus. Sonographic visualization is begun, and optionally, the uterus is visualized, and one or both of the fallopian tubes is visualized. The fallopian tubes may be examined simultaneously or sequentially. The contrast agent device may be filled and refilled one or more times to provide an effective amount of the contrast agent to the uterus and fallopian tubes, or to provide one or more visualizations of the uterus and/or a first or a second fallopian tube. Bodily structures of humans or animals, or inanimate objects can be easily observed with the contrast agents of the present invention. Providing the contrast agent directly to the structure to be observed with a catheter assembly aids in maintaining the structure of the gas and liquid segments of the liquid/gas mixture. The methods of the present invention aid in the reproducibility of the methods of visualization and comparative results therefrom.

DETAILED DESCRIPTION

Figure 1:
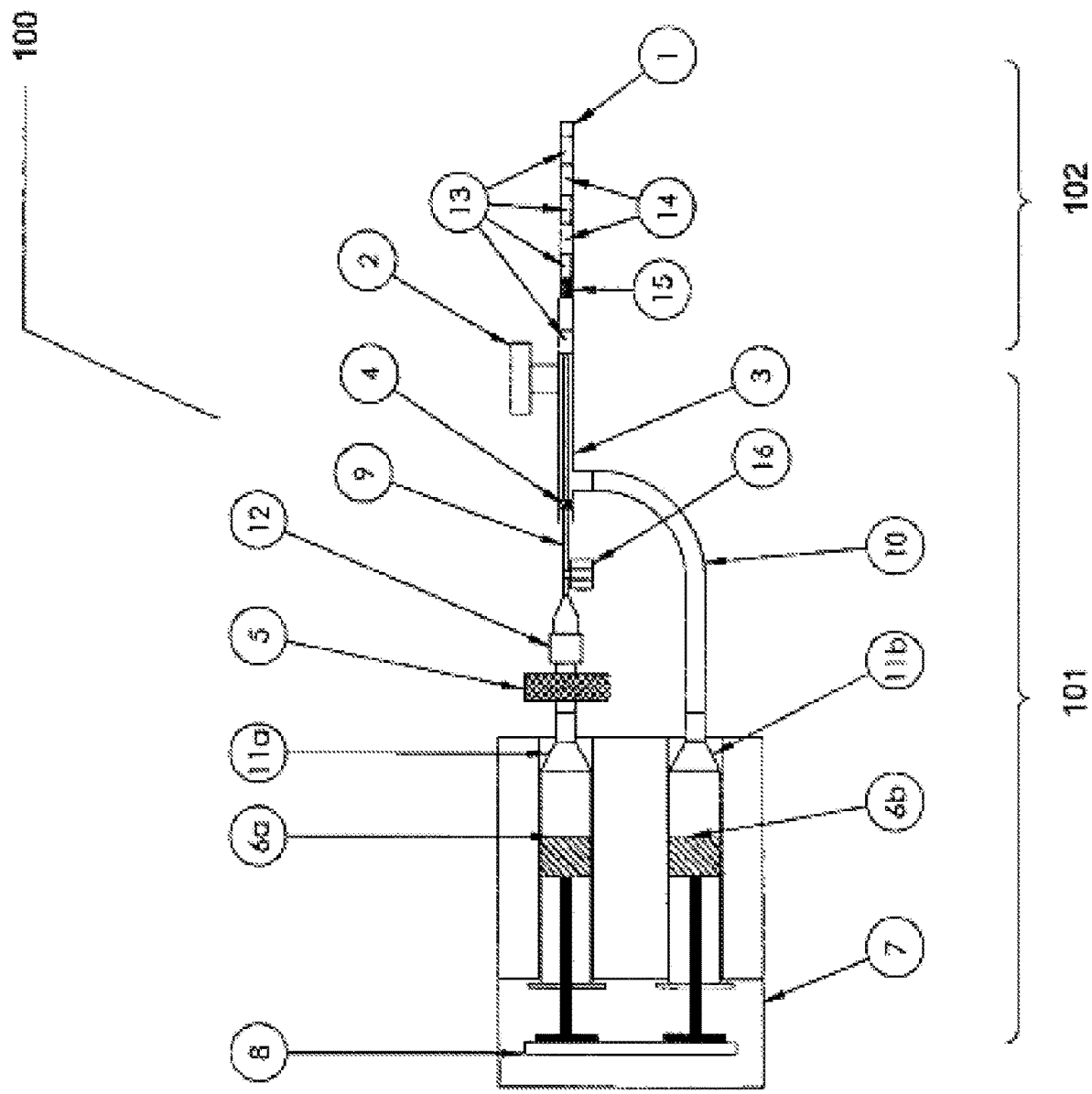
FIG. 1 is a schematic of an exemplary embodiment of the present invention.

The present invention comprises methods and devices for making and using contrast agents for ultrasound or sonography visualization of structures. Such structures may be present in the bodies of humans or animals, or may be inanimate structures. As discussed herein, the methods and devices are used for ultrasound visualization of a uterus and one or more fallopian tubes of a mammal. It is to be understood that the methods and devices are not limited to this application, but can be used in visualization of ducts or structures, whether in living beings or inanimate structures.

The present invention comprises devices for making a contrast medium composition. As used herein, contrast agent and contrast medium mean a composition that is visible or visualizable by methods known to those skilled in the art, including but not limited to ultrasound, fluorography, radiography, or other detection methods, and the terms may be used interchangeably. A method of the present invention comprises use of a contrast medium device for generating and delivering a contrast agent that is useful for sonographically observing organs or bodily structures, for example, the uterus and fallopian tubes. A method of the present invention comprises use of a contrast medium device for generating a contrast agent that is useful for sonographically observing organs or bodily structures, for example, at least one fallopian tube.

A contrast medium device comprises a container assembly and optionally, a catheter assembly fluidly coupled to the container assembly. Exemplary embodiments of a container assembly of the present invention are illustrated in FIGS. 1-4 and FIGS. 7-10. A container assembly may be provided with as casing (not shown in the FIGS.) to enclose at least a portion of the container assembly. For example, a casing may enclose the components of a container assembly, and optionally an exit port, an actuator, and/or both plunger ends may be found on the exterior of the casing.

A contrast medium device comprises a container assembly and optionally, a catheter assembly fluidly coupled to the container assembly, and optionally, pressure control elements. A container assembly may comprise at least one container for a fluid. A fluid may be a liquid or a gas. A container assembly may comprise a first container for a liquid, such as saline, and a second container for a gas, such as air, and elements for creating an alternating pattern of gas and fluid. A container assembly may comprise connection elements, such as tubing or fluid conduits, for providing the contained fluid from a container to a contrast pattern generating chamber and to the catheter assembly, or from the exterior of the container assembly to a contrast pattern generating chamber and to a container. The connection elements may be used for providing fluids from the exterior of the device to the containers. A container may comprise one or more outlets through which the fluid, such as gas or liquid, exits the container, or the outlet may be used to provide a fluid, either liquid or gas into the container. A container assembly may comprise a component for providing force upon the fluid contained within the container to move fluid into, or out of, the container. For example, a container may be a syringe body or barrel, and the component for providing force upon the fluid is a syringe plunger. The container assembly may comprise a component for activating the component for providing force. For example, the container may be a syringe body or barrel, the component for providing force upon the contained fluid is a syringe plunger, and the component for activating the plunger may be a pump, or the hand of an operator. An aspect of the invention comprises an embodiment where the contrast medium device comprises two containers, such as two syringe bodies, and the syringe plungers are moved in concert because the two plunger ends are held together by a component, such as an actuator, such that the syringe plungers move through the interior of the barrel of the syringes at the same rate, speed and distance through the interior. The syringe plungers move at the same rate, speed and distance because the proximal ends of each plunger are linked together, such as by an element, an actuator.

The container assembly may further comprise fluid connections, which are fluid connecting elements between elements that are in fluid connection with one another, such as the one or more containers and a contrast pattern generating chamber. Such fluid connections include, but are not limited to, conduits, tubing or needles. The container assembly may comprise a contrast pattern generating chamber wherein a gas phase anda liquid phase are admixed and the composition exiting the contrast pattern generating chamber, the contrast medium composition, is characterized by alternating phases of gas and liquid which form the pattern of the contrast medium composition. The container assembly may comprise fluid connections which provide the contrast medium composition to a catheter assembly or directly to a structure to be visualized.

In an embodiment, a contrast medium device may comprise a container that may function as a contrast pattern generating chamber, wherein the contrast medium is made within the container, no contrast pattern generating chamber is present, and the contrast medium composition, for example comprising gas and liquid phases, is provided to the exterior of the contrast medium device.

The container assembly may be in fluid connection with a catheter assembly. The catheter assembly may comprise a single or double lumen catheter. The catheter may comprise end structures, such as a balloon on the delivery end of the catheter, wherein the delivery end is distal from the contrast medium device and the attachment end is proximal to the contrast medium device. The opposite end of the catheter, the attachment end, may have attachment elements for attaching the catheter to for example, the contrast medium device. Attachment elements such as a luer lock, may be used to attach the catheter to a contrast medium device, and attachment elements are known. The catheter may comprise other components such as a wire, sensors, cutting elements, retrieval elements such as clamps or pincers. Such catheters are known in the art and one skilled in the art can select an appropriate catheter for the intended procedure.

The present invention comprises devices for delivery of a contrast medium to a structure. It is contemplated by an embodiment of the present invention that the contrast medium is provided by the catheter assembly substantially directly to a structure to be visualized. In an aspect of the invention, for example, in direct delivery to a fallopian tube, the amount of contrast medium used per each fallopian tube evaluation may be small, such as less than 20 mL, less than 15 mL, less than 10 mL, less than 8 mL, less than 5 mL, less than 4 mL, less than 3 mL, less than 2 mL, less than 1 mL, less than 0.5 mL. The amount of contrast fluid used may be any amount that is sufficient to provide an accurate visualization of the structure. The contrast fluid may substantially fill the structure visualized, or may only be present in particular locations within the structure.

The present invention comprises contrast medium devices for delivery of a contrast medium to one or more structures, such as to multiple cavities, organs or conduits that are in fluid connection with one another. It is contemplated by an embodiment of the present invention that the contrast medium is provided by a catheter assembly to at least one structure to be visualized, and optionally, by providing contrast medium to one structure, the contrast medium may also flow into a second, third or further structure to be visualized. In an aspect of the invention, for example, visualization of a fallopian tube may first involve providing a sufficient amount of contrast medium to the uterus so that the fluid fills the uterus to a certain extent and then the fluid is moved into one or more fallopian tubes in fluid connection with the uterus. The fluid may further move into and through the fallopian tubes to enter the abdominal cavity. The amount of contrast medium used in a procedure to view the uterus and at least one fallopian tube may be from about 5 mL to about 100 mL, from about 10 mL to about 100 mL, from about 15 mL to about 90 mL, from about 10 mL to about 80 mL, from about 20 mL to about 70 mL, from about 30 mL to about 60 mL. The amount of contrast medium generated and delivered to the patient may be about 5 mL, about 10 mL, about 20 mL, about 30 mL, about 40 mL, about 50 mL, about 60 mL, about 70 mL, about 80 mL, about 90 mL, or about 100 mL, or greater than 100 mL if needed for visualization of a uterus and fallopian tube, or for multiple visualizations. For example, a large cavity, or a cavity connected to several conduits may require more than 100 mL for visualization of the entire cavity, and/or the conduits. The amount of contrast fluid used may be any amount that is sufficient to provide an accurate visualization of the structure to be examined. The contrast fluid may substantially fill the structure visualized, or may only be present in particular locations within the structure.

For example, a contrast medium device capable of generating a contrast medium composition of about 20 mL, using two containers, syringe bodies, of 10 mL each, and transfer some or all of the contrast medium to a catheter system wherein the deliver end is positioned within the uterus. The contrast medium may enter the uterus and flow directly to the fallopian tubes where the contrast medium is visualized, for example, by sonography. Five to ten mL of contrast medium may be used for such a visualization of both fallopian tubes. The flow of contrast medium may be paused or ceased at this point. If a second visualization is desired, the flow of contrast medium may be resumed, and visualization of body structures by the presence of contrast medium may be performed.

An advantage of the present invention is that contrast medium flow is controlled so that some or all of the contrast medium composition may be provided to a body structure. The flow of the contrast medium out of the device and/or out of a catheter, and to a body structure may be controlled so that providing the contrast medium may be in a continuous flow or intermittent flow, such as providing some contrast medium, stopping the flow, providing contrast medium, stopping the flow, and so on. The container(s) of a contrast medium device may be refilled one or more times during a procedure. The flow of contrast medium to the structure may be controlled automatically or by an operator. The rate of delivery of contrast medium may be controlled. The rate of delivery may be in a range from fast to slow, and is primarily controlled by the rate of force applied to the component(s) for providing force upon the fluid contained within the container(s). In an embodiment wherein the contrast medium device comprises two containers, such as two syringe bodies, and the component for providing force upon the fluid contained within each container is a plunger, the rate of force applied to the fluid in each container is identical when the plungers are activated simultaneously with the same force applied, to provide the same rate of delivery of contrast medium from the device.

An embodiment of the present invention comprises visualization of at least one fallopian tube using a catheter placed at or near the opening of the fallopian tube. Any device that provides a catheter to the fallopian tube may be used. A catheter may be connected to the contrast medium device comprising a container assembly described herein. A particular device for providing a catheter to a body structure, such as a fallopian tube, and that may be useful in methods of visualizing a fallopian tube is the device taught in U.S. patent application Ser. No. 11/065,886, U.S. patent application Ser. No. 12/240,738, and U.S. patent application Ser. No. 12/240,791, now U.S. Pat. Nos. 8,048,086, 8,048,101, and 8,052,669, each of which is herein incorporated in its entirety. In general these applications disclose a device comprising a housing and an introducer shaft that is used to enter and traverse the uterus until the tip of the shaft approaches or touches the fundus of a uterus. Once the tip of the introducer shaft is at the fundus of the uterus, the device may be stabilized. One or more catheters, such as two, are fed through the introducer shaft and out into the uterine cavity. The placement of the introducer shaft allows for the three dimensional alignment of the catheter(s) with the cornua of the uterus. The catheter(s) is advanced until the delivery end(s) of the catheter(s) are in place in the cornua. An end structure, such as a balloon, is inflated or engaged, to stabilize the catheter(s) in place, and the end structure may prevent or minimize back-flow of materials exiting the catheter delivery end. Once the end structure is engaged, the catheter(s) is ready for delivery of materials or other activities.

In a method of the present invention, the catheter placed by the introducer shaft comprises a catheter assembly. The end of the catheter opposite the delivery end, referred to herein as the proximal end or the attachment end, is attached to a contrast medium device of the present invention. The contrast medium is generated by the actions of the container assembly and the contrast medium is provided into and through the catheter(s) and out into the cornua of the uterus and into a fallopian tube(s). Visualization techniques are initiated as the contrast medium enters the fallopian tube(s) and if possible, flows through the tube(s) and out into the peritoneal cavity. If a tube is blocked, the medium will not flow in that tube but may flow to a second, the contralateral, tube if that second tube is not blocked. The pressure built up by the blockage may or may not unseat an end structure on the catheter, such as a balloon, in an effort to relieve pressure, but if the end structure of the catheter is moved, the flow would then be directed into the uterus or the unblocked tube.

If the device providing the catheter uses only one catheter, then visualization of one fallopian tube occurs, followed by readjustment of the device, such as rotation of the introducer shaft, as taught in the cited patent applications, and the steps are repeated to provide a contrast medium to the other fallopian tube. The contrast medium provided may be any currently known contrast medium that may be provided through a catheter to a location.

An embodiment of the present invention comprises using a contrast medium device and catheter to provide contrast medium to the uterus for visualizing at least one fallopian tube, or visualization of at least a portion of the uterus and at least one fallopian tube. When the structure to be visualized is a at least one fallopian tube, or a uterus and/or at least one fallopian tube, a contrast media device of the present invention, in combination with a catheter may be used. A catheter having elements for preventing retrograde flow of fluid from the uterus may be connected to a contrast medium device comprising a container assembly as described herein. Catheters with element(s) that prevent retrograde flow are known in the art, and it is within the skill of those in the art for selecting a catheter to attach to a contrast media device of the present invention to use in methods taught herein.

In a method of the present invention, a catheter, such as a balloon catheter, is a catheter assembly. In the method, the delivery end of a catheter is placed in the uterus, and optionally, the structure to prevent retrograde flow into the cervix is employed, for example, the balloon of a balloon catheter is expanded. The end of the catheter opposite the delivery end, referred to herein as the proximal end or the attachment end, is attached to a contrast medium device of the present invention. The contrast medium is generated by the actions of the device and the contrast medium is provided into and through the catheter(s) and out into the uterus. The desired amount of contrast medium is provided and visualization techniques are initiated, and can be used to visualize the movement of the contrast medium into the uterus, to visualize at least a portion of the structure of the uterus, for example, by providing the contrast medium, and/or to visualize entry, transit and/or exit of the contrast medium in at least one fallopian tube. If a fallopian tube is blocked, the contrast medium will not flow past the blockage but may flow to the contralateral tube if not blocked. The pressure built up by the blockage may or may not be detected by an element of the contrast medium device that is designed to detect the fluid back pressure created by the lack of continued flow of the fluid through the structure and/or conduits. Should the desired pressure be reached, the contrast medium flow may be halted, such as by a medical professional providing contrast medium may stop applying pressure to the contrast medium device, and cease providing fluid through the catheter to the uterus. The contrast medium provided may be any currently known contrast medium that may be provided through a catheter to a location, or may be the liquid/air contrast medium disclosed herein.

A contrast medium device of the present invention may be provided with containers filled with fluid(s) or may be provided with empty containers that must be first filled with fluid(s) prior to generating and delivering contrast medium. If all of the fluid in the contrast medium device is used in a procedure and more contrast medium is desired, the contrast medium device of the present invention may be refilled, as in the containers of the device are filled with the respective fluid(s). In using prefilled containers, the original containers may be removed and new containers inserted into the device. In using refillable containers, the containers may be refilled without removing the delivery end of the catheter from the patient. The contrast medium device may be unattached from the proximal end of the catheter and the containers refilled with more of the same type of fluid, or a different fluid if desired, as was used in the first delivery of contrast medium.

In using a contrast medium device of the present invention, once an amount of contrast medium is provided and the containers are depleted of contrast medium, the containers may be refilled one or multiple times so as to provide an effective amount of contrast medium to the structure and/or conduits of the body. For example, in an embodiment where the contrast medium comprises air and saline segments in a pattern, which may be produced by a contrast medium device of the present invention having two containers, wherein one container provides saline and a second container provides air. For example, the containers may be 10 mL syringes, wherein a first container contains 10 mL of saline and a second container contains 10 mL of air or a gas. The contrast medium is generated or produced by simultaneously moving the saline and air from each container, such as by applying pressure to a plunger in each container, or by a pump or other means for moving a fluid from a syringe or similar container. The air and saline are moved into a contrast pattern generating chamber. The contrast pattern generating chamber may comprise a static mixer or similar structure to mix the air and liquid fluids, creating interspersed segments of saline and segments of air, thus generating a contrast medium comprising saline with air bubbles or air segments contained therein. The static mixer may comprise elements, such as helical elements that simultaneously produce patterns of flow division and radial mixing of the air and saline fluids. Static mixers are known in the art and generally comprise mixer elements contained within a tube or housing, for example a cylindrical tube. Static mixer elements may comprise a series of baffles that are made from metal or a variety of plastics. The static mixer works by continuously blending two fluids as the streams of fluids move through the static mixer. Other mixing elements may be used in the present invention, and such elements are known to those skilled in the art. Alternatively, a contrast medium generating chamber may comprise only a conduit into which both a gas conduit from the gas container and a liquid conduit from the liquid container enter, and does not comprise a static mixer or other mixing element. As the gas and liquid are simultaneously provided to the contrast medium generating chamber conduit, gas segments are created within the fluid to generate a contrast medium composition.

When the containers of the contrast medium device are empty, for example, before initiation of a procedure, or substantially all of the fluids are no longer present in the containers, such as during a procedure, in an embodiment of the present invention, the containers may be filled or refilled simultaneously without disassembly of the contrast medium device or removal of the containers from the device housing. For example, when a contrast medium device comprises two containers, wherein a first container contains saline and a second container contains air, the first and second containers may be filled or refilled with saline and air, respectively, without disassembling the contrast medium device, or removing the containers. If a catheter is attached to the exit port of the contrast medium device, it may optionally be removed when filling the containers, and left in place in the patient. The exit port end of the contrast medium device, previously attached to the catheter or prior to attachment to the catheter, may be immersed in a saline solution. If plungers are present in the containers, such as syringe plungers or similarly acting movable seals within the container body, the plungers are withdrawn up the interior of the syringe cylinder in a proximal direction and away from the exit port, creating a lowered pressure within the syringe cylinder, which causes the saline and air to enter the respective containers (syringes). Typically, the plungers are controlled simultaneously so that both plungers are drawn up the interior of the syringe cylinder at the same rate so that both syringes are refilled simultaneously with air in the air cylinder and saline in the saline cylinder. The air cylinder is in fluid connection with at least one in-line check valve attached to the air syringe barrel, and optionally with an in-line air filter, which allows for one direction filling of the air syringe barrel.

The path of air or gas during the filling of a container placed within a contrast medium device is as follows. As the air syringe barrel is withdrawn up the interior of the syringe in a proximal direction, away from the exit port, while the exit port of the device is immersed in a saline solution, air flows in through the optional air filter, through fluid connections to at least one one-way check valve, through the at least one check valve, through connectors connecting the at least one check valve and the syringe (container) exit, and into the air syringe barrel. When the plunger reaches the proximal end of the syringe cylinder, and/or is withdrawn to the desired extent, for example, the entire length of the syringe barrel, the syringe is filled, for example, with 10 mL of air.

At the same time and rate as the air syringe plunger is being withdrawn through the air syringe, the fluid syringe plunger is being withdrawn at the same rate and distance through the fluid syringe barrel. As the exit port of the contrast medium device is immersed in saline, the movement of the fluid syringe plunger in a proximal direction, away from the exit port, causes saline to enter the exit port of the device and move through the fluid connections to the fluid syringe container. When the plunger reaches the proximal end of the fluid syringe cylinder, and/or is withdrawn to the desired extent, for example, the entire length of the syringe barrel, the syringe is filled with, for example, 10 mL of fluid, for example saline. When the plungers have ceased moving, for example when each of the plungers is at the desired location within the syringe barrel, the air container and the fluid container contain substantially the same amount of air and saline in the respective containers. The contrast medium device is now filled or refilled. In continuing the visualization procedure, the catheter may be rejoined to the attachment element(s) of the exit port of the device and with opposite action by the plungers, moving down the syringe barrel toward to exit port, fluid (saline) and air are forced from the respective fluid and air containers. The contrast medium is generated in the contrast medium generating chamber, for example, by the fluid/air streams flowing through a mixer, such as a static mixer, or the fluids mixing in a mixing chamber lacking a mixing element, and the contrast medium composition comprising air and liquid segments exits the contrast medium device, for example, into and through the attached catheter. The contrast medium may enter the cavity, such as the uterus, and at least one fallopian tube, wherein visualization of the contrast medium within the structure is conducted, such as by sonographic methods, and the body structures are examined.

The disclosure herein refers to fluids such as air or saline, but it is contemplated that the present invention is not limited to air and/or saline, and that one of skill in the art can substitute air and/or saline for other appropriate fluids, such as other liquids, other gases or known contrast medium compositions. Methods of the present invention comprise making or generating a contrast medium, and delivering a contrast medium to a body structure. A contrast medium device of the present invention is used to make a contrast medium. For example, an embodiment of a contrast medium device comprising one container for fluid may comprise a container comprising a flexible porous material contained within the container. An example wherein the container is a syringe body is described, such as one shown in FIG. 4. The present invention is not limited to this design, but contemplates other containers that would function in a similar manner. The syringe is substantially filled with a flexible porous material. The flexible porous material includes, but is not limited to, strips or pieces of woven or nonwoven material, an open-celled material, such as a sponge, or fragments of a sponge, or any material that would contain a gas and release the gas when acted upon, such as by compression forces. For example, the flexible, porous material is an open-celled sponge. The sponge is placed in the container and a liquid is added, but the liquid does not displace all of the air in the sponge. The syringe plunger is applied to the large open end of the syringe and the other end of the syringe is in fluid connection with the catheter assembly. As the plunger is depressed into the syringe, the sponge is compressed and the air is forced out into the liquid, creating bubbles or air segments. The bubbles and fluid, the air and fluid segments, enter the catheter and transit the catheter to the structure. Visualization of the structure is then possible. See FIG. 5 for an illustration of visualization of a fallopian tube.

The present invention comprises contrast medium devices comprising more than one container. For example, the contrast medium device may comprise two containers, such as one shown in FIG. 1 and FIGS. 7-10, an example wherein the containers comprise a syringe body, also herein referred to as a syringe barrel or syringe container. Optionally, the interior of the syringe barrel may be traversed by a plunger element. The plunger element may be moved, such as by an operator, through the interior of the syringe container from a proximal location in the barrel, wherein proximal refers to the end of the device closest to the operator and away from the exit port of the device, to a distal location, wherein distal refers to the end of the device closest to the patient and nearer to the exit port, and from a distal location in the barrel to a proximal location in the barrel. A plunger element may be comprised of a piston and a fluid seal having two surfaces, wherein the piston is attached to one surface of the fluid seal, the proximal surface, and the other surface, the distal surface, faces and contacts the deliverable fluid. A standard syringe plunger is a plunger element. The fluid seal, having two surfaces, forms a fluid seal within the container, so that a deliverable fluid is maintained or contained on the distal surface of the plunger surface (a first surface) and no deliverable fluid is present on proximal surface (a second surface). A deliverable fluid is the fluid contained within the container and which is intended to be provided to the structure to be visualized and/or examined. As a plunger, comprising a piston and fluid seal, is moved through a syringe, there may be air or a slight vacuum created on the proximal side of the plunger, but there is no intention to provide the air on the proximal side of the seal, therefore this air is not a deliverable fluid. The present invention is not limited to this design, but contemplates other containers that would function in a similar manner. One of the containers, which may be a pre-filled syringe, contains a liquid. The liquid may be any of those disclosed herein, such as saline or water, or known contrast agent fluids. A second container, which may be a pre-filed syringe, contains a gas. The gas may be any of those disclosed herein, such as air, carbon dioxide, oxygen, nitrogen or halocarbon compound gases, other gases, or known contrast agent gases. The plungers of the two syringes are depressed simultaneously, either manually or mechanically, and the mixture of the gas and liquid form an alternating pattern of gas phase and liquid phase, which is a contrast medium composition. The contrast medium composition then enters and transits an attached catheter and exits into the structure, such as the fallopian tube. Visualization of the structure is possible by ultrasound techniques.

Alternatively, a device of the present invention may comprise two containers, such as two syringes, that are provided with no fluid. In use of such a device, each plunger is depressed to a position in the distal end of each container, such as a syringe, and the exit port of the device is placed in saline. As each plunger is simultaneously moved to a desired proximal location within the container, air is drawn into a first container and fluid is drawn into a second container. Substantially simultaneous filling of a dual container device is disclosed herein. Once the containers are filled, the plungers may be depressed, moving the surface of the fluid seal to a more distal location and dispensing the fluids from the containers. The fluids are mixed, gas and liquid are admixed to form a contrast medium composition comprising air and liquid segments, and the contrast medium composition flows out the exit port of the device, and optionally into a catheter placed within the structure to be examined. An embodiment of the present invention may comprise movement of one plunger, and filling with a fluid into, or providing a fluid from one container.

Compositions of the present invention comprise a contrast medium made using the methods taught herein. A contrast medium of the present invention comprises a gas phase within a liquid carrier. The gas phase may be a bubble or may be a liquid-free, gas-filled area adjacent to a liquid phase area, and the alternating gas-filled area and liquid area may repeat multiple times. The sizes of the gas-filled areas or the liquid filled areas may be uniform in size or not. The present invention contemplates an aspect in which providing a contrast medium in reduced volumes is used, compared to amounts currently used which may be 20 mL or more, and providing the contrast medium substantially in or very near the structure to be visualized (i.e. fallopian tube).

The present invention contemplates providing an amount of contrast medium that is effective to view a structure. For example, an effective amount of a contrast medium may comprise 5 mL to 200 mL, depending on the volume of the structure and the number of structures to be examined. For example, if a device of the present invention is used to provide contrast medium to the uterus and fallopian tubes, an effective amount of contrast medium to be provided to those structures may be greater than the amount used to provide a contrast medium directly to the fallopian tubes. The present invention controls the amount of gas and liquid used in combination to form the mixed gas/liquid composition, which enters the structure. The pattern of the contrast medium composition can range from predominantly a gas (air or other gas) phase to predominantly a liquid (saline or other liquid) phase and can be provided in a regular pattern or in an irregular pattern. The ratios of the gas to liquid may be determined by the size of the respective syringe. The larger the air syringe the greater the air segment in the pattern of the composition. The use of a porous structure may create a more random or irregular pattern. The amount of contrast medium delivered may be controlled by the amount of syringe plunger displacement or by refilling the containers one or more times.

A contrast medium device of the present invention generates and delivers a reproducible and reliable pattern of alternating air and fluid that is visible by detection methods such as sonography. The air/liquid pattern produced by a composition generated by a device of the present invention is reproducible in that a substantially regular repeating pattern of alternating air and liquid is generated as a contrast medium composition by the device, is provided to a body structure, and for example, is visible with a fallopian tube. The pattern is consistently produced by a device, as in a device of the present invention generates a contrast medium composition wherein the distance between the air/saline interfaces is short enough and repeats regularly enough that movement of the composition through a structure is visible, such as by sonography. The consistent pattern may be viewed in the uterus and in open, not blocked, fallopian tubes by detection methods, such as sonography. It is contemplated by the present invention that the distance between interfaces of a contrast medium of the present invention is not necessarily identical for every pair of interfaces but that the distances are sufficiently similar in size so as to form the perception of a repeating pattern of light and dark by detection means such as sonography, and that the structure of a body structure, such as fallopian tube, can be viewed by the movement of the regular pattern of light and dark produced by the interfaces under detection means such as sonography.

For example, in order to evaluate the fallopian tubes for patency, to determine whether the tube is open and lacking obstructions or blockages, it is desired that the saline and air composition delivered have air/saline interfaces that are in a frequent regular alternating pattern of varying intervals. Saline alone appears black when viewed by sonography as saline reflects less sound echoes to the probe, therefore, long intervals of saline may present a problem for the user to visualize a body structure, such as fallopian tube. Air appears white, as does bone, as air reflects more sound echoes to the probe, therefore, long intervals of air may be misinterpreted and easily confused with other body tissues, leading to uncertainty in the diagnosis of fallopian tube patency. Movement of the saline and air interfaces with a repeating pattern, as described by the current invention, that is frequent, regular, and alternating allows for an effect called reverberation that is caused by sound interfacing with two structures of sufficiently different reflective properties. The described invention also allows for a comet-tail effect, a type of reverberation caused by a number of small, highly reflective interfaces, such as air bubbles in a fluid. If the pattern is too erratic, as is seen in literature of historical and previously used methods, a confident and accurate diagnosis of the structure or patency of a fallopian tube cannot be assessed, and certainly not easily and reliably. With an erratic and not regular pattern, the complexity of the Sono Hysterography procedure increases dramatically, making the reliability of the procedure questionable and the learning curve, for a medical professional to learn and perform the procedure, very steep. Specifically, erratic patterns consisting of small pattern frequencies creating a long segment of either air or saline can lead to misinterpretations as there will not appear to be movement of the contrast medium, and it is the perception of the movement of the contrast medium in and through a structure that is necessary for the medical professional to make an evaluation of the fallopian tubes.

Additionally, in sonographic procedures examining the uterus and fallopian tubes, it can be challenging to obtain the optimal sonographic probe position/location in the correct plane due to varying patient anatomical positions of the uterus and fallopian tubes. Therefore, the consistent movement of a frequent, regular alternating pattern of the contrast medium, such as that generated by a device of the present invention, will increase the likelihood of the body structure (s) being viewed by the physician (medical professional) to make the intended evaluation. During the procedure, the physician may have difficulty viewing one of the fallopian tubes, such as where flow is easily viewed in one fallopian tube and the other tube is either blocked, difficult to locate or experiencing tubal spasm. In such situations and others like it, the user may need to deliver additional saline and air to the patient to rule out or confirm blockage in the unviewed tube, hence the aspect of the invention enabling quick and easy refilling of the device with fluids, such as air and saline, is advantageous for the ease and convenience of the procedure. Patient discomfort or a decision to delay the procedure a few minutes to allow the tubes to relax to challenge a difficult tube evaluation may also necessitate delay in delivery of the saline and air, extending the overall procedure time. Thus, providing a contrast medium composition that provides a regularly repeating pattern of interfaces of air segments and liquid segments, such as after a pause in the procedure or after a refilling of the device containers, is an advantage of the present invention in view of prior devices.

A composition of the present invention may comprise a liquid and a gas, and optionally, surfactants, emulsifiers, or other stabilizing agents. The liquid, which may be seen as a carrier of the gas phase, may be any liquid that is substantially free of solids and flows at normal or bodily temperatures. For example, the liquid may be water or physiologically acceptable aqueous solutions including, but not limited to, physiological electrolyte solutions, physiological saline solutions, Ringer's solution or aqueous solutions of sodium chloride, calcium chloride, sodium bicarbonate, sodium citrate, sodium acetate, or sodium tartrate, glucose solutions, or solutions of mono- or polyhydric alcohol, e.g., ethanol, n-butanol, ethylene glycol, polyvinylpyrrolidone, or mixtures or combinations of these. Further, the liquid carrier may comprise physiologically acceptable non-aqueous solutions, including, but not limited to, anhydrous or substantially anhydrous carrier liquids, alcohols, glycols, polyglycols, synthetic perfluoranated hydrocarbons, or in mixtures or combination with other non-aqueous or aqueous liquids.

Contrast media compositions of the present invention may comprise surfactants or compounds that stabilize the gas-liquid interface. Surfactants may be provided in the liquid phase of the contrast medium. For example, if a contrast medium composition comprises air and a liquid, such as saline, one or more surfactants may be added to the saline. Surfactant compositions may be useful when the contrast medium is provided to a structure that is larger than the catheter size used to transmit the contrast medium. Surfactants include tensides, such as lecithins; esters and ethers of fatty acids and fatty alcohols with polyoxyethylene and polyoxyethylated polyols like sorbitol, glycols and glycerol, cholesterol; and polyoxy-ethylene-polyoxypropylene polymers, viscosity raising and stabilizing compounds, mono- and polysaccharides (glucose, lactose, sucrose, dextran, sorbitol); polyols, e.g., glycerol, polyglycols; and polypeptides like proteins, gelatin, oxypolygelatin, plasma protein, amphipathic compounds capable of forming stable films in the presence of water and gases, such as the lecithins (phosphatidyl-choline) and other phospholipids, inter alia phosphatidic acid (PA), phosphatidylinositol, phosphatidylethanolamine (PE), phosphatidylserine (PS), phosphatidylglycerol (PG), cardiolipin (CL), sphingomyelins, the plasmogens, the cerebrosides, natural lecithins, such as egg lecithin or soya bean lecithin, or synthetic lecithins such as saturated synthetic lecithins, for example, dimyristoylphosphatidylcholine, dipalmitoylphosphatidylcholine or distearoylphosphatidylcholine or unsaturated synthetic lecithins, such as dioleylphosphatidylcholine or dilinoleylphosphatidylcholine, free fatty acids, esters of fatty acids with polyoxyalkylene compounds like polyoxypropylene glycol and polyoxyalkylene glycol; ethers of fatty alcohols with polyoxyalkylene glycols; esters of fatty acids with polyoxyalkylated sorbitan; soaps; glycerol-polyalkylene stearate; glycerolpolyoxyethylene ricinoleate; homo- and copolymers of polyalkylene glycols; polyethoxylated soya-oil and castor oil as well as hydrogenated derivatives; ethers and esters of sucrose or other carbohydrates with fatty acids, fatty alcohols, these being optionally polyoxyalkylated; mono- di- and triglycerides of saturated or unsaturated fatty acids; glycerides of soya-oil and sucrose, block copolymers of polyoxypropylene and polyoxyethylene (poloxamers) polyoxyethylenesorbitans, sorbitol, glycerol-polyalkylene stearate, glycerolpolyoxyethylene ricinoleate, homo- and copolymers of polyalkylene glycols, soybean-oil as well as hydrogenated derivatives, ethers and esters of sucrose or other carbohydrates with fatty acids, fatty alcohols, glycerides of soya-oil, dextran, sucrose and carbohydrates. Surfactants may be film forming and non-film forming and may include polymerizable amphiphilic compounds of the type of linoleyl-lecithins or polyethylene dodecanoate, phosphatidic acid, phosphatidylcholine, phosphatidylethanolamine, phosphatidylserine, phosphatidylglycerol, phosphatidylinositol, cardiolipin, sphingomyelin and biocompatible and amphipathic compound capable of forming stable films in the presence of an aqueous phase and a gas, phospholipids including phosphatidylcholine (PC) with both saturated and unsaturated lipids; including phosphatidylcholine such as dioleylphosphatidylcholine; dimyristoylphosphatidylcholine (DMPC), dipentadecanoylphosphatidylcholine-, dilauroylphosphatidylcholine (DLPC), dipalmitoylphosphatidylcholine (DPPC); disteraoylphosphatidylcholine (DSPC); and diarachidonylphosphatid-ylcholine (DAPC); phosphatidylethanolamines (PE), such as dioleylphosphatidylethanolamine, dipaimitoylphosphatidylethanolamine (DPPE) and di stearoylphosphatidylethanolamine (DSPE); phosphatidylserine (PS) such as dipalmitoyl phosphatidylserine (DPPS), disteraoylphosphatidylserine (DSPS); phosphatidylglycerols (PG), such as dipalmitoylphosphatidylglycerol (DPPG), distearoylphosphatidylglycerol (DSPG); and phosphatidylinositol. Surfactants, emulsifiers, or other stabilizing agents may be aerosolized within the gas phase.

Contrast medium compositions may comprise gases, and any physiologically acceptable gas may be present in the compositions of the present invention. The term "gas" as used herein includes any substances (including mixtures) substantially in gaseous form at the normal human body (37° C.). Close to 200 different gases have been identified as potentially useful for making ultrasound contrast agents, and include oxygen, air, nitrogen, carbon dioxide or mixtures thereof, helium, argon, xenon, krypton, $CHClF_2$ or nitrous oxide, sulfur hexafluoride, tetrafluoromethane, chlorotrifluoromethane, dichlorodifluoromethane, bromotrifluoromethane, bromochlorodifluoromethane, dibromodifluoromethane dichlorotetrafluoroethane, chloropentafluoroethane, hexafluoroethane, hexafluoropropylene, octafluoropropane, hexafluoro-butadiene, octafluoro-2-butene, octafluorocyclobutane, decafluorobutane, perfluorocyclopentane, dodecafluoropentane, fluorinated gases including materials which contain at least one fluorine atom such as $SF_6$, freons (organic compounds containing one or more carbon atoms and fluorine, i.e. $CF_4$, $C_2F_6$, $C_3F_8$, $C_4F_8$, $C_4F_{10}$, $CBrF_3$, $CCl_2F_2$, $C_2ClF_5$ and $CBrClF_2$ and perfluorocarbons. The term perfluorocarbon refers to compounds containing only carbon and fluorine atoms and includes saturated, unsaturated, and cyclic perfluorocarbons such as perfluoroalkanes such as perfluoromethane, perfluoroethane, perfluoropropanes, perfluorobutanes (e.g. perfluoro-n-butane, optionally in admixture with other isomers such as perfluoro-isobutane), perfluoropentanes, perfluorohexanes and perfluoroheptanes; perfluoroalkenes such as perfluoropropene, perfluorobutenes (e.g. perfluorobut-2ene) and perfluorobutadiene; perfluoroalkynes such as perfluorobut-2-yne, and perfluorocycloalkanes such as perfluorocyclobutane, perfluoromethylcyclobutane, perfluorodimethylcyclobutanes, perfluorotrimethylcyclobutanes, perfluorocyclopentane, perfluoromethycylopentane, perfluorodimethylcyclopentanes, perfluorocyclohexane, perfluoromethylcyclohexane and perfluorocycloheptane). The saturated perfluorocarbons, which are usually preferred, have the formula $C_nF_{n+2}$, where n is from 1 to 12, preferably from 2 to 10, most preferably from 3 to 8 and even more preferably from 3 to 6. Suitable perfluorocarbons include, for example, $CF_4$, $C_2F_6$, $C_3F_8$, $C_4F_8$, $C_4F_{10}$, $C_5F_{12}$, $C_6F_{12}$, $C_7F_{14}$, $C_8F_{18}$, and $C_9F_{20}$.

The present invention comprises embodiments of contrast medium devices and systems. A system of the present invention may comprise separable components; a contrast medium device comprising a container assembly, and a catheter assembly that provides the contrast medium composition, the fluid output of device, in, near to or in the targeted duct or cavity. Alternatively, a system of the present invention may be a single, one-piece construction with a contrast medium device comprising a container assembly adjoined to a catheter assembly. A contrast medium device may comprise a container assembly that provides a contrast medium comprising a gas phase and a liquid phase. A contrast medium device may comprise a container assembly comprising a modified conventional multiple syringe pump, either a mechanical or a manual handheld device capable of accepting variously sized syringes. The syringe outputs are directed into a mixing chamber or conduit where the appropriately created train of gas (i.e. air) and liquid (i.e. saline) are then driven into the input of a catheter assembly. For example, directed delivery of contrast medium in the proximity or within the duct (i.e. fallopian tube) will allow for sonography of the structure. A contrast medium composition may be provided directly to the fallopian tube, by which is meant that the contrast medium composition is delivered only to the fallopian tube, or only to the fallopian tube first, and not by a filling of the uterus with a fluid and having that fluid overflow into the fallopian tubes. A contrast medium composition may be provided to the uterus directly, which may allow for visualization of the uterus, and by providing a sufficient amount of contrast medium, the contrast medium may flow to one or more fallopian tubes. The contrast medium may or may not enter and flow through the fallopian tube, depending on the patency of the fallopian tube. Providing a composition directly to a structure herein means that the composition is provided at or near an opening of the structure to be assessed, so that the composition enters the structure and does not flow into the structure from a remote site of delivery of a composition.

An aspect of the invention comprises use of a device of the present invention with known hysterosalpingography procedures. For example, such procedures may be performed prior to or after use of a device of the present invention. A procedure may comprise providing saline only to the uterine cavity to at least in part fill the uterus or to distend the uterus. The uterus may be visualized by detection methods, such as sonography. The saline is then released from the uterus, such as by releasing a balloon used to seal the uterus closed from the cervix, or by withdrawing the catheter that provided the saline to the uterus. Alternatively, the saline may flow out of the fallopian tubes. After such a pre-treatment procedure, a contrast medium device of the present invention may be used by attaching the device to a catheter having its delivery end within the uterus, generating a contrast medium composition and providing the contrast medium composition to the uterus and at least one fallopian tubes. Post-treatments may also be provided to the uterus or fallopian tubes after providing the contrast medium composition. For example, a therapeutic composition or an embryo composition may then be provided to the uterus or fallopian tube. Though not wishing to be bound by any particular theory, it is theorized that providing a contrast medium composition of the present invention, using a device of the present invention aids in the fertility of a patient who has undergone the methods described herein. It is thought that there is a higher incidence of becoming pregnant found in women who have undergone a procedure comprising using a contrast medium device and air/saline contrast medium composition of the present invention. The present invention comprises a method for enhancing pregnancy in a female, aiding in or obtaining a pregnant condition in a female, or increasing the fertility of a female, comprising, providing a contrast medium generating and delivery device comprising a container assembly comprising at least one container for containing a fluid, a component for moving a fluid from the container, and connections for fluid connection of at least one container to a contrast medium generating chamber, such as a device disclosed herein, filling at least one container with a fluid; moving the fluid from at least one container to a contrast medium generating container to generate a contrast medium composition; and delivering the contrast medium composition to a body structure of the female. Visualization by detection methods such as sonography may or may not be performed.

In methods of the present invention, one or both fallopian tubes may be viewed simultaneously, sequentially or in separate procedures. In some instances, it may not be possible to view both fallopian tubes in the same plane of sonographic imaging. One or both fallopian tubes may not fill simultaneously, for example, should a spasm constrict the opening or a portion of a fallopian tube.

An aspect of the present invention comprises a contrast medium device comprising a container assembly comprising a contrast pattern generating chamber having a diameter in a range of 0.3 to 1.8 ratio to the diameter of the structure to be visualized. The diameter of the contrast pattern generating chamber may be in a ratio of 0.1 to 100 the diameter of the structure to be visualized. The contrast pattern generating chamber may have a diameter ratio of 0.5 to 1 of the structure to be visualized, a diameter ratio of 1 to 1 of the structure to be visualized, a diameter ratio of 1 to 1.5 of the structure to be visualized, a diameter ratio of 1 to 2 of the structure to be visualized. An aspect of a contrast medium device comprises a container assembly comprising a contrast pattern generating chamber that has a diameter substantially equal to the diameter of the structure to be visualized, wherein the ratio of the diameters is 1.

An aspect of the present invention comprises a contrast medium device comprising a container assembly comprising a contrast pattern generating chamber comprising a static mixer used to mix two or more fluids provided from the container(s). As two or more fluids enter the static mixer, placed in line and in fluid connection with two or more containers and before the exit port, the static mixer mixes the two or more fluids. For example, in an embodiment of a contrast medium device of the present invention, the fluid of one container is saline and the fluid of a second container is air. As the saline and air are moved from the respective containers into the static mixer, bubbles of air within the saline or segments of air and saline are created by the static mixer. Upon leaving the static mixer and exiting the contrast medium device through the exit port, and optionally into a catheter, the mixture of air and saline, primarily viewed as bubbles of air within the saline in an open space like the uterus or a patterned sequence of air and saline segments when entered into a tube, is a contrast medium that can be used to visualize a structure.

The interfaces of the alternating gas and liquid phases must be present in sufficient numbers if a duct, tube or structure is to be visualized by this contrast medium, and both phases must be present in the viewing region during the time of viewing. It is the presence of both phases traversing the viewing region that provide the visualization contrast. For example, if only one phase (either liquid or gas) is visible in the viewing region at a given time, assessment is difficult or impossible. By the creation of multiple interfaces between the two phases in the contrast medium, observation of structure is possible due to the flow of the contrast medium comprising the interfaces of the phases.

An aspect of the present invention comprises contrast medium devices comprising contrast pattern generating chambers having diameters similar in diameter to the structure being observed. For example, if gas phase is created that is smaller than the diameter of the structure to be observed, the gas will rise to the upper portion of the duct and coalesce with another gas phase and fill the diameter of the structure. An aspect of the present invention comprises contrast medium devices comprising contrast pattern generating chambers having diameters that are either larger or smaller in diameter to the structure being observed. For example, if very small gas phases are created in the contrast pattern generating chamber, the small gas phases can be maintained in a larger diameter structure using dispersing agents, surfactants, or other similar acting components in the liquid or gas phase. Such small gas phases may be achieved by vibratory manipulation of the container assembly. The higher the frequency of the oscillations, the smaller the released gas phase bubbles.

An aspect of the present invention comprises contrast medium devices comprising contrast pattern generating chambers comprising structures that can mix two or more fluids. For example, a contrast pattern generating chamber may comprise a static mixer. Static mixers and similar elements that can mix two or more fluids are known to those skilled in the art, and the present invention is not limited to the illustrations used herein. By the term mixing, it is to be understood that two or more fluids are mixed, but that interfaces between the two or more fluids is maintained in the mixed composition. It is the interfaces between the fluids that provide the contrast for visualization of structure. The interfaces may be maintained by using dispersing agents, surfactants, or other similar acting agents in the liquid or gas phase. A contrast medium of the present invention comprises interfaces between air and a fluid, such as saline, wherein the interfaces are provided by bubbles of air in saline or segments of air and saline, and the interfaces are maintained for a time sufficient to determine physical aspects of structures such as a uterus and/or at least one fallopian tube, or two fallopian tubes. For example, physical aspects may comprise the shape of a cavity, polyps within a cavity, the patency of conduits, and/or the blockage of conduits. Cavities herein may comprise any cavity of the body, for example, the uterus. Conduits herein may comprise any conduit of the body, for example, a fallopian tube.

A manual means of creating a contrast medium can be achieved by the use of a contrast medium device comprising a container assembly comprising a single syringe and a porous substance, such as open cell foams, sponges, or woven or non-woven fabrics or fibers or combinations thereof. The syringe is charged with one or more of these substances in a loosely fitted fashion and the plunger is then replaced in the fully retracted position. The contrast medium is then injected or otherwise fed or drawn into the syringe chamber containing the porous substance(s). Upon controlled depression of the syringe plunger, the fluid and air or other gas egresses in a manner similar to the dual syringe system described above. The catheter assembly delivers the contrast medium into the structure being assessed.

A use of the devices disclosed herein is to deliver contrast medium compositions to a structure to be visualized. Diagnostic or therapeutic treatments may be provided to humans or animals by delivering compositions, such as contrast medium compositions, or compositions comprising therapeutic agents to a structure by using the contrast medium device and a catheter assembly as described herein. For example, therapeutic agents may be provided to a fallopian tube in combination with alternating phase interfaces provided by the introduction of a gas to a composition comprising therapeutic agents, and for treatment of the fallopian tube such agents include, but are not limited to, methotrexate, hormones, fertility enhancing compounds, fertility interfering compounds, motility enhancing compounds, motility interfering compounds, compounds affecting the cilia/deciliation cycle, cilia growth enhancing or interfering compounds, ovarian follicle treatment compounds, antibacterial, antimicrobial, antifungal, antiviral, antimycoplasmal, or antiparisital compounds, compounds that reduce inflammation or scar tissue formation, composition comprising one or more antibiotics, antimycoplasma agents, or antiviral compounds; compositions comprising mucoproteins, electrolytes or enzymes to enhance or inhibit fertility, progesterone, estrogen, adrenergic active compounds, noradrenergic active compounds, nonsteroidal anti-inflammatory drug, prostaglandins, other compounds that may treat or prevent conditions related to the fallopian tube, uterus, ovaries, or other organs or coverings reached by a composition flowing from the cornua or ostia of a fallopian tube or combinations thereof. Therapeutic compositions comprise hormones for fertility, fertility enhancing compounds, gametes, sperm, ova, combinations of sperm and ova, one or more zygotes, or one or more embryos, or combinations thereof. In methods where delivery of such diagnostic or therapeutic agent compositions are provided by directly providing such compositions to structures, the compositions may further comprise the intermingling of a gas with the compositions comprising diagnostic or therapeutic agents, and the delivery of the compositions may be monitored by techniques such as ultrasound. A composition comprising therapeutic agents combined with the interfaces created by combining a gas with the therapeutic composition using a contrast medium device of the present invention may provide both treatment and diagnosis of the condition of a structure in one step of delivering the composition. Alternatively, a combined therapeutic agent composition with interfaces from gas/liquid phases may be employed to limit or locate the medicament in the targeted structure with the support of sonographic imaging allowing for diagnosis and treatment to occur simultaneously or in sequence.

FIG. 1 presents a schematic of an embodiment of contrast medium device 100 comprising container assembly 101, and shows a portion of a catheter assembly 102 in fluid connection with container assembly 101, for creating alternating and repetitive interfaces of gas and liquid phases. The container assembly 100 may be coupled to a catheter assembly comprising a catheter 1. The dimensions of a contrast pattern generating chamber 3 and/or a catheter may have diameters so as to maintain the distinct gas/liquid phases and thereby minimize coalescing of like phases. In some embodiments, diameters of the contrast generating chamber and the catheter may range from about 0.5 mm to about 5.0 mm. A pressure relief valve 2 may minimize undue pressure build up in a structure, such as in a fallopian tube, if the structure is blocked, such as if a fallopian tube is not patent. Such valves may be used in line in other locations in the device (not shown) or embodiments may have no valves. It may also function as a secondary relief to an end structure on a catheter, such as a balloon, when the catheter is positioned in the entryway to the fallopian tube, the cornua, and the end structure acts to hold the catheter in place.

The contrast pattern generating chamber 3 creates the phases with interfaces between a liquid (e.g., saline) phase 14 and the gas (e.g., air) phase 13. Formation of interfaces between gas and liquid phases occurs as the two media enter the contrast pattern generating chamber upon being advanced by dual syringe pump 7. A rubber septum 4 permits a needle 9 to be inserted into contrast pattern generating chamber 3 with air tight sealing. A liquid phase is introduced into contrast pattern generating chamber 3 through a connection 10, which may be tubing. The gas or liquid may be provided from either container. Valves may be added in line, such as in order to prevent possible flow along the path of least resistance, a one-way check valve 12 may be positioned posterior to needle 9. Preceding the check valve is an in-line aseptic filtration device 5 of 0.2 or so micron porosity, such filters may be used in line for either or both media. Embodiments of the present invention may comprise devices that do not include such valves or filters. Syringe 11a as well as syringe 11b may be pre-loaded with their respective medium, either liquid or gas, and placed and locked into dual syringe pump 7. The syringe pump drive block 8 advances the respective gas and liquid syringe plungers 6a and 6b in a simultaneous fashion. Junction 15 is formed between the contrast generating chamber and a catheter. Vibrator 16 is an optional element that is used to create vibrations through needle 9 to create smaller phases, such as bubbles, of the phase exiting needle 9, either gas or liquid.

An alternative embodiment comprises a dual pump where the drive block comprises two separate drivers for the two individual syringes. This permits the modification of the interface pattern, or the gas/liquid phases, to provide one phase in shorter or longer segments over the other. This could be accomplished by a slower (or faster) rate of delivery by one plunger over the other.

Needle 9 diameter may be somewhat smaller or slightly smaller than the diameter of the contrast pattern generating chamber to allow the phase delivered through needle 9 to be affected by the other phase in the contrast pattern generating chamber 3, so that the phase delivered by needle 9 is dispersed in discrete amounts. For example, surface tension of a liquid, delivered through needle 9, may cause a definite amount of liquid to detach from the needle end and form a liquid phase within the gas in the contrast pattern generating chamber. For example, the needle gauge can range from about 10 to 30.

Figure 2:
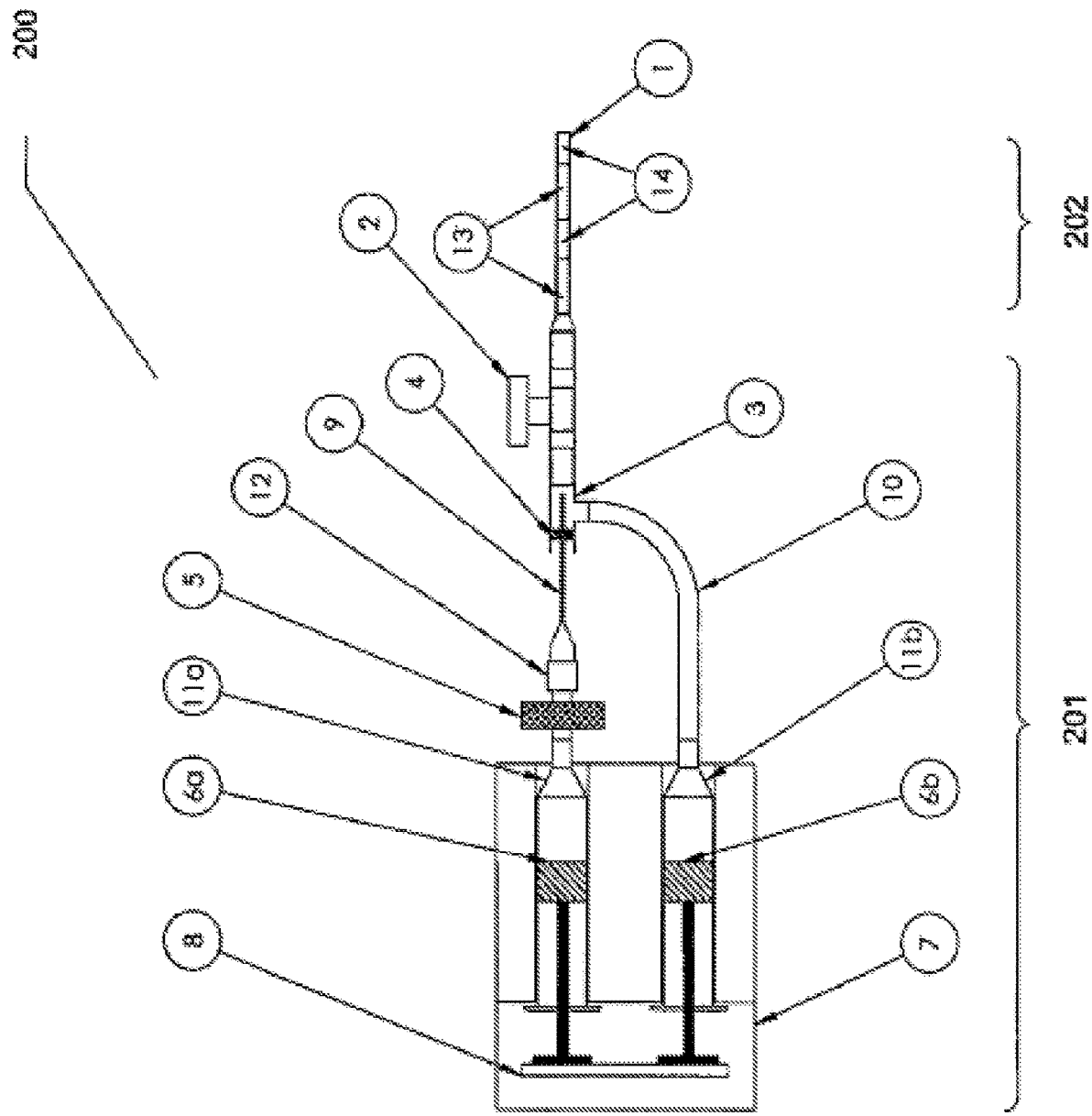
FIG. 2 is a schematic of an exemplary embodiment of the present invention.

FIG. 2 is similar to FIG. 1 except that contrast medium device 200 has a contrast pattern generating chamber having a diameter larger than a delivery catheter. FIG. 2 is numbered similarly to FIG. 1, showing container assembly 201 in fluid connection with catheter assembly 202.

Figure 3:
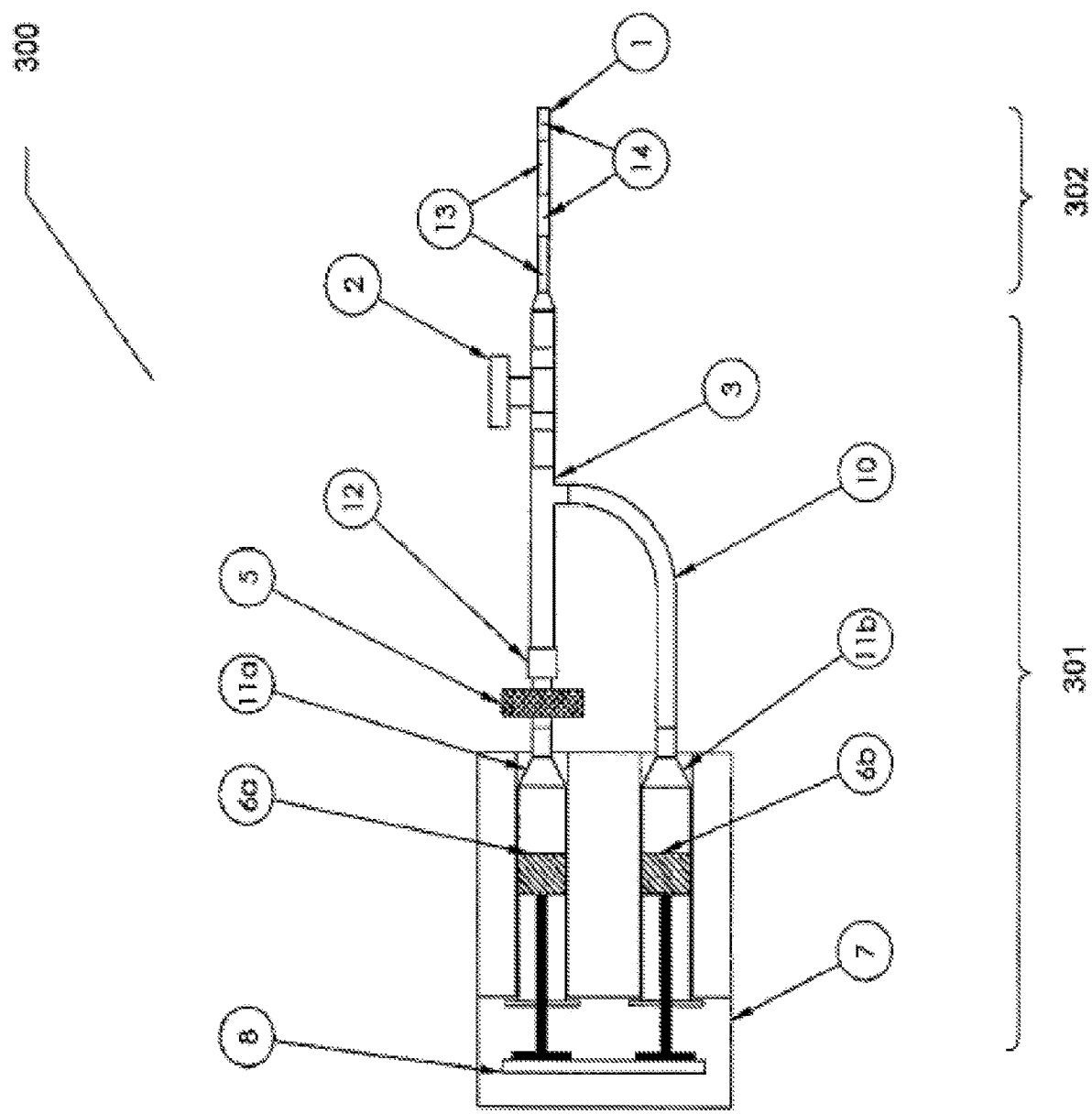
FIG. 3 is a schematic of an exemplary embodiment of the present invention.

FIG. 3 is similar to FIG. 1 except that contrast medium device 300 has a contrast pattern generating chamber having a diameter larger than a delivery catheter, and no needle 9 is present. FIG. 3 is numbered similarly to FIG. 1, showing container assembly 301 in fluid connection with catheter assembly 302.

Figure 4:
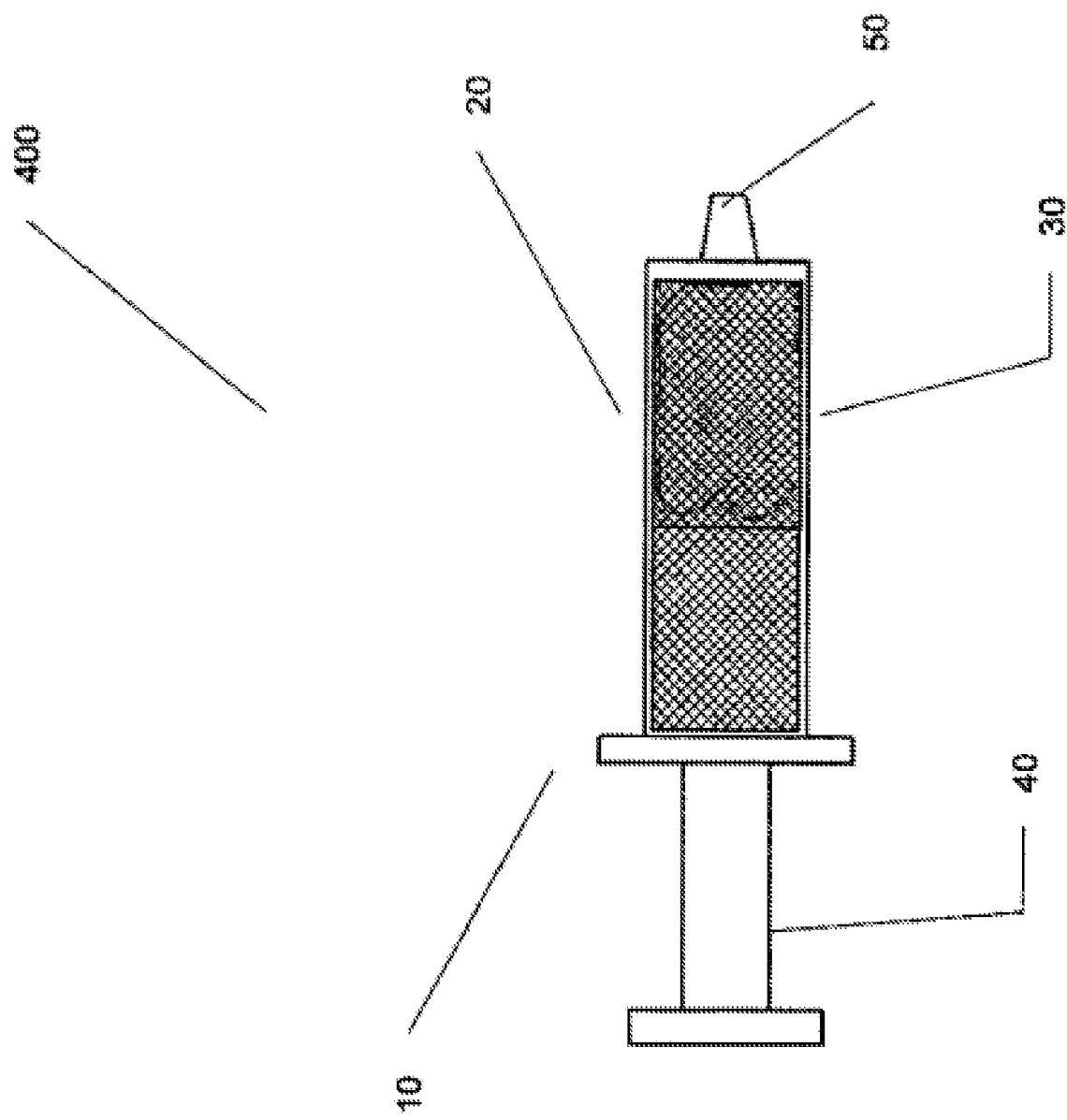
FIG. 4 is a schematic of an exemplary embodiment of the present invention.

FIG. 4 is a schematic of an embodiment of a container assembly 200 used for creating and delivering an alternating gas/liquid contrast medium to a catheter assembly or similar device. The syringe 10 is packed with a porous substance 20. The porous substance 20 is partially saturated with a liquid 30. This may be achieved by withdrawal of the plunger 40, and submersing the syringe in a liquid, injection of liquid via the syringe opening 50 or other suitable means of placement of the liquid in the interstices of the porous substance 20. For example, the porous substance may be provided in a wetted state, with the liquid already associated with the porous substance, prior to placement in the container. The syringe opening 50 is properly coupled with or without an aseptic filtration component, to a catheter assembly or similar delivery component to transfer the contrast medium to the desired site. The plunger 40 is gradually advanced so that the liquid and gas phases alternatively exit the syringe opening 50 to the catheter assembly and is delivered to the intended site to be imaged.

Figure 5:
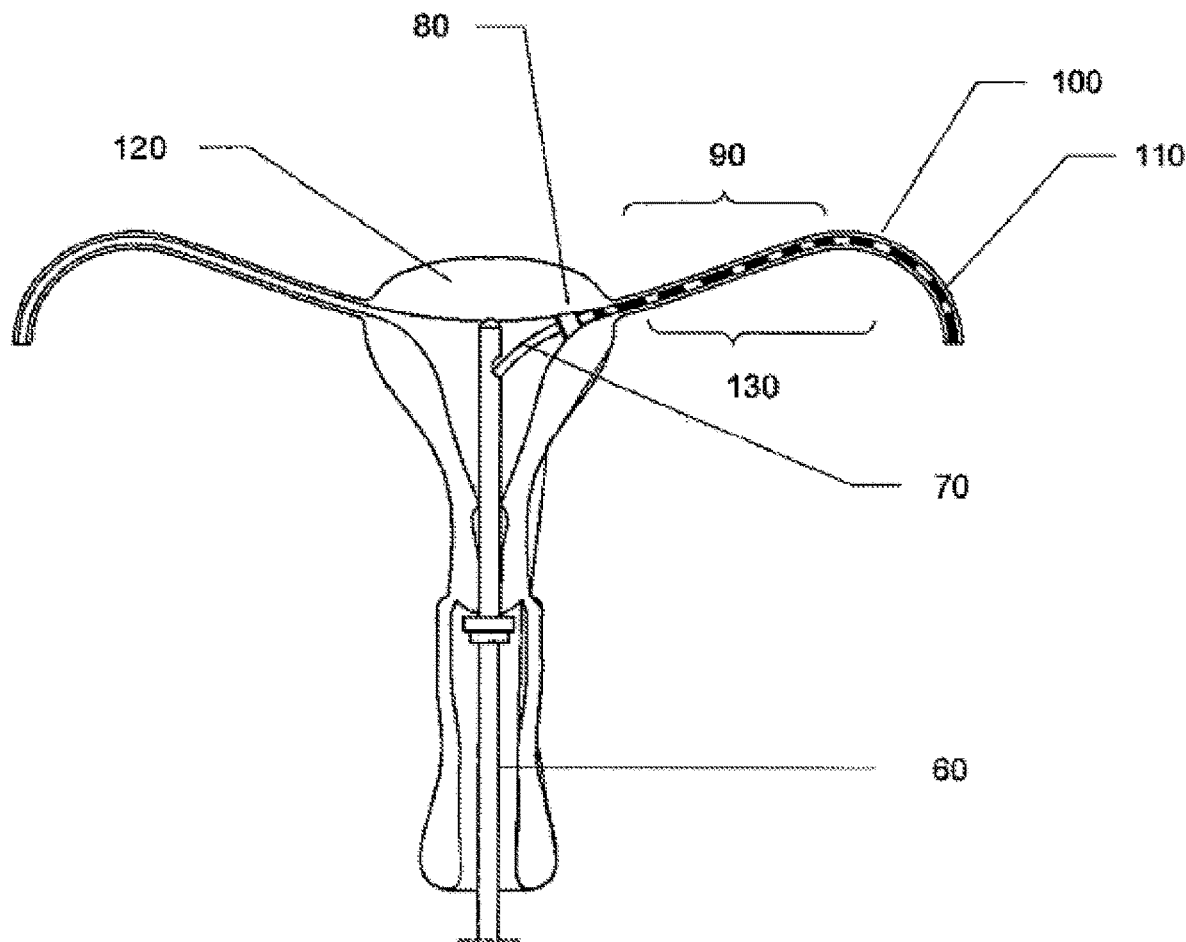
FIG. 5 is a schematic of a pattern of a contrast material in a fallopian duct.

FIG. 5 is a schematic of visualization of a fallopian tube using a contrast medium composition of the present invention, and a delivery device of U.S. patent application Ser. Nos. 12/240,738 and 12/240,791. Introducer shaft 60 is shown positioned in the uterus 120. The catheter assembly 70 is extended from introducer shaft 60 and delivery end of the catheter 80 is in place in the cornua of the uterus. Contrast medium 130 is present in fallopian tube 90, and comprises contrast medium 130 with a fluid phase 100 and a gas phase 110.

Figure 6:
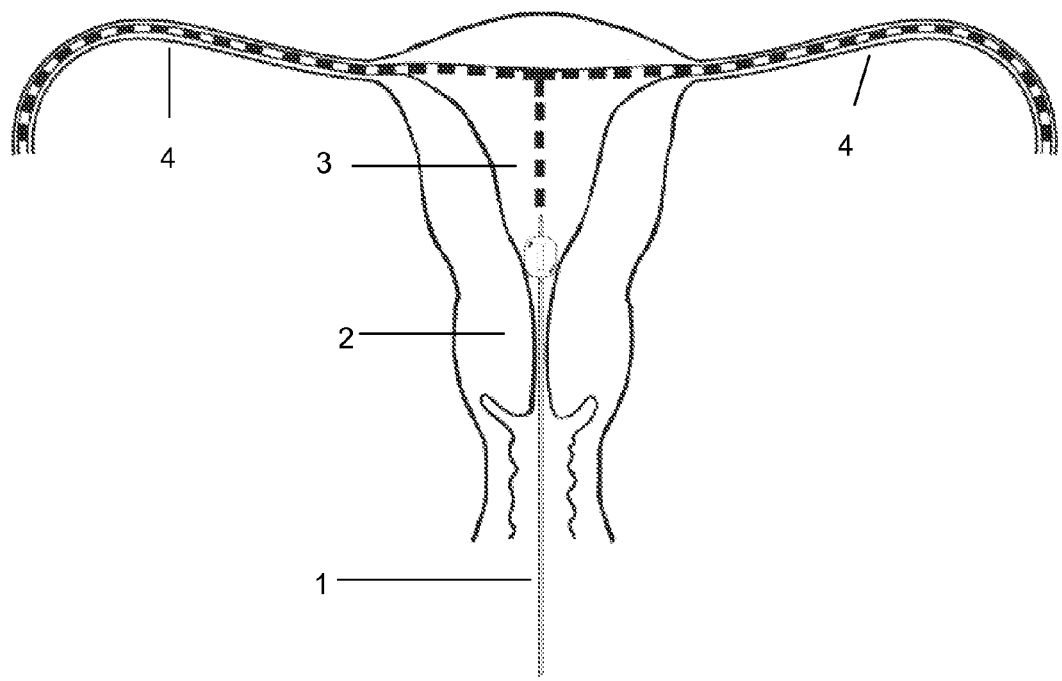
FIG. 6 is a schematic of a pattern of a contrast medium viewed within the uterus and fallopian tubes as supplied by an exemplary device of the present invention.

FIG. 6 illustrates the delivery of an air/saline contrast medium composition made by a device of the present invention wherein the air/saline composition is delivered directly to the uterus of a female mammal. The delivery end of a catheter 1 with a balloon element to block retrograde flow is placed within the uterus 2 of a mammal. A gas/liquid contrast medium 3 is generated and delivered through catheter 1 and out into uterus. The contrast medium flows through the uterus and into the fallopian tubes 4 which are visible because of the alternating pattern created by the gas/liquid segments of the contrast medium.

Figure 7:
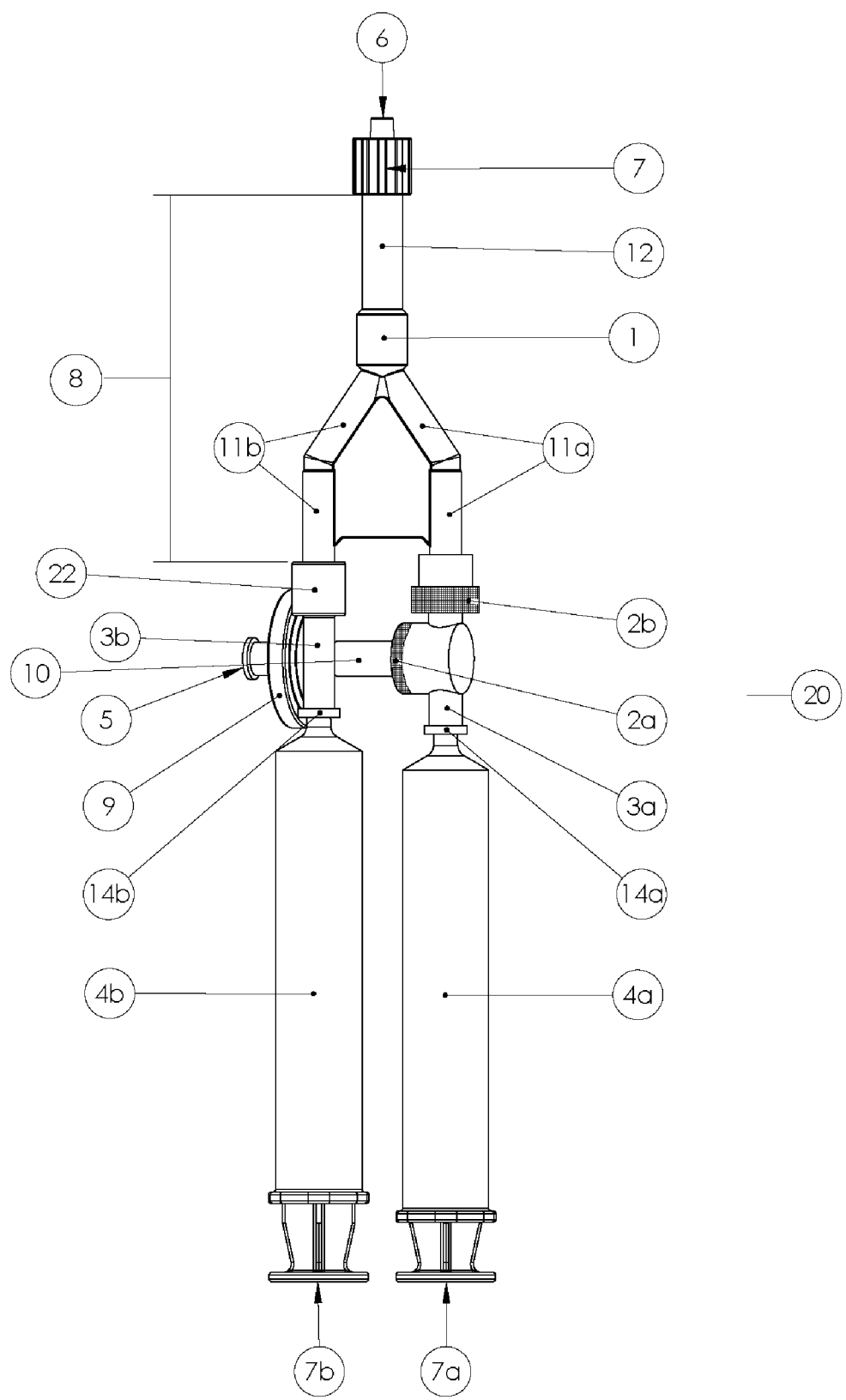
FIG. 7 is a drawing of the interior components, container assembly, of an exemplary device of the present invention.

FIG. 7 illustrates the container assembly of a contrast medium device 20 comprising a dual container embodiment of the present invention. Not shown in the figures is a casing which may enclose the components shown in the figures, but optionally, may not encase the air and exit port 6, and/or the plunger ends. From the proximal end of the figure, elements of the device are described. Plunger ends 7a and 7b, are attached to syringe plungers (not shown) maintained within the syringe bodies 4a and 4b. Not shown is an element connecting the two plunger ends so that plunger ends 7a and 7b may be actuated simultaneously. See FIG. 8 for actuator 35, as an example of an element connecting the two plunger ends. Also not shown is the entire length of each plunger, wherein each plunger end may be connected to a piston and a fluid seal displaced within the syringe body. Syringe body (Container) 4b is hollow and can contain a liquid, such as saline, and is in fluid connection with a conduit for fluid, connection 3b. Connection 3b connects to contrast medium generating chamber 8, which comprises a conduit in fluid connection respectively with each container (connections 11a and 11b) and a mixing chamber 1, and static mixer 12. Syringe body (Container) 4a is hollow and can contain a gas, and is in line and in gas connection with a check valve 2a that is line with connection 10 in the air path from the air port opening 5. Connection 10 is in line and in fluid connection with an air filter 9 which is in line and in fluid connection with an air port opening 5. For filling container 4a, air can be drawn in through air port opening 5, into and through filter 9, through connection 10, through check valve 2a, through connection 3a, through container exit port 14a and into container 4a. For providing air to contrast medium generating chamber 8, air is moved from container 4a through container exit port 14a and into connection 3a by applying pressure to plunger end 7a, which moves the plunger piston and fluid seal through the interior body of container 4a. Check valve 2b is in fluid (gas) communication with contrast generating chamber 8 so that gas from container 4a is moved from container 4a, through container exit port 14a, through connection 3a, through check valve 2b, to the proximal end of contrast medium generating chamber 8 at connection 11a in contrast generating chamber 8 and to the mixing chamber 1, which may comprise a static mixer 12. Contrast medium generating chamber 8 is in fluid connection with exit port 6. A connector, connector 7 is shown, and may be used for connecting a catheter to a contrast medium device as shown. Connecting elements, such as connector 22, such as luer locks or other tubing or conduit connectors, may be used to attach separate elements of the device.

In providing saline or any other fluid to contrast medium generating chamber 8, saline (or other fluid) is moved from container 4b through container exit port 14b and into connection 3b by applying pressure to plunger end 7b, which moves the plunger piston and fluid seal through the interior body of container 4b. From connection 3b, saline enters the proximal end of contrast medium generating chamber 8, comprising connection 11b, which is in line and in fluid connection with mixing chamber 1. The distal end of contrast medium generating chamber 8 is in fluid connection with static mixer 12, and exit port 6.

In filling the device of FIG. 7 with a liquid, such as saline, exit port 6 is immersed in the fluid, such as saline, found in a container such as a bowl or other container of fluid. The piston and fluid seal end of plunger 7b are located in a more distal position within container 4b, and a force is applied to move the plunger end, and the piston and fluid seal, away from exit port band towards the proximal end of container 4b. As the fluid seal moves through the container in a proximal direction, saline is drawn into and through exit port 6, through the contrast medium generating chamber 8 and connections 11a and 11b, where saline is prevented from flowing any further than 11a connection by check valve 2b (a one way valve), and saline continues to flow through connection 3b, container exit 14b and into container 4b.

Figure 8:
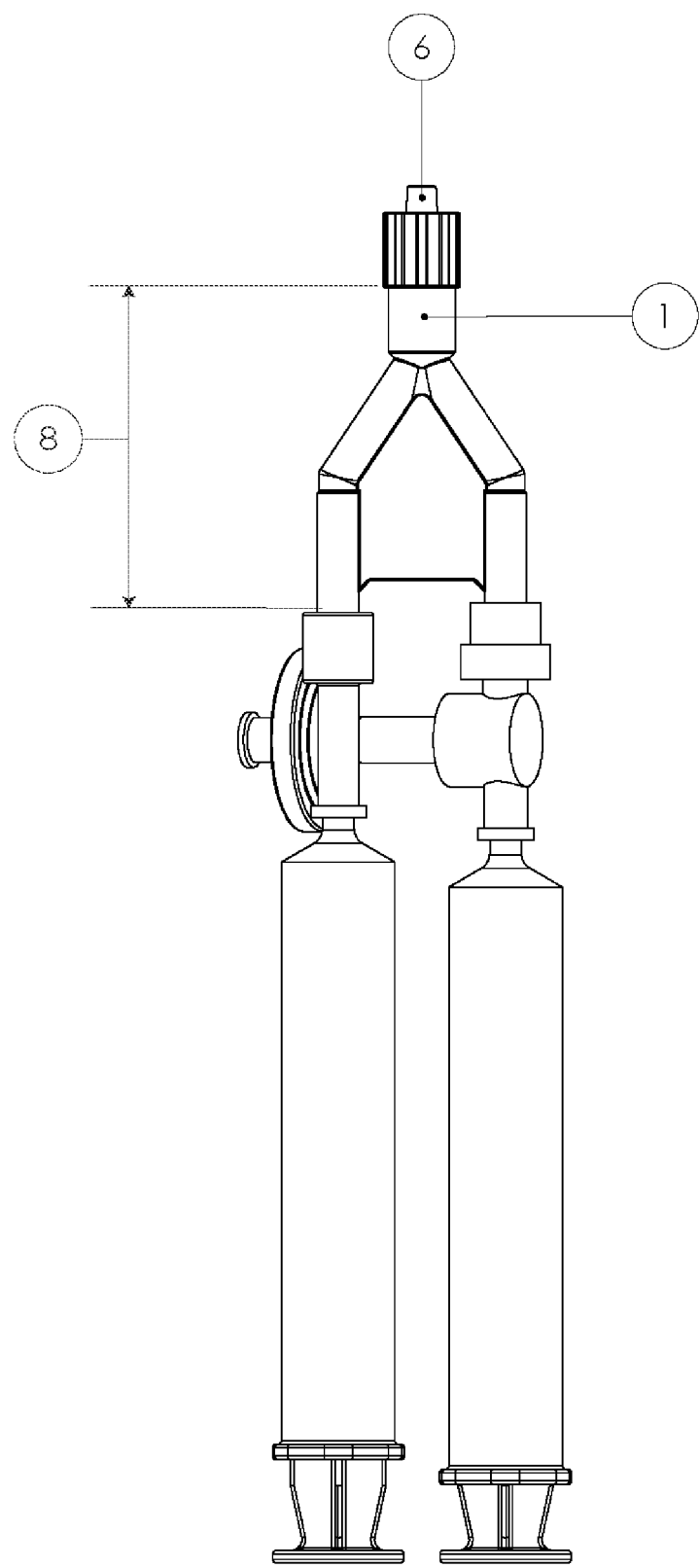
FIG. 8 is a drawing of an exemplary device of the present invention.

FIG. 8 illustrates an alternative embodiment of a contrast medium device wherein the static mixer 12 (shown in FIG. 7) is shortened or not present, and exit port 6 is connected to mixing chamber 1 of contrast medium generating chamber 8. The other elements are similar to FIG. 7.

Figure 9:
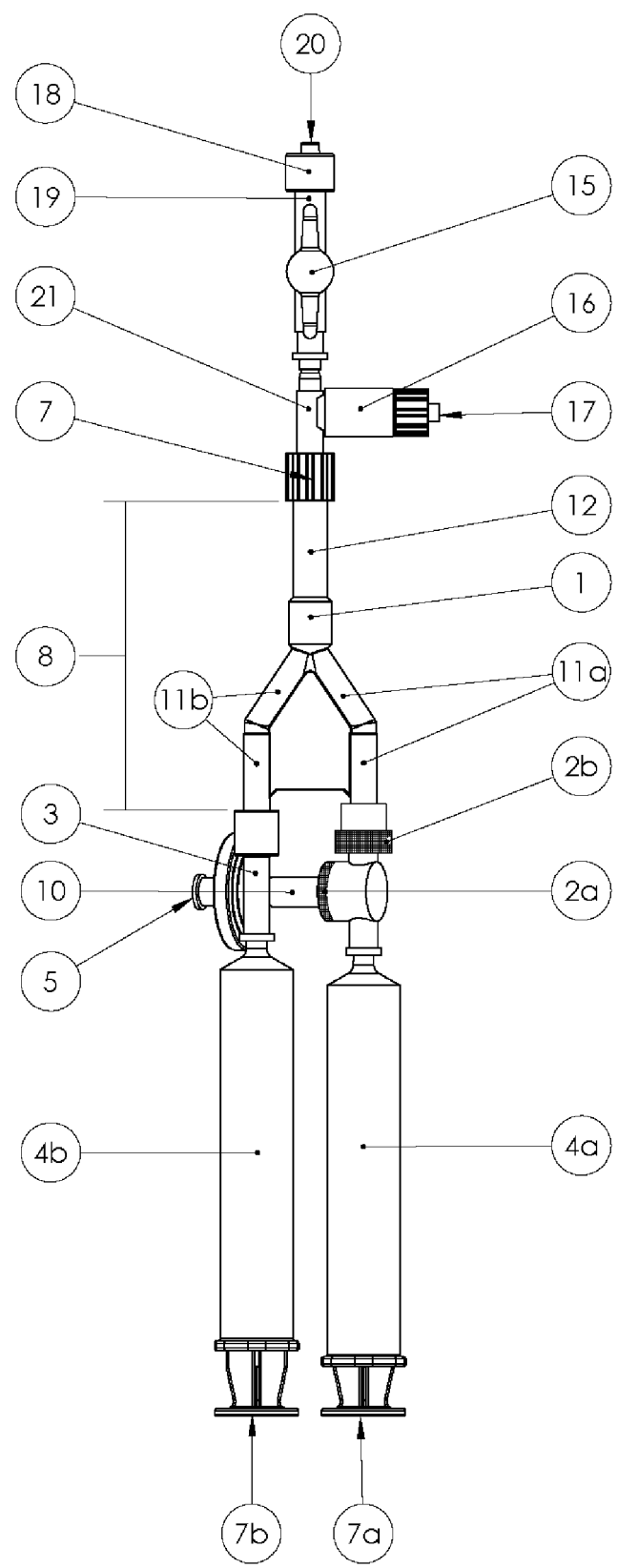
FIG. 9 is a drawing of an exemplary device of the present invention.

FIG. 9 is in illustration of the interior components (container assembly) of a contrast medium device of the present invention with pressure management elements present. The structures are numbered as in FIG. 7. The distal end of connector 7 is in line and in fluid connection with a channel 21a of the pressure relief mechanism, comprising at least elements 21a, 21b, 22, 16 and 17. Channel 21a of the pressure relief mechanism is in fluid connection with connection 19, optionally comprising a stopcock valve, which can be in an open or closed position by use of the stopcock handle 15, and in line and in fluid connection with connector 18 and exit port 20. Relief valve 21b of the pressure relief mechanism is in a closed position and is opened when the fluid pressure at the valve exceeds the allowed pressure. When the allowed pressure is exceeded, relief valve 21b opens, and fluid flows from channel 21a (or from connection 19 to channel 21a) through relieve valve 21b and into and through connector 16, which is connected to the relief valve 21b by way of tubing connection 22. Connector 16 is an attachment element for attaching a container, bag or collection device (not shown) for the fluid flowing through exit port 17. If relief valve 21b opens, stopcock 15 may be turned to close connection 19 so that fluid ceases to flow to relief valve 21b.

Figure 10:
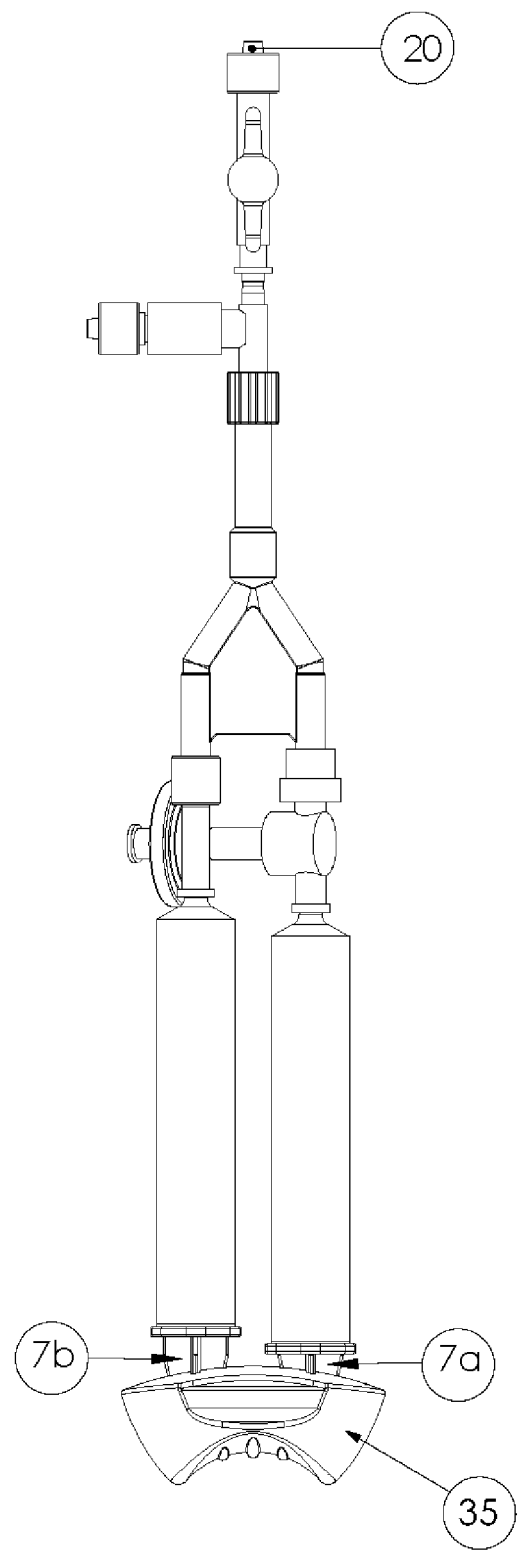
FIG. 10 is a drawing of an exemplary device of the present invention.

FIG. 10 is a illustration of the interior elements of a device of the present invention, and shows actuator 35 which when moved toward or away from the exit port 20, moves both plunger ends 7a and 7b (partially obscured in the drawing by actuator 35) simultaneously. The actuator may be external to a casing enclosing the interior elements of the device.

Methods of the present invention comprise using a contrast medium to observe structures via ultrasound techniques. The present invention comprises making a contrast medium comprising liquid and gas phases in a pattern using a contrast medium device as described herein. The contrast medium is delivered directly to or in the structure to be visualized by sonography. For example, if fallopian tubes are to be examined, the contrast medium may be delivered to the uterine cornua or at the opening of the fallopian tube by a catheter. Alternatively, a sufficient amount of contrast medium may be provided to the uterus and fallopian tubes so that the entire organ system, uterus and fallopian tubes, may be assessed by visualization techniques. Complete uterine cavity dissention may not be required to assess one or both fallopian tubes. In contrast, other known systems require filling the entire uterus with a liquid, such as saline, and then adding mixed gas/liquid composition to the saline-filled uterus and waiting until the gas/liquid mixture reaches the fallopian tubes. Procedural limitations exist with such a method in that it requires charging the uterus with enough saline for distension before the introduction of the air and saline to visualize the fallopian passages, the air present in the uterus or tubes may create air pockets that change fluid flow, and the patient may need to be maneuvered to odd positions for gas flow in a useful direction. The physician must perform multiple switching steps of a complex nature. The present invention may comprise a single step process which uses a simple automated contrast medium device or a handheld contrast medium devices.

A method of the present invention comprises providing a contrast medium device comprising a first and a second container, for example, each capable of containing 10 mL of fluid and each container is fitted with a plunger, wherein the containers are in fluid connection with an exit port and the second container is connected through at least one check valve with an air port; filling the two containers simultaneously by placing the exit port within a container of saline and withdrawing the two plungers through the two containers and away from the exit port. One container fills with saline, whereas the second container fills with air. When the plungers are withdrawn to a determined location, the first container contains saline and the second container contains air. In depressing the plungers simultaneously, so that each plunger moves through its container toward the exit port, the saline and air are moved from the respective container and into and through separate fluid connections to a contrast medium generating chamber comprising a mixing chamber comprising a static mixer, or alternatively, to a contrast medium generating chamber comprising a mixing chamber that is in fluid connection with the two separate connections from each container, and functions as a container space, a conduit, where the two separate connections from the containers are joined (a conduit mixing chamber), and a static mixer is not present. A contrast medium composition is generated and moves from the contrast medium generating chamber to enter a catheter and into a body structure. In a static mixer, the air and saline are mixed to form a contrast medium composition comprising air/saline interfaces. Alternatively, in an embodiment where the contrast medium generating chamber does not comprise a static mixer, but comprises a conduit mixing chamber, the air and saline exit their respective channels and become interspersed and mixed to form air segments (bubbles) within the fluid upon the admixing of the fluid streams, carried by the separate connections, within the mixing chamber. Such air/saline interfaces may be the result of bubbles of air surrounded by and within the saline or air and saline segments. The contrast medium composition exiting the static mixer or the conduit mixing chamber flows, optionally through an exit conduit, and out an exit port. A catheter may be connected to the conduit and the contrast medium composition flows into the catheter. After dispersing the fluids of the containers, the containers may be refilled one or more times so that a sufficient amount of contrast medium is made and delivered. Alternatively, containers may be provided that are prefilled with fluids, such as air and saline, to initially provide contrast medium and either the first prefilled containers are replaced by new prefilled containers containing fluids, such as air and saline, or the first prefilled containers, now empty, may be refilled by steps described above.

With the present invention, delivery of the contrast medium comprising a gas/liquid interface pattern from the contrast medium device to the fallopian tubes may confirm patency of the tubes by the unobstructed flow during visualization and may not result in an unnecessary buildup of material in the cul-de-sac. The delivery volume may be confined to the potential volume of the fallopian duct, approximately about 2 milliliters, for a single evaluation and may comprise a greater amount to confirm the initial observations. Imaging a fallopian tube may comprise use of a combined fluid/gas phase composition of from about 0.5 mL to about 20 mL, from about 1 mL to about 15 mL, from about 1 mL to about 5 mL, from about 1 mL to about 10 mL, from about 10 mL to about 20 mL, from about 1 mL to about 3 mL, from about 15 mL to about 20 mL. Imaging a uterus and at least one fallopian tube may comprise use of a combined fluid/gas phase contrast medium composition of from about 10 mL to about 150 mL, from about 10 mL to about 100 mL, from about 10 mL to about 50 mL, from about 20 mL to about 100 mL, from about 10 mL to about 80 mL, from about 10 mL to about 90 mL, from about 20 mL to about 90 mL. Tubal blockage may be evident by the lack of contrast medium mobility along the fallopian tube into the peritoneal cavity. Ensuing pressure relief may be provided by a relief valve in the device or by movement of an end structure on the delivery catheter from its position in the cornua. A device of the present invention lends itself to being automated once the syringes have been inserted into a pumping system or activation by manual delivery once syringes are inserted into or attached to a handheld device.

An embodiment of the present invention contemplates a contrast medium delivery device that does not require supplemental systems, such as a liquid reservoir(s) or valve control of the fluid flow from such liquid reservoirs attached to the device. Simplified devices and methods, such as those of the present invention comprising refillable containers, lead to a higher likelihood of a successful procedure and outcome. Further, the present device is able to maintain the pattern of alternating phases for periods of time that are useful for sonography. This permits the user the freedom to properly locate structures and reposition the patient or structure, or catheter during the procedure. Generally, there is no coalescing of individual phases. The pattern of gas/liquid phases or interfaces created by the contrast medium device is visually observed at the onset and each segment of media and rate of delivery can be controlled to suit the needs of the user.

The mixing of the fluids (air and saline) leads to the consistency of the alternating pattern of interfaces of air/liquid and is desired for optimally viewing the travel of the imaging agent in the fallopian tubes. Due to the size of the tubes, the consistency of the alternating pattern is needed to allow for visualization of flow with ultrasound. Other devices that have attempted to deliver saline and air did so inconsistently and the procedure was considered too difficult to make an assessment of the fallopian tubes and/or uterus by medical personnel. With previous devices, the procedures took much practice and learning of skills to use the devices and obtain visualization that was sufficient for diagnosis, whereas with the consistent alternating pattern generated by the present invention, most physicians can become proficient with the device and acquire sufficient good data routinely, after only a few uses and patients. An example of a contrast generating chamber, can be purchased commercially from Micromedics (Part: Blending Connector with static mixers) and is an example of a component that can bring the liquid and gas together consistently to create an alternating pattern that is easily visualized. The Micromedics part has a static mixer made of Keptal F30 that is in a configuration that creates turbulence of the liquid and gas. Other materials, such as foam or any porous material would serve a similar purpose to create turbulence and mix the liquid and gas. Alternatively, wherein the contrast medium generating chamber comprises a mixing chamber without a static mixer, such as one where the mixing chamber is a contained space at the juncture of two individual connections (a conduit mixing container) the alternating pattern may or may not be as consistent as a contrast medium generating chamber with a static mixer. The diameter of the separate connections, the contrast medium generating chamber, the mixing chamber and the exit port leading to a catheter influence the interval of saline and air created and may be optimized to ensure a consistent alternating pattern The liquid appears black under ultrasound while the gas appears white. The alternating pattern of black and white, that move through the cavity or conduits, allows for assessment of a small diameter tube, such as the fallopian tube or a duct. In some passageways of structures where the volumes and diameters are larger, the two phases of fluids may be maintained by additives or surfactants, such as those disclosed herein. The contrast medium device may comprise containers larger than the syringes shown herein. For example, one container may be used, and the container may contain a liquid that is foamed. The foam may be created by shaking, adding foaming agents, by sonication or stirring. The foam may be transferred to the cavity to be imaged by transporting the foam from the container assembly through a catheter assembly to the structure to be assessed. It is apparent that other methods of creating the dispersion are possible and can include mechanized means to do so. The phase created by these methods permits one to regulate the sizes of the resultant foam by control of shaking or agitation as well as the types and concentrations of the dispersants.

The methods of the present invention allow for assessment of passageways, such as the fallopian tube and uterine cavity, by ultrasound and provide a simple, safe and inexpensive outpatient method. Methods of the present invention comprise sonigraphically observing a location of a body, such as a uterus and its associated fallopian tubes, using the devices and compositions disclosed herein.

In general, the present invention comprises methods and devices for visualizing structures, by providing contrast medium compositions to the structure and visualization techniques such as ultrasound. Visualization of the contrast medium in or around the structure provides information to the viewer and such methods and devices can be used for diagnosis and treatment of conditions related to the structure viewed. The methods and devices of the present invention are useful for diagnosis and treatment of conditions related to uteri and/or fallopian tubes of humans and animals.

A contrast medium device of the present invention comprises a container assembly comprising at least one container for containing a fluid, a component for moving a fluid from the container, components for connecting the at least one container to the container assembly, and optionally comprising a catheter assembly in fluid connection with the container assembly. In embodiments of the invention, the container is a syringe and the component for moving a fluid from the container is a syringe plunger. Embodiments may further comprise a component for activating the syringe plunger, and the component is a mechanical pump or hand action. The devices may further comprise connecting elements to fluidly connect parts of the devices, valves, needles, filters, vibrators, pumps and other components.

Embodiments comprise devices where at least one container further comprises a porous substance and a gas. A porous substance may be any substance that can contain gas and liquid and release the gas and liquid easily upon compression or physical force upon the porous substance. For example, a porous substance may be a sponge, such as open cell polyurethane sponge, that may be compressible. For example, a porous substance may be material that contains a gas and a liquid is rigid, but collapses upon compression, to release the gas and liquid. A porous substance may be provided to a container in a dry state, wherein the porous substance contains gas, and a liquid may be added to the container so that the porous substance contains both a gas and a liquid. Alternatively, the porous substance may be wet, containing both liquid and gas, and thus be provided to a container. More liquid may be added to the container or not after insertion of the wetted porous substance. It is theorized that the porous substance comprises a gas within its pores and a liquid associated therewith the porous substance. The liquid and gas may be found within the pores or associated with the porous material in an easily releasable fashion, such as by surface tension, hydrogen bonding or other weak bonding associations.

The liquids provided to containers or porous substances may further comprise a surfactant, emulsifier, other stabilizing agents, or other dispersing agents. The liquids provided to containers or porous substances may further comprise liquids that are foamed. Liquids may be foamed by methods known in the art.

Embodiments of the present invention comprise contrast medium devices comprise a container assembly comprising two containers and a pattern contrast generating chamber in fluid connection with the containers. For example, the containers may be syringes, each comprising a component for moving fluid from the container that is a syringe plunger. Such embodiments may further comprise a component for activating the syringe plungers and the component is a mechanical pump or hand action. In two container devices, one container contains a gas and the other container contains a liquid. For example, where the containers are syringes, one contains a gas and the other syringe contains a liquid. In the present invention, where two or more containers are used in a device, the containers may be of the same or different size, volume, diameter, length or made from the same or different materials.

A method of the present invention comprises viewing structures using ultrasound techniques known to those skilled in the art. A method of sonographic visualization of a structure comprises, creating a contrast medium comprising alternating phases of a gas and a liquid in a contrast medium device comprising at least one container; providing the contrast medium to a catheter assembly, wherein the catheter assembly comprises a catheter delivery end positioned at or near a structure to be visualized; delivering the contrast medium directly to the structure to be visualized; and viewing the contrast medium in the structure by ultrasound. A method of sonographic visualization of a structure comprises observing a structure having a contrast medium of the present invention contained within it, or flowing through the structure. Methods of the present invention comprise making a contrast medium comprising admixing a gas and liquid in a contrast medium device such that alternating phases of gas and liquid, with visible interfaces between the phases that form a visible pattern by ultrasound, are created to form a contrast medium composition.

The present invention comprises ultrasound to visualize the contrast medium within a structure. The procedures performed with ultrasound, generally use a transvaginal probe where the probe can be placed closer to the fallopian tubes. Positioning of the probe to achieve a sagittal view allows for visualization of the sonographic imaging agent in the uterine cavity with the catheter in place, verifying forward flow into the uterine cavity absent retrograde flow back towards the vagina. Positioning of the probe to achieve a transverse view allows for visualization of the sonographic imaging agent from the uterine cavity into the fallopian tubes, which may result in both tubes or each tube viewed in a certain plane.

Any structure that is viewable using ultrasound may be viewed using the contrast medium compositions of the present invention, and contrast medium compositions made by the contrast medium devices taught herein. For example, a structure to be visualized is at least one fallopian tube of a human or animal.

The contrast medium compositions of the present invention may be made with a liquid that is flowable and forms a discrete liquid phase when in contact with a gas. The contrast medium liquid may comprise visualizable liquids or not. The contrast medium composition may further comprise a therapeutic composition. Therapeutic compositions comprise therapeutic agents including, but not limited to, methotrexate, hormones, fertility enhancing compounds, fertility interfering compounds, motility enhancing compounds, motility interfering compounds, compounds affecting the cilia/deciliation cycle, cilia growth enhancing or interfering compounds, ovarian follicle treatment compounds, antibacterial, antimicrobial, antifungal, antiviral, antimycoplasmal, or antiparisital compounds, compounds that reduce inflammation or scar tissue formation, composition comprising one or more antibiotics, antimycoplasma agents, or antiviral compounds; compositions comprising mucoproteins, electrolytes or enzymes to enhance or inhibit fertility, progesterone, estrogen, adrenergic active compounds, noradrenergic active compounds, nonsteroidal anti-inflammatory drug, prostaglandins, other compounds that may treat or prevent conditions related to the fallopian tube, uterus, ovaries, or other organs or coverings reached by a composition flowing from the cornua or ostia of a fallopian tube or any combination thereof, or combinations thereof. Treatment compositions comprise hormones for fertility, fertility enhancing compounds, gametes, sperm, ova, combinations of sperm and ova, one or more zygotes, or one or more embryos, or combinations thereof.

Methods of visualization of structures may comprise use of compositions made by a contrast medium device of the present invention. In embodiments, the contrast medium device comprises a container containing a porous substance and a fluid. The porous substance further comprises a gas, and the liquid may comprise a surfactant, emulsifier, other stabilizing agents, or other dispersing agents. The liquid may be foamed.

Methods of the present invention comprise delivery of a contrast medium composition of the present invention directly to the structure. For example, a contrast medium composition may be delivered directly to a fallopian tube. The composition may be delivered by a catheter and the catheter may be provided to the location by devices known in the art and by those taught herein. For example, the catheter may be provided so that the catheter delivery end is positioned in the cornua of a uterus. The contrast medium composition is provided through the catheter and out into the opening of the fallopian tube, and the composition flows through the fallopian tube, if possible. The contrast medium composition is visible by ultrasound and the condition of the fallopian tube can be determined by the visualization, diagnoses may be provided or treatment to the fallopian tube or other structures may be provided. For example, the patency or occlusion of at least one fallopian tube is determined when viewing the at least one fallopian tube by ultrasound. Methods of the present invention comprise using small amounts of contrast medium composition to assess or treat structures, such as a fallopian tube, and the amount of contrast medium to be provided to the structure is less than 20 mL for a single evaluation.

A contrast medium generating and delivery device of the present invention comprises a container assembly comprising at least one container for containing a fluid, a component for moving a fluid from the container, and connections for fluid connection of at least one container to a contrast medium generating chamber. A contrast medium generating and delivery device of the present invention may comprise two containers, each with a component for moving a fluid from a container. In an aspect, each container is a syringe and the component for moving a fluid from the container, is a syringe plunger. A contrast medium generating and delivery device of the present invention may further comprise a component for actuating both syringe plungers simultaneously, referred to herein as an actuator. An actuator joins the ends of the syringe plungers so that the actuator moves the plungers simultaneously in the same direction, same rate and same distance. A contrast medium generating and delivery device of the present invention may comprise a contrast medium generating chamber comprising a static mixer. A contrast medium generating and delivery device of the present invention may comprise a contrast medium generating chamber comprising a conduit mixing chamber. A contrast medium generating and delivery device of the present invention may comprise a container in fluid connection with an air port to atmosphere or other gas source. A contrast medium generating and delivery device of the present invention may comprise at least one check valve is in fluid connection with the container in fluid connection with the air port. A contrast medium generating and delivery device of the present invention may comprise at least two check valves are in fluid connection with the container in fluid connection with the air port. A contrast medium generating and delivery device of the present invention may comprise a pressure relief mechanism. A pressure relief mechanism may comprise a pressure release valve. A contrast medium generating and delivery device of the present invention may comprise a contrast medium generating chamber comprises a mixing chamber and does not include a static mixer. A contrast medium generating and delivery device of the present invention may comprise an exit port in fluid connection with the contrast medium generating chamber. A contrast medium generating and delivery device of the present invention may comprise a catheter attached to the exit port.

A method of the present invention comprises a method of sonographic visualization of a body structure, comprising, providing a contrast medium generating and delivery device comprising a container assembly comprising at least one container for containing a fluid, a component for moving a fluid from the container, and connections for fluid connection of at least one container to a contrast medium generating chamber; filling at least one container with a fluid; moving the fluid from at least one container to a contrast medium generating container to generate a contrast medium composition; providing the contrast medium composition to a body structure via a catheter comprising a catheter delivery end positioned in the same or a different body structure; viewing the contrast medium composition in one or more body structures by ultrasound. A method of the present invention may comprise at least one container prefilled with fluid. A method of the present invention may comprise a contrast medium device comprising two containers, wherein a first container is filled with air and a second container is filled with saline. A method of the present invention may comprise providing saline and air to a contrast medium generating chamber wherein the saline and air are mixed to form a contrast medium composition comprising air segments and saline segments in a pattern of regular frequency. A method of the present invention may comprise providing a contrast medium composition to the uterus and the fallopian tubes, which may be viewed using sonography.

A method of the present invention comprises diagnosing the patency of a fallopian tube, comprising, providing a contrast medium generating and delivery device comprising a container assembly comprising at least one container for containing a fluid, a component for moving a fluid from the container, and connections for fluid connection of at least one container to a contrast medium generating chamber; filling at least one container with a fluid; moving the fluid from at least one container to a contrast medium generating container to generate a contrast medium composition; providing the contrast medium composition to a body structure via a catheter comprising a catheter delivery end positioned in the same or a different body structure; and viewing the contrast medium composition in one or more body structures by ultrasound. A method of the present invention may comprise wherein the contrast medium generating and delivery device comprises two containers, wherein the containers are conjoined to effect simultaneous action, wherein a first container is filled with air and a second container is filled with saline, and providing saline and air to a contrast medium generating chamber wherein the saline and air are mixed to form a contrast medium composition comprising air segments and saline segments in a pattern of regular frequency. A method of the present invention may comprise providing a contrast medium composition to the uterus and at least one fallopian tubes and wherein the uterus and/or at least one fallopian tube is viewed using sonography.

It must be noted that, as used in this specification and the appended claims, the singular forms "a," "an," and "the" include plural referents unless the context clearly dictates otherwise.

All patents, patent applications and references included herein are specifically incorporated by reference in their entireties.

It should be understood, of course, that the foregoing relates only to preferred embodiments of the present invention and that numerous modifications or alterations may be made therein without departing from the spirit and the scope of the invention as set forth in this disclosure.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Preparation of Contrast Medium with Dual Syringe Pump

A container assembly comprising a dual pump was made, as generally depicted in FIG. 1, with two syringes, one 6 cc and the other 20 cc in volume. The 6 cc syringe was completely filled with saline and the 20 cc was filled with air. Sterile 0.2 μm filters (Sartorius Minisart or Whatman Syrfil-MF) were attached to the syringes, as sterile technique was desired. A 27 gauge, 3.5" length spinal needle was used to inject a gas phase into a fluid phase in the contrast pattern generating chamber to create the alternating air and liquid phase interfaces. A PICC-Nate catheter T-port extension and two lengths of extension tubing were utilized in the set-up.

Variations of syringe ID, pump volume, pump rate and pump delay settings were evaluated and yielded an acceptable contrast medium, as visualized in a catheter assembly forward of the container assembly. The contrast medium was delivered into clear PVC tubing that simulated the dimensions of a fallopian tube. The user could alter the pattern created with the gas and liquid phases by allowing for increased volumes of gas or liquid and the speed by which the contrast medium was delivered by adjusting the settings on the pump. A fairly regular pattern of gas/liquid phase interfaces was created by the contrast medium device.

Example 2

Preparation of Contrast Medium with Handheld Dual Syringes

The assembly of Example 1 was followed using a housing to support the dual syringes. A block was placed behind the plunger of the 6 cc syringe containing saline to align with the plunger distance of the 20 cc syringe containing air. The creation of the contrast medium and its delivery to a catheter were controlled and manipulated by hand force on the plungers of the dual syringes as necessary to deliver the contrast medium into the catheter. When the two plungers of the syringes were pushed simultaneously, the pattern of the contrast medium was uniform, with substantially equal amounts of air and saline phases, alternating in the catheter. When one plunger was pushed, followed by pushing of the plunger of the other syringe, the pattern was sometimes regular and sometimes irregular, depending on the activation of the individual plungers. Although the sizes of the individual segments of air and saline phases were not uniform, the phases of liquid/air were repeated sufficiently to view easily. The contrast medium was delivered into clear PVC tubing that simulated the dimensions of the fallopian tube.

Example 3

Preparation of Contrast Medium with Syringe Containing Porous Substance

A sterile Optipore scrubbing sponge was cut lengthwise in two equal parts. The plunger from a 60 cc syringe was removed and the sponge halves were inserted, one behind the other. The plunger was reinserted in the syringe and depressed to the 15 cc mark. The syringe tip was submerged into a sterile container of saline and the plunger was withdrawn to the 30 cc mark. The container assembly was now assembled and loaded. The container assembly was attached to a catheter assembly and the plunger was depressed to create an air and saline composition, a contrast medium composition, for sonographic visualization. The contrast medium was delivered into clear PVC tubing that simulated the dimensions of the fallopian tube. An irregular pattern or random pattern was visualized as the user controlled the delivery of the contrast medium. Although the sizes of the individual segments of air and saline phases were not uniform, the phases of liquid/air were repeated sufficiently to view easily.

Example 4

Study of Contrast Medium Created by Dual Syringe Pump in Simulated Model

A contrast medium device of FIG. 1 and Example 1 was used to deliver contrast medium created by the device, made with saline as the liquid phase and air as the gas phase, to a channel sized to mimic the human fallopian tubes in an ultrasound phantom model (purchased from Blue Phantom, a division of Advanced Medical Technologies, LLC, Kirkland, Washington). The delivery end of a catheter assembly was positioned in the simulated fallopian tube. The contrast medium device pump was activated, creating the contrast medium, and the contrast medium was delivered to the model fallopian tube and resembled the pattern shown in FIG. 5. An ultrasound machine (manufactured by GE Medical Systems, model: Voluson 730Pro) was used to visualize the contrast medium created, which traveled in real-time down the channel or simulated fallopian tube and the gas/liquid phase contrast was visualized with the ultrasound probe.

Example 5

Study of Contrast Medium Created by Dual Syringe Pump in Human Subjects

A contrast medium device of FIG. 1 and Example 1 was used to deliver contrast medium to human subjects' fallopian tubes. The contrast medium composition was created by the device using saline as the liquid phase and air as the gas phase, each traveling through an aseptic filter of approximately 0.2 microns in size to ensure sterility. The catheter assembly was provided to the human patients using a delivery system, described in U.S. patent application Ser. No. 11/065,886 placed at the cornua of each subject. The contrast medium was delivered through the catheter of the delivery system and was visualized using an ultrasound instrument (manufacturer: GE Medical Systems, Model: Logic 500). Tubal patency was evidenced by contrast medium traversing the fallopian tubes and exiting into the peritoneal cavity. This evaluation was conducted in real-time with assessment of contrast medium flow evident upon proper positioning of the delivery system.

Example 6

Study of Contrast Medium Created by Syringe Containing Porous Substance in Simulated Model A contrast medium device like that shown in FIG. 4 and Example 3 was used to deliver contrast medium created by the device, wherein saline was the liquid phase and air was the gas phase, to a channel sized to mimic the human fallopian tubes in an ultrasound phantom model (purchased from Blue Phantom, a division of Advanced Medical Technologies, LLC, Kirkland, Washington). The porous substance used was a highly porous polyurethane open cell foam designed for protective packaging material. A delivery end of a catheter assembly was positioned in the simulated fallopian tube and the contrast medium device was activated by hand, creating a contrast medium that was more irregular in pattern than that shown in FIG. 5. An ultrasound machine (manufactured by GE Medical Systems, model: Voluson 730Pro) was used to visualize the contrast medium created, which traveled in real-time down the channel or simulated fallopian tube and the gas/liquid phase contrast medium composition was visualized with the ultrasound probe.

Example 7

Study of Contrast Medium Created by Syringe Containing Porous Substance in Human Subjects A contrast medium device like that shown in FIG. 4 and Example 3 was used to deliver contrast medium created by the device wherein saline was the liquid phase and air was the gas phase, to human subjects' fallopian tubes by way of a catheter assembly incorporated in a delivery system as described in U.S. patent application Ser. No. 11/065,886. The delivery device was placed in the uterus of a human subject and the delivery end of one or both catheters were in place in the cornua of the uterus. A 60 cc sterile syringe was packed with a 3×2" sterile Optipore wound cleansing sponge (manufactured for ConvaTec, division of E. R. Squibb &

Sons, LLC, Princeton, NJ). The sponge was constructed of polyurethane and was highly porous in nature. Saline was drawn into the syringe so as to fill the syringe, but not to remove the air trapped in the sponge. The syringe was attached to the attachment end of one or both catheters of the delivery device. When the plunger of the syringe was depressed, the contrast medium was formed and was delivered through the catheter assembly, and out into the fallopian tube(s). The contrast medium was visible under ultrasound (manufacturer: Philips, Model: HD3). This evaluation was conducted in real-time with assessment of contrast medium flow evident upon proper positioning of the delivery system.

Example 8

Study of Contrast Medium Created by Four Channel Configurations in Bench Model

A contrast medium device like that shown in FIG. 7 was altered to produce the following four configurations to evaluate the contrast media intervals:
a) Contrast medium device as depicted in FIG. 7 (with static mixer) with each fluid channel having an ID (interior diameter) of 0.022" moving to ID 0.100" in the static mixer.
b) Contrast medium device as depicted in FIG. 8 (no static mixer) with each fluid channel having an ID of 0.022".
c) Contrast medium device like FIG. 8 with each fluid channel having an ID of 0.045".
d) Contrast medium device like FIG. 8 with each fluid channel having an ID of 0.017".

All contrast medium devices were connected to a 2.2 mm tube, which simulated the diameter of the fallopian tube to evaluate the interval of fluids created. It was found that with these fluid channel inner diameters and with or without static mixer, the length of the saline compared to the length of the air intervals created were substantially the same, with an average length of about 5 mm.

Example 9 Saline and Air Analyzed for Differences in Frequency of Pattern and Segment Length with Various Rates of Delivery A system for simulating the female reproductive system, including cervix, uterine cavity and fallopian tubes was created to allow for analysis of various delivery rates of the device described in FIG. 7 and possible effects of the frequency of air and saline pattern and the lengths of the respective segments. The length of air segments and rate of delivery for several experiments are shown in Table 1.

The testing apparatus consisted of a clear soft elastomer material sandwiched between two clear acrylic plates. The bottom plate had a similarly sized depression representative of the uterine cavity where the elastomer was placed over. The acrylic plates were bolted together creating a water tight seal. The top plate consisted of the following: a) one inlet fitted with a 2 mm bore elastomer tubing of short length to simulate the internal cervical os that was sufficient to accommodate a standard intrauterine balloon catheter and b) two outlets fitted with two 2 mm bore elastomer tubing to simulate the inner diameter of each fallopian tube. Each tube length was approximately 400 mm to allow for multiple data readings. The testing apparatus was fixtured to a standard table top model tensile testing machine (Instron). A bracket was fabricated to hold the device to the Instron but allowed for removal as needed for refilling of the saline and air. The device was connected to the testing apparatus containing the standard intrauterine catheter. The cross head of the Instron was placed against the plunger of the fully filled device and advanced forward at a set rate, simulating delivery.

TABLE 1

| Rate of Delivery | Average Frequency Saline-Air Pattern | Average Length of Air Segment | Average Length of Saline Segment |
| --- | --- | --- | --- |
| 1.46 cc/sec | 10 air/9 saline | 7.6 mm | 3.5 mm |
| 0.73 cc/sec | 6 air/6 saline | 9.8 mm | 7.5 mm |
| 0.29 cc/sec | 4 air/3 saline | 17.0 mm | 8.9 mm |

Example 10 Saline and Air Delivered by a Device Incorporating a Pressure Relief Mechanism The device described in FIG. 9, included a 3.0 PSI (155 mmHg) pressure relief valve. A testing apparatus consisting of the device connected to a disposable pressure transducer (Utah Medical P/N DPT-100), which was then connected to a pressure monitor (PendoTech PressureMat 3Plus), which was then connected to a standard digital computer was used for measuring the pressure achieved when delivering saline and air. A fluid containment bag was attached to the relief port of the pressure relief valve to capture excess fluid expelled from the pressure relief valve when activated.

The device of this example was designed to limit the injection pressure of saline and air instilled into a closed system to a value at or below 200 mm Hg. When the inline pressure met or exceeded the pressure rating of 3.0 PSI (155 mmHg), the valve opened, and fluid was expelled from the relief port of the pressure relief valve.

Figure 11:
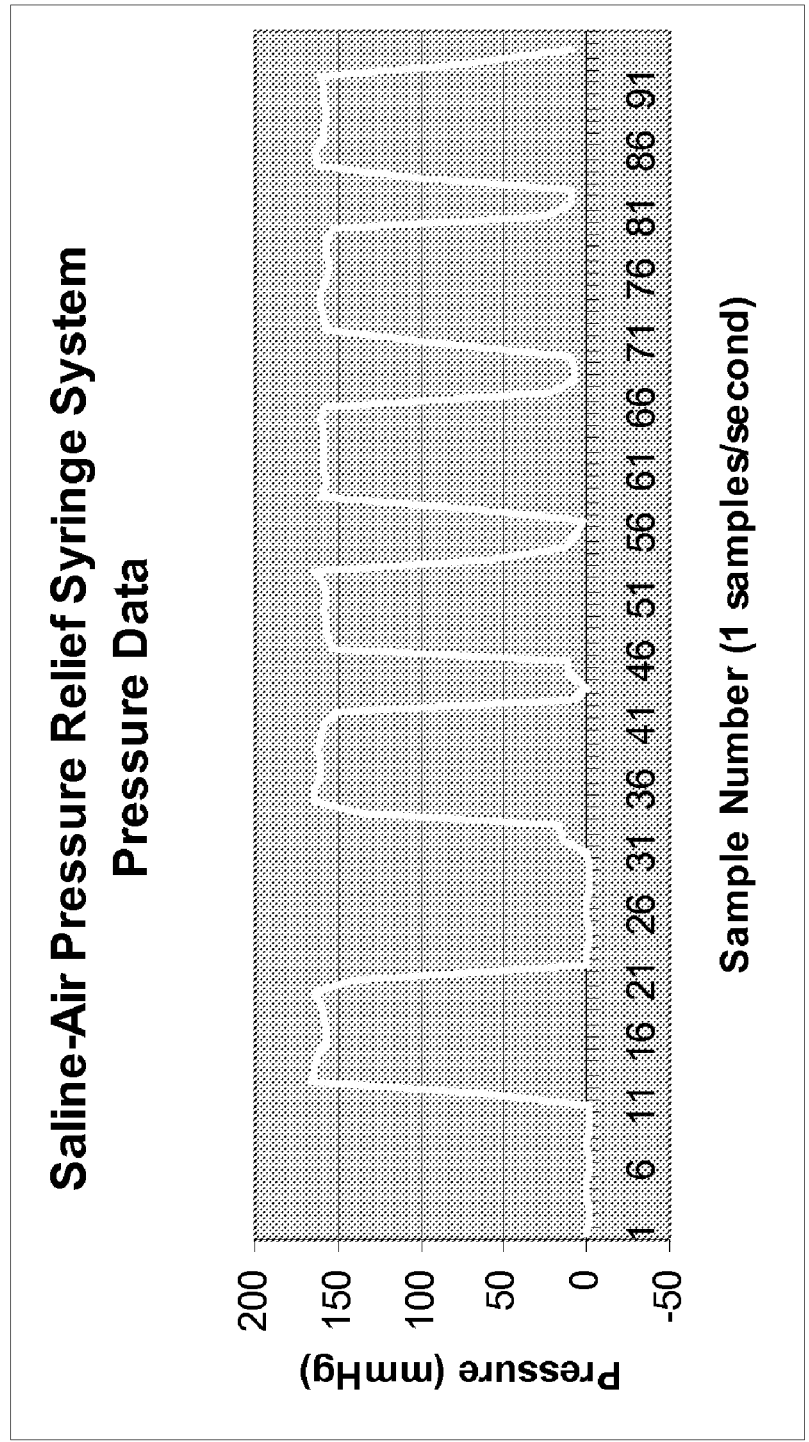
FIG. 11 is a graph of the pressure readings from experiments with an exemplary device comprising a pressure relief mechanism.

Fluid injection pressure measurements of the device were captured in a simulated closed system, which was achieved by placement of a cap over the port on the opposite end of the transducer. The transducer was primed with the saline, and it was visually verified that no air bubbles were in proximity of the sensing portion of the transducer before pressure measurements were obtained to ensure accurate fluid pressure readings. The test was repeated 6 times with results depicted in the graph shown in FIG. 11.

What is claimed is:
1. A method of diagnosing the patency of two fallopian tubes, comprising, a) providing to a uterus or to two fallopian tubes, a contrast medium composition made by a contrast medium generating and delivery device, comprising, i) a container assembly comprising a first and second container, the first container configured for containing a liquid and the second container configured for containing air or gas; a contrast medium generating chamber; a first connection for fluid connection between the first container and the contrast medium generating chamber, and a second connection for fluid connection between the second container and the contrast medium generating chamber; an air port positioned between the second container and the contrast medium generating chamber in the connection for fluid connection between the second container and the contrast medium generating chamber, that is in fluid connection with the second container; and a third connection for fluid connection between the contrast medium generating chamber and an exit port distal to the contrast medium generating chamber; ii) first and second container plungers, respectively disposed within the first and second containers for firstly simultaneously moving the liquid or the air or gas into the respective container, and secondly for simultaneously moving the contained liquid or the air or gas from the respective container, through the respective first and second connection for fluid connection, to the contrast medium generating chamber to form a contrast medium comprising the liquid and the air or gas that exits through the exit port; and b) viewing the contrast medium composition in the uterus or two fallopian tubes and diagnosing the patency of the two fallopian tubes.

2. The method of claim 1, wherein the viewing is by sonography.

3. The method of claim 1, wherein the device further comprises a component for actuating both container plungers simultaneously.

4. The method of claim 1, wherein the device further comprises at least one check valve that is in fluid connection with the container in fluid connection with the air port.

5. The method of claim 1, wherein the device further comprises at least two check valves are in fluid connection with the container in fluid connection with the air port.

6. The method of claim 1, wherein the device further comprises a stop cock positioned between the contrast generating chamber and the exit port.

7. The method of claim 1, wherein the device further comprises a catheter attached to the exit port.

8. The method of claim 1, wherein the liquid further comprises one or more of a surfactant, emulsifier, stabilizing or dispersing agents.

9. The method of claim 1, wherein the surfactant, emulsifier, stabilizing or dispersing agent comprises one or more of a tenside, a lecithin; phosphatidyl-choline; an ester or ether of fatty acids and fatty alcohols with polyoxyethylene; polyoxyethylated polyols; sorbitol, glycols and glycerol, cholesterol; polyoxy-ethylene-polyoxypropylene polymers, viscosity raising and stabilizing compounds, mono- and polysaccharides, glucose, lactose, sucrose, dextran;

glycerol, polyglycols; and polypeptides; proteins, gelatin, oxypolygelatin, plasma protein, amphipathic compounds capable of forming stable films in the presence of water and gases;

phospholipids, phosphatidic acid (PA), phosphatidylinositol, phosphatidylethanolamine (PE), phosphatidylserine (PS), phosphatidylglycerol (PG), cardiolipin (CL), sphingomyelins, a plasmogen, a cerebroside, egg lecithin or soya bean lecithin, or synthetic lecithins;

dimyristoylphosphatidylcholine, dipalmitoylphosphatidylcholine; distearoylphosphatidylcholine;

unsaturated synthetic lecithins, dioleylphosphatidylcholine, dilinoleylphosphatidylcholine, free fatty acids, esters of fatty acids with polyoxyalkylene compounds; polyoxypropylene glycol;

polyoxyalkylene glycol; ethers of fatty alcohols with polyoxyalkylene glycols; esters of fatty acids with polyoxyalklated sorbitan; soaps; glycerol-polyalkylene stearate; glycerol-polyoxyethylene ricinoleate; homo- and copolymers of polyalkylene glycols; polyethoxylated soya-oil and castor oil or hydrogenated derivatives of polyethoxylated soya-oil and castor oil; ethers and esters of sucrose with fatty acids or fatty alcohols, polyoxyalkylated ethers and esters of sucrose with fatty acids or fatty alcohols; mono-di- and triglycerides of saturated or unsaturated fatty acids;

glycerides of soya-oil and sucrose, block copolymers of polyoxypropylene and polyoxyethylene (poloxamers), polyoxyethylenesorbitans, glycerol-polyalkylene stearate, glycerolpolyoxyethylene ricinoleate, homo- and copolymers of polyalkylene glycols, glycerides of soya-oil, dextran, sucrose and carbohydrates; polymerizable amphiphilic compounds of linoleyl-lecithins or polyethylene dodecanoate, phosphatidic acid, phosphatidylcholine, phosphatidylethanolamine, phosphatidylserine, phosphatidylglycerol, phosphatidylinositol, cardiolipin, sphingomyelin;

phosphatidylcholine (PC) dioleylphosphatidylcholine; dimyristoylphosphatidylcholine (DMPC), dipentadecanoylphosphatidylcholine-, dilauroylphosphatidylcholine (DLPC);

dipalmitoylphosphatidylcholine (DPPC); disteraoylphosphatidylcholine (DSPC);

diarachidonylphosphatid-ylcholine (DAPC); phosphatidylethanolamines (PE), dioleylphosphatidylethanolamine, dipalmitoylphosphatidylethanolamine (DPPE) distearoylphosphatidylethanolamine (DSPE); phosphatidylserine (PS), dipalmitoyl phosphatidylserine (DPPS), disteraoylphosphatidylserine (DSPS); phosphatidylglycerols (PG), dipalmitoylphosphatidylglycerol (DPPG), distearoylphosphatidylglycerol (DSPG); or phosphatidylinositol.

10. The method of claim 1, wherein the liquid is water; a physiological electrolyte solution, a physiological saline solution, Ringer's solution, an aqueous solution of sodium chloride, calcium chloride, sodium bicarbonate, sodium citrate, sodium acetate, or sodium tartrate; a glucose solution, a solutions of mono- or polyhydric alcohol, ethanol, n-butanol, ethylene glycol, polyvinylpyrrolidone, a physiologically acceptable non-aqueous solution, an anhydrous or substantially anhydrous carrier liquid, a solution of an alcohol, a glycol, a polyglycol, a synthetic perfluoranated hydrocarbon, or mixtures or combinations of non-aqueous or aqueous liquids.

11. The method of claim 1, wherein the gas-liquid contrast medium composition further comprises at least one therapeutic agent, comprising, methotrexate, hormones, fertility enhancing compounds, fertility interfering compounds, motility enhancing compounds, motility interfering compounds, compounds affecting the cilia/deciliation cycle, cilia growth enhancing or interfering compounds, ovarian follicle treatment compounds, antibacterial, antimicrobial, antifungal, antiviral, antimycoplasmal, or antiparisital compounds, compounds that reduce inflammation or scar tissue formation, one or more antibiotics, mucoproteins, electrolytes or enzymes to enhance or inhibit fertility, progesterone, estrogen, adrenergic active compounds, noradrenergic active compounds, nonsteroidal anti-inflammatory drug, prostaglandins, hormones for fertility, fertility enhancing compounds, gametes, sperm, ova, combinations of sperm and ova, one or more zygotes, or one or more embryos, or combinations thereof.

12. A method of diagnosing the interior structure of a uterus, and optionally, the patency of two fallopian tubes, comprising, a) providing to a uterus or to two fallopian tubes, a contrast medium composition made by a contrast medium generating and delivery device, comprising, i) a container assembly comprising a first and second container, the first container configured for containing a liquid and the second container configured for containing air or gas; a contrast medium generating chamber; a first connection for fluid connection between the first container and the contrast medium generating chamber, and a second connection for fluid connection between the second container and the contrast medium generating chamber; an air port positioned between the second container and the contrast medium generating chamber in the connection for fluid connection between the second container and the contrast medium generating chamber, that is in fluid connection with the second container; and a third connection for fluid connection between the contrast medium generating chamber and an exit port distal to the contrast medium generating chamber;

ii) first and second container plungers, respectively disposed within the first and second containers for firstly simultaneously moving the liquid or the air or gas into the respective container, and secondly for simultaneously moving the contained liquid or the air or gas from the respective container, through the respective first and second connection for fluid connection, to the contrast medium generating chamber to form a contrast medium comprising the liquid and the air or gas that exits through the exit port; and b) viewing the contrast medium composition in the uterus or two fallopian tubes and diagnosing the structure of the uterus.

13. The method of claim 12, wherein the viewing is by sonography.

14. The method of claim 12, wherein the device further comprises a component for actuating both container plungers simultaneously.

15. The method of claim 12, wherein the device further comprises at least one check valve that is in fluid connection with the container in fluid connection with the air port.

16. The method of claim 12, wherein the device further comprises at least two check valves are in fluid connection with the container in fluid connection with the air port.

17. The method of claim 12, wherein the device further comprises a stop cock positioned between the contrast generating chamber and the exit port.

18. The method of claim 12, wherein the device further comprises a catheter attached to the exit port.

19. The method of claim 12, wherein the liquid further comprises one or more of a surfactant, emulsifier, stabilizing or dispersing agents.

20. The method of claim 12, wherein the surfactant, emulsifier, stabilizing or dispersing agent comprises one or more of a tenside, a lecithin; phosphatidyl-choline; an ester or ether of fatty acids and fatty alcohols with polyoxyethylene; polyoxyethylated polyols; sorbitol, glycols and glycerol, cholesterol; polyoxy-ethylene-polyoxypropylene polymers, viscosity raising and stabilizing compounds, mono- and polysaccharides, glucose, lactose, sucrose, dextran;
glycerol, polyglycols; and polypeptides; proteins, gelatin, oxypolygelatin, plasma protein,
amphipathic compounds capable of forming stable films in the presence of water and gases;
phospholipids, phosphatidic acid (PA), phosphatidylinositol, phosphatidylethanolamine (PE), phosphatidylserine (PS), phosphatidylglycerol (PG), cardiolipin (CL), sphingomyelins, a plasmogen, a cerebroside, egg lecithin or soya bean lecithin, or synthetic lecithins;
dimyristoylphosphatidylcholine, dipalmitoylphosphatidylcholine; distearoylphosphatidylcholine;
unsaturated synthetic lecithins, dioleylphosphatidylcholine, dilinoleylphosphatidylcholine, free fatty acids, esters of fatty acids with polyoxyalkylene compounds; polyoxypropylene glycol;
polyoxyalkylene glycol; ethers of fatty alcohols with polyoxyalkylene glycols; esters of fatty acids with polyoxyalklated sorbitan; soaps; glycerol-polyalkylene stearate; glycerol-polyoxyethylene ricinoleate; homo- and copolymers of polyalkylene glycols; polyethoxylated soya-oil and castor oil or hydrogenated derivatives of polyethoxylated soya-oil and castor oil; ethers and esters of sucrose with fatty acids or fatty alcohols, polyoxyalkylated ethers and esters of sucrose with fatty acids or fatty alcohols; mono-di- and triglycerides of saturated or unsaturated fatty acids;
glycerides of soya-oil and sucrose, block copolymers of polyoxypropylene and polyoxyethylene (poloxamers), polyoxyethylenesorbitans, glycerol-polyalkylene stearate, glycerolpolyoxyethylene ricinoleate, homo- and copolymers of polyalkylene glycols, glycerides of soya-oil, dextran, sucrose and carbohydrates; polymerizable amphiphilic compounds of linoleyl-lecithins or polyethylene dodecanoate, phosphatidic acid, phosphatidylcholine, phosphatidylethanolamine, phosphatidylserine, phosphatidylglycerol, phosphatidylinositol, cardiolipin, sphingomyelin;
phosphatidylcholine (PC) dioleylphosphatidylcholine; dimyristoylphosphatidylcholine (DMPC), dipentadecanoylphosphatidylcholine-, dilauroylphosphatidylcholine (DLPC);
dipalmitoylphosphatidylcholine (DPPC); disteraoylphosphatidylcholine (DSPC);
diarachidonylphosphatid-ylcholine (DAPC); phosphatidylethanolamines (PE),
dioleylphosphatidylethanolamine, dipalmitoylphosphatidylethanolamine (DPPE) distearoylphosphatidylethanolamine (DSPE); phosphatidylserine (PS), dipalmitoyl phosphatidylserine (DPPS), disteraoylphosphatidylserine (DSPS); phosphatidylglycerols (PG), dipalmitoylphosphatidylglycerol (DPPG), distearoylphosphatidylglycerol (DSPG); or phosphatidylinositol.

21. The method of claim 12, wherein the liquid is water; a physiological electrolyte solution, a physiological saline solution, Ringer's solution, an aqueous solution of sodium chloride,
calcium chloride, sodium bicarbonate, sodium citrate, sodium acetate, or sodium tartrate; a glucose solution, a solutions of mono- or polyhydric alcohol, ethanol, n-butanol, ethylene glycol, polyvinylpyrrolidone, a physiologically acceptable non-aqueous solution, an anhydrous or substantially anhydrous carrier liquid, a solution of an alcohol, a glycol, a polyglycol, a synthetic perfluoranated hydrocarbon, or mixtures or combinations of non-aqueous or aqueous liquids.

22. The method of claim 12, wherein the gas-liquid contrast medium composition further comprises at least one therapeutic agent, comprising, methotrexate, hormones, fertility enhancing compounds, fertility interfering compounds, motility enhancing compounds, motility interfering compounds, compounds affecting the cilia/deciliation cycle, cilia growth enhancing or interfering compounds, ovarian follicle treatment compounds, antibacterial, antimicrobial, antifungal, antiviral, antimycoplasmal, or antiparisital compounds, compounds that reduce inflammation or scar tissue formation, one or more antibiotics, mucoproteins, electrolytes or enzymes to enhance or inhibit fertility, progesterone, estrogen, adrenergic active compounds, noradrenergic active compounds, nonsteroidal anti-inflammatory drug, prostaglandins, hormones for fertility, fertility enhancing compounds, gametes, sperm, ova, combinations of sperm and ova, one or more zygotes, or one or more embryos, or combinations thereof.

\* \* \* \* \*